(12) United States Patent
Wang

(10) Patent No.: US 6,291,438 B1
(45) Date of Patent: *Sep. 18, 2001

(54) ANTIVIRAL ANTICANCER POLY-SUBSTITUTED PHENYL DERIVATIZED OLIGORIBONUCLEOTIDES AND METHODS FOR THEIR USE

(76) Inventor: Jui H. Wang, 477 Le Brun Rd., Amherst, NY (US) 14226

(*) Notice: Subject to any disclaimer, the term of this patent is extended or adjusted under 35 U.S.C. 154(b) by 0 days.

This patent is subject to a terminal disclaimer.

(21) Appl. No.: 09/167,375

(22) Filed: Oct. 6, 1998

Related U.S. Application Data

(63) Continuation-in-part of application No. 08/604,871, filed on Feb. 22, 1996, now Pat. No. 5,858,988, which is a continuation-in-part of application No. 08/200,650, filed on Feb. 23, 1994, now Pat. No. 5,496,546, which is a continuation-in-part of application No. 08/022,055, filed on Feb. 24, 1993, now abandoned.

(51) Int. Cl.$^7$ .............. C12Q 1/68; C07H 21/02; C07H 21/04; C12N 15/85; C12N 15/86; C12P 19/34
(52) U.S. Cl. .......... 514/44; 435/91.1; 435/325; 435/375; 435/6; 536/23.1; 536/24.3; 536/24.31; 536/24.33; 536/24.5; 536/25.3
(58) Field of Search .......... 435/91.1, 91, 440, 435/325; 536/23.1, 24.5; 514/44

(56) References Cited

U.S. PATENT DOCUMENTS

| | | | |
|---|---|---|---|
| 4,966,843 | 10/1990 | McCormick et al. | 435/69.51 |
| 5,087,617 | 2/1992 | Smith | 514/44 |
| 5,091,374 | 2/1992 | Carter | 514/44 |
| 5,132,292 | 7/1992 | Carter | 514/44 |
| 5,248,671 | 9/1993 | Smith | 514/44 |
| 5,466,786 | 11/1995 | Buhr et al. | 536/26.26 |
| 5,496,546 | 3/1996 | Wang et al. | 424/78.36 |
| 5,512,438 | 4/1996 | Ecker | 435/6 |
| 5,514,577 | 5/1996 | Draper et al. | 435/238 |
| 5,583,035 | 12/1996 | Kretschmer et al. | 435/375 |
| 5,614,617 | 3/1997 | Cook et al. | 536/23.1 |
| 5,627,158 | 5/1997 | Cho-Chung | 514/44 |
| 5,641,754 | 6/1997 | Iversen | 514/44 |
| 5,646,262 | 7/1997 | Korba et al. | 536/24.5 |
| 5,674,856 | 10/1997 | Furukawa et al. | 514/44 |
| 5,696,248 | 12/1997 | Peyman et al. | 536/22.1 |
| 5,707,866 | 1/1998 | Brakier-Gingras et al. | 435/367 |
| 5,858,988 | * 1/1999 | Wang | 514/44 |

FOREIGN PATENT DOCUMENTS

WO 92/20697   11/1992   (WO).

OTHER PUBLICATIONS

Dewar, Robin L., Highbarger, Helene C., Sarmiento, Marinella D., Todd, John A., Vasudevarchari, M.B., Davey, Jr., Richard T., Kovacs, Joseph A., Salzman, Norman P., Lane, H. Clifford, Urdea, Mickey S., *Application of Branched DNA Signal Amplification to Monitor Human Immunodeficiency Virus Type I Burden in Human Plasma*, The Journal Of Infectious Diseases, 1994; 170:1172–9.

Bilello, J.A., Bilello, P.A., Prichard, Mark, Robins, Terry, and Drusano, G.L., *Reduction of the In Vitro Activity of A77003, an Inhibitor of Human Immunodeficiency Virus Protease, by Human Serum $\alpha_1$Acid Glycoprotein*, The Journal of Infectious Diseases, 1995; 171:546–51.

Hertogs, Kurt, DeBethune, Marie–Pierre, Miller, Veronica, Ivens, Tania, Schel, Patricia, Van Cauwenberge, Anja, Van Den Eynde, Christel, Van Gerwen, Veerle, Azun, Hilde, Van Houtte, Margriet, Peeters, Frank, Stasqewski, Schlomo, Conant, Marcus, Bloor, Stuart, Kemp, Sharon, Larder, Brendan, Pauwels, Rudi, *A Rapid Method for Simultaneous Detection of Phenotypic Resistance to Inhibitors of Protease and Reverse Transcriptase in Recombinant Human Immunodeficiency Virus Type I Isolates from Patients Treated with Antiretroviral Drugs*, Antimicrobial Agents and Chemotherapy, Feb. 1998, pp. 269–276.

(List continued on next page.)

Primary Examiner—George C. Elliott
Assistant Examiner—Janet Epps
(74) Attorney, Agent, or Firm—Fliesler, Dubb, Meyer & Lovejoy

(57) ABSTRACT

In accordance with the present invention, antisense oligonucleotides are provided with enhanced membrane permeability and stability. This is accomplished in accordance with the invention through conjugating oligoribonucleotides with a hydrophobic carrier agent at the 2'-O position of the oligonucleotides. The hydrophobic carrier agent comprises a compound of the following general structure:

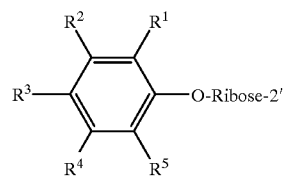

wherein $R^1$, $R^2$, $R^3$, $R^4$, and $R^5$ are independently H, $NO_2$, halide, linear or branched alkyl, linear or branched acyl, linear or branched alkylene, linear or branched O-alkyl, linear or branched amido, linear or branched S-alkyl, mono or disubstituted amine, linear or branched thioamido, phosphothionate, or phosphothioate. In a preferred embodiment, $R^1$ and $R^3$ are $NO_2$. In such embodiment, it will be appreciated that when $R^2$, $R^4$, and $R^5$ are H, the compound is DNP and when $R^4$ is F, the compound is FDNP. In another preferred embodiment, the antisense oligoribonucleotide comprises a sequence complementary to a cellular or viral gene, and application of the derivatized antisense oligoribonucleotide inhibits the expression of said gene.

48 Claims, 21 Drawing Sheets

OTHER PUBLICATIONS

Boucher, Charles A., Keulen, Wilco, Van Bommel, Toon, Nijhuis, Monique, De Jong, Dorien, De Jong, Menno D., Schipper, Pauline, Back, Nicole K. T., *Human Immunodeficiency Virus Type I Drug Susceptibility Determination by Using Recombinant Viruses Generated from Patient Sera Tested in a Cell–Killing Assay, Antimicrobial Agents and Chemotherapy,* Oct. 1996, pp. 2404–2409.

Mellors, John W., Rinaldo Jr., Charles R., Gupta, Phalguni, White, Roseanne M., Todd, John. A., Kingsley, Lawrence A., *Prognosis in HIV–1 Infection Predicted by the Quantity of Virus in Plasma, Science,* vol. 272, May 24, 1996; pp. 1167–1170.

van Gemen, Bob, van Beuiningen, Rinie, Nabbe, Arjan, van Strijp, Dianne, Jurriaans, Suzanne, Lens, Peter, Kievits, Tim, *A one–tub quantitative HIV–1 RNA NASBA nucleic acid amplification assay using elecctrochemiluminescent (ECL) labelled probes, Journal of Virological Methods 49,* 1994, pp. 157–168.

Jellinger, Robert M., Shafer, Robert W., Merigan, Thomas C., *A Novel Approach to Assessing the Drug Susceptibility and Replication of Human Immunodeficiency Virus Type I Isolates, The Journal Of Infectious Diseases,* 1997; 175:561–6.

Kellam, Paul, Larder, Brendan A., *Recombinant Virus Assay: a Rapid, Phenotypic Assay for Assessment of Drug Susceptibility of Human Immunodeficiency Virus Type I Isolates, Antimicrobial Agents and Chemotherapy,* Jan. 1994, pp. 23–30.

Saag, M.S., Holodniy, M., Duritzkes, D.R., O'Brien, W.A., Coombs, R., Poscher, M.E., Jacobsen, D.M., Shaw, G.M., Richman, D.D., Volberding, P.A., *HIV viral load markers in clinical practice, Nature Medicine,* vol. 2, No. 6, June, 1996; pp. 625–629.

Marshall, C., Allen, U.D., Cassol, S., Lapointe, N., King, SM, Read, S., Forbes, J., Moore, D., Gilmour, J., Bortolussi, B., Tobin, J., Wells, G., Conway, B. and the Canadian Pediatric Aids Research (CPAR) Group, *Evaluation of Novel Ziodvudine (ZDV) resistance testing methodologies, Abstract 63,* Fifth Workshop on HIV Drug Resistance, *The Clinical Utility of Resistance Testing,* vol. 1, Supplement 1, Jul. 3–6, 1996; pp. 40.

Hertogs, K., Conant, M., Schel, P., Van Cauwenberge, A., de Bethune, MP, Pauwels, R. *The RT–Antivrogram: a rapid and accurate method to Determine Phenotypic (multi)–drug resistance in Plasma of Patients Treated With Various HIV–1 RT Inhibitors,* Abstract 64, Fifth Workshop on HIV Drug Resistance, *The Clinical Utility of Resistance Testing,* vol. 1, Supplement 1, Jul. 3–6, 1996; pp. 40–41.

Schinazi, R.F., Stuyver, L., Wyseur, A., Lloyd, Jr., RM, Hough, L., Rombout, A., Rossau, R., Rimland, D., *Proviral and plasma virus genotyping using a line probe assay in nucleoside–treated HIV–infected Veterans Affairs (VA) patients,* Abstract 65, Fifth Workshop on HIV Drug Resistance, *The Clinical Utility of Resistance Testing,* vol. 1, Supplement 1, Jul. 3–6, 1996; pp. 41.

Gingeras, TR, Mamtora, G., Shen, N., Drenkow, J., Wintres, M., and Merigan, T., *Genetic Analysis of HIV–1 infected plasma using high–density Oligonucleotide arrays and Dideoxynucleotide Sequencing,* Abstract 66, Fifth Workshop on HIV Drug Resistance, *The Clinical Utility of Resistance Testing,* vol. 1, Supplement 1, Jul. 3–6, 1996; pp. 42.

De Bethune, M–P, Hertogs, K., Andries, K., Stoffels, P., Van Roey, J., Schel, P., Van Cauwenbverge, A, Van den Eynde, C., De Brabander, M., De Cree, J. and Pauwels, R., *Monitoring of anti–HIV–1 therapy by drug resistance phenotyping (RT–Antivirogram) and plasma viral load determination: a case study,* Abstract 67, Fifth Workshop on HIV Drug Resistance, *The Clinical Utility of Resistance Testing,* vol. 1, Supplement 1, Jul. 3–6, 1996; pp. 42–43.

Stuyver, L., Wyseur, A., Rombout, A., Scarcez, T., Verhofstede, C., Louwagie, Schinazi, R.F., Rossau, R., *Line Probe Assay (LiPA) for the detection of antiretroviral druge–selected mutations in the HIV–1 reverse transcriptase gene,* Abstract 68, Fifth Workshop on HIV Drug Resistance, *The Clinical Utility of Resistance Testing,* vol. 1, Supplement 1, Jul. 3–6, 1996; pp. 43.

Nesterova, Maria, Cho–Chung, Yoon S., *A Single–Injection Protein Kinase A–directed Antisense Treatment to Inhibit Tumour Growth, Nature Medicine,* vol. 1, No. 6, Jun., 1995, pp. 528–533.

Vaughn, James P., Stekler, Joanne, Demirdjo, Samuel, Mills, Jeffrey K., Caruthers, Marvin H., Iglehart, J. Dirk, Marks, Jeffrey K., *Inhibition of the erbB–2 Tyrosine Kinase Receptor in Breast Cancer Cells by Phosphoromonothioate and Phosphorodithioate Antisense Oligonucleotides, Nucleic Acids Research,* 1996, vol. 24, No. 22; pp. 4558–4564.

O'Neill, F.J., Goldberg, R.J.; Rapp, F., 1239m *Herpes Simplex Virus latency in cultured human cells following treatment with cytosine arabinoside. 2–Biochem Interactions,* vol. 77, 1972, p. 129.

Shannon, William M., 87:177597x *Selective Inhibition of RNA tumor virus replication in vitro and evaluation of candidate antiviral agents in vivo Chemical Abstracts,* vol. 87, 1977, p. 32.

Nishanian, Parunag, Huskins, Kennerth R., Stehn, Susan, Detels, Roger, Fahey, John L., *A Simple Method for Improved Assay Demonstrates that HIV p25 Antigen Is Present As Immune Complexes in Most Sera from HIV–Infected Individuals The Journal of Infectious Diseases,* vol. 162, No. 1, Jul., 1990, pp. 21–28.

Vasudevachari, Malamachanahalli B., Salzman, Norman P., Woll, Daniel R., Mast, Christopher, Uffelman, Katharina W., Todeter, Gary, Hoefheinz, David, Metcalf, Julie A., Lane, Clifford H., *Clinical Utility of an Enhanced Human Immunodeficiency Virus Type 1 p24 Antigen Capture Assay, Journal of Clinical Immunology,* vol. 13, No. 3, 1993, pp. 185–192.

Steward, David L., Herndon, William C., Jr., and Schell Klaus R., *Influence of 2'–0–acetylation on the Antiviral Activity of Polyriboneceotides, Biochimica Et Biophysica Acta,* 262 (1972) pp. 227–232.

Lesnik, Elena A., Guinosso, Charles J., Kawasaki, Andrew M., Sasmor, Henri, Zounes, Maryann, Cummins, Lendell L., Ecker, David J., Cook, Dan P., Frier, Susan M., *Oligodexynucleotides Containing 2'0–Modified Adenosin: Syntheses and Effects on Stability of DNA:RNA Duplexes, Biochemistry* 1993, 32, pp. 7832–7838.

Grzybowski, John, Will, David W., Randall, R.E., Smith, Clive A., Brown, Tom, *Synthesis and Antibody–mediated detection of Oligonucleotides Containing Multiple 2,4–dinitrophenyl Reporter Groups, Nucleic Acids Research,* 1993, vol. 21, No. 8, pp. 1705–1712.

Chen–Kon Shih, Rose, Janice M., Hansen, Gale L., Wu, Joe C., Bacolla, Albino, Griffin, Johanna A., *Chimeric Human Immunodeficiency Virus Type 1/type 2 Reverse Transcriptases Display Reversed Sensitivity To Nonnuceoside Analog Inhibitors*, Proc. Natl. Acad. Sci USA 88 vol. 88, pp. 9878–9882, Nov. 1991.

St. Clair, M.H., Martin, J.L, Tudor–Williams, G., Bach, M.C., Vavro, C.L., King, D.M., Kellam, P., Kemp, S.D., Larder, B.A. *Resistance to ddI and Sensitivity to AZT Induced by a Mutuation in HIV–1 Reverse Transcriptase*, Science, vol. 253, Sep. 27, 1991, pp. 1557–1559.

Weislow, Own S., Kiser, Rebecca, Fine, Donald L., Bader, John, Schoemaker, Robert H., Boyd, Michael R., *New Soluble–Formazan Assay for HIV–1 Cytopathic Effects: Application to High–Flux Screening of Synthetic and Natural Products for AIDS–Antiviral Activity*, Journal of the National Cancer Institute, vol. 81, No. 8, Apr. 19, 1989, pp. 577–586.

Larder, Brendan A., Darby, Graham, Richman, Douglas D., *HIV with Reduced Sensitivity to Zidovudine (AZT) Isolated During Prolonged Therapy*, Science, vol. 243, pp. 1731–1734. Mar. 31, 1989.

Larder, Brendan A., Kemp, Sharon D., *Multiple Mutations in HIV–1 Reverse Transcriptase Confer High–Level Resistance to Zidovudinee (AZT)*, Science, vol. 246, Dec. 1, 1989, pp. 1155–246.

Arnold, Edward, Jacobo–Molina, Alfredo, Nanni, Raymond G., Williams, Roger L., Lu, Xiadoe, Ding, Jianping, Clark Jr., Arthur D., Zhang, Anquiang, Ferris, Andera L., Clark, Patrick, Hizi, Amnon, Hughes, Stephen H., *Nature*, vol. 357, May 7, 1992, pp. 85–89.

Kohlstaedt, L.A., Wang, J., Friedman, J.M., Rice, P.A., Steitz, T.A., *Crystal Structure at 3.5 Å Resolution of HIV–1 Reverse Transcriptase Complexed with an Inhibitor*, Science vol. 256, Jun. 26, 1992, pp. 1783–1790.

Daniel, Muthiah D., Kirchoff, Frank, Czajak, Susan C., Sehgal, Prabhat K., Desrosiers, Ronald C., *Protective Effects of a Live Attenuated SIV Vaccine with a Deletion in the nef Gene*, Science, vol. 258, Dec. 18, 1992, pp. 1938–1941.

Shannon, William M., *Selective: Inhibition of RNA Tumor Virus Replication in virtro and Evaluation Of Candidate Antiviral Agents in vivo*, Annals New York Academy of Sciences, pp. 472–507, (1982).

Fukui, Toshikazu, De Clercq, Eric, *Inhibition of Murnie Leukaemia Virus Reverse Transcriptase by 2–Haologenated Polyadenylic Acids*, The Biochemical Society, vol. 203, 1982, pp. 755–760.

Ru, Kun, Taub, Mary L., Wang, Jui H., *Specific Inhibition of Breast Cancer Cells by Antisense Poly–DNP–oligoribonuceotides and Targeted Apoptosis*,Oncology Research, vol. 10, 1998, pp. 389–397.

Xin, Wei, Wang, Jui H. *Treatment of Duck Hepatatis B Virus by Antisense Poly–2'–0–(2,4–Dinitrophenyl)–Oligoribonucleotides*, Antisense and Nucleic Acid Drug Development 8:459–468 (1998).

Ashun, Mary Apea, Hu, Yin, Kang, Insug, Li, Chih C., Wang, Jiu H., *Inhibition of Murine Leukemia Virus with Poly–2'–0–(2,4–Dinitrophenyl)Poly[A]*, Antimicrobial Agents and Chemotherapy, Oct., 1996, p. 2311–2317.

Rahman, M. Habibur, Kang, Insug, Waterbury, Raymond G., Narang, Upvan, Bright, Frank V., Wang, Jui H., *Selective Removal of Riboncleases from Solution with Covalently Anchored macromolecular Inhibitor*, Analytical Chemistry, vol. 68, No. 1, Jan., 1, 1996, pp. 134–138.

Chuan, Hua, Wang, Jui H., *3'–0–(5–Fluoro–2,4–dinitrophenyl)ADP Ether and ATP Ether*, The Journal of Biological Chemistry, vol. 263, No. 26, Issue of Sep. 15., pp. 13003–13006, 1988.

Kang, Insug, Wang, Jui H., *Design of Structure–based Reverse Transcriptase Inhibitors*, The Journal of Biological Chemistry, vol. 269, No. 16, Issue of Apr. 22, pp. 12024–12031, 1994.

* cited by examiner

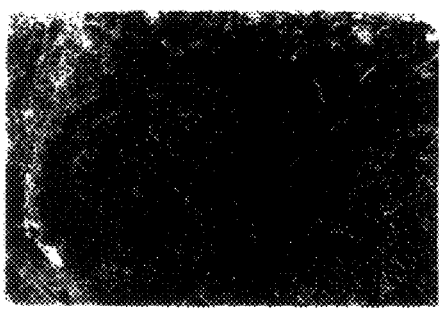
*FIG. 8A1*
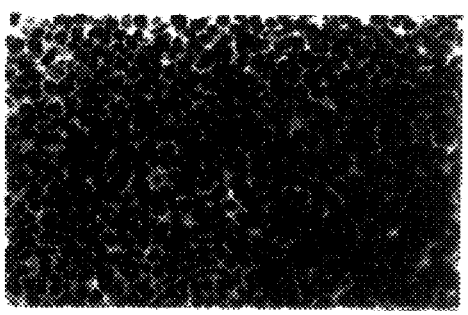
*FIG. 8A2*
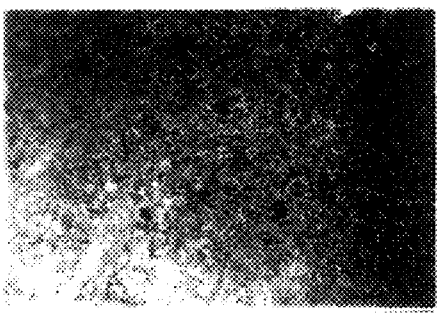
*FIG. 8B1*
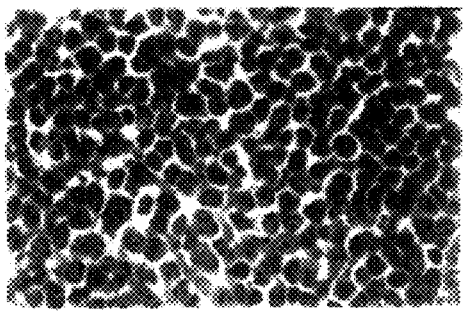
*FIG. 8B2*
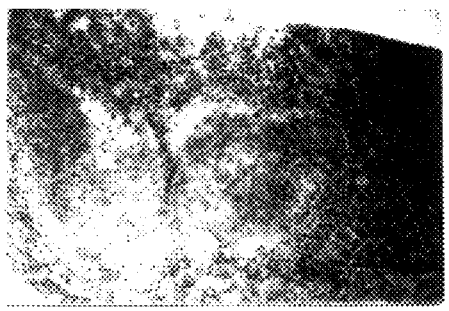
*FIG. 8C1*
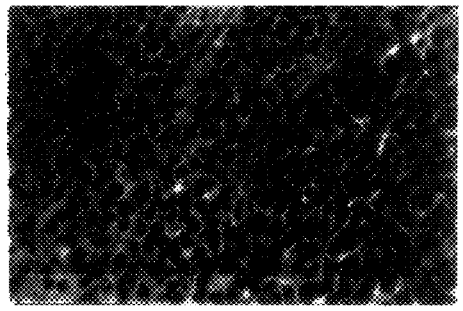
*FIG. 8C2*
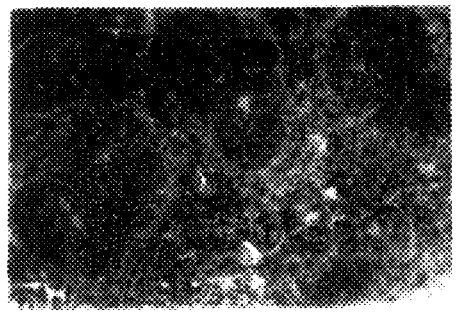
*FIG. 8D1*
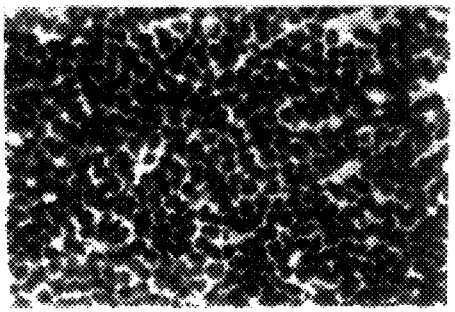
*FIG. 8D2*

(Day 20)

(Day 30)

(Day 38)

(Day 50)

FIG. 10

5'GGGACAGUCUGGUAC... (anti-protease)
...AUCGAUUAGUCCAAUUU...3' (mRNA of retrovirus)
...CUUCUCGUUU...5'
(anti-envelope)

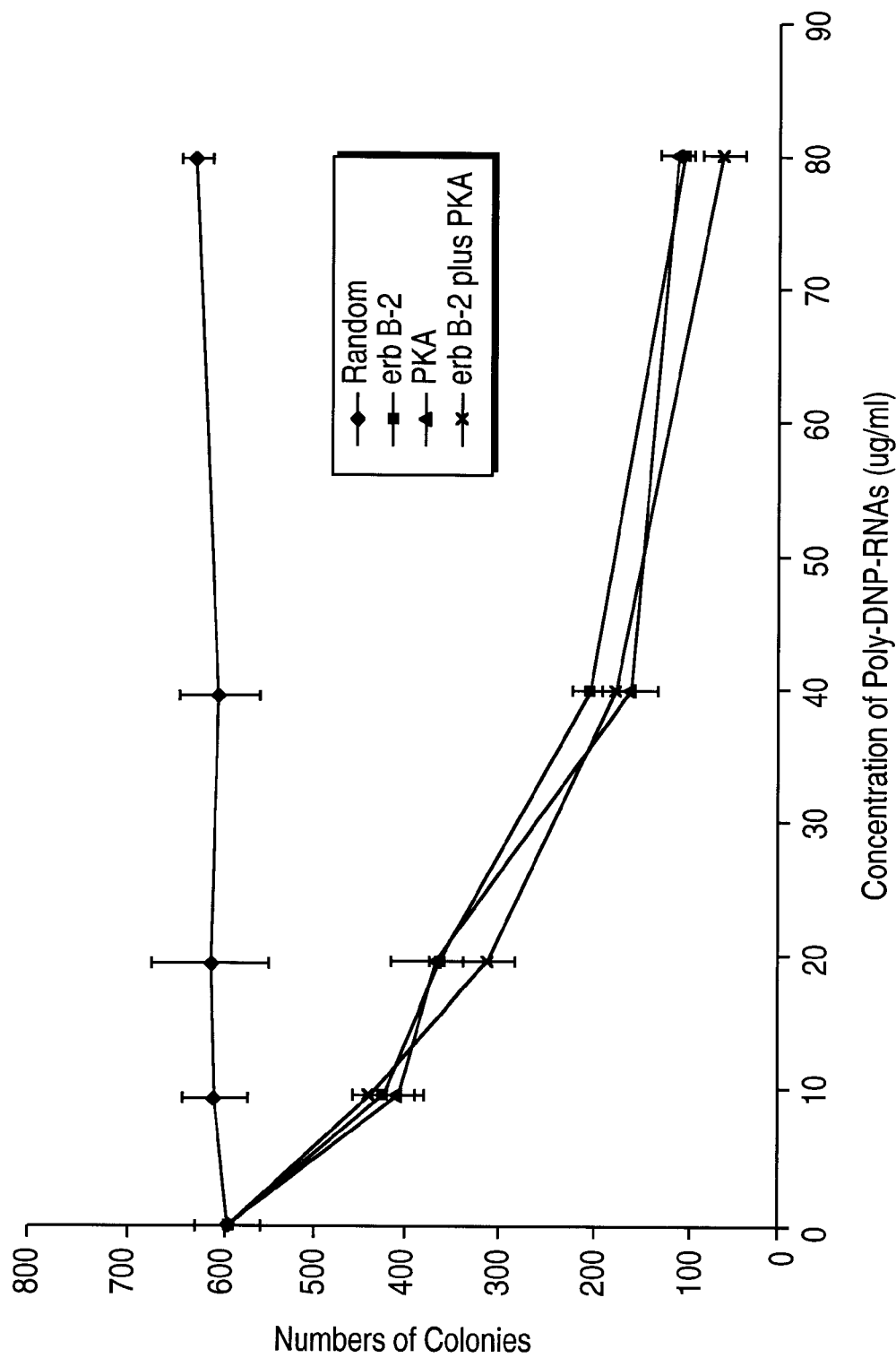

ANTIVIRAL ANTICANCER POLY-SUBSTITUTED PHENYL DERIVATIZED OLIGORIBONUCLEOTIDES AND METHODS FOR THEIR USE

RELATED PATENTS AND APPLICATIONS

This application is a continuation-in-part of U.S. Ser. No. 08/604,871, filed Feb. 22, 1996, now U.S. Pat. No. 5,858,988, issued Jan. 12, 1999, a continuation-in-part of U.S. Ser. No. 08/200,650, filed on Feb. 23, 1999, now U.S. Pat. No. 5,496,546, issued Mar. 5, 1996, a continuation-in-part of Ser. No. 08/022,055, filed Feb. 24, 1993, abandoned.

BACKGROUND OF THE INVENTION

1. Field of the Invention

The present invention relates to the field of the manufacture and delivery of antisense oligonucleotides. In particular, the present invention relates to antisense oligoribonucleotides conjugated to a carrier agent that enhances membrane permeability and stability of the antisense oligoribonucleotide constructs. Particularly preferred carrier agents include 2,4-dinitrophenyl-(DNP) and 3-fluoro-4,6-dinitrophenyl-(FDNP) groups coupled at the 2'-O position of the oligoribonucleotide. More particularly, the present invention relates to anti-viral and anti-cancer antisense oligoribonucleotide constructs and their methods of use to inhibit gene expression and phenotypic changes in cells and in animals with viral or cancerous diseases. Even more particularly, the present invention relates to methods for treating animals with viral infections and cancers.

2. Background of the Technology

Antisense oligonucleotides are nucleotide, or nucleotide analogues, whose sequence is complementary to a predetermined segment of RNA, either freshly transcribed RNA or messenger RNA (mRNA). Typically, sequences of the antisense oligonucleotides are chosen so as to be complementary to a critical sequence in a gene so that if the gene is hybridized to the complementary antisense sequence, the gene cannot be expressed or is subjected to enzymatic degradation. See Stec et al. U.S. Pat. No. 5,151,510, the disclosure of which is hereby incorporated by reference in its entirety. A huge number of diseases conceivably can be mitigated, controlled, regulated, or prevented through the disabling of gene expression that antisense therapeutics allow. Thus, antisense oligonucleotides offer an incredible opportunity for the treatment of a large number of diseases.

For example, the use of antisense oligonucleotides has been proposed for the treatment of a broad range of viral infections. See Matsukura et al. *Proc. Nat. Acad. Sci. U.S.A.* 86:4244–4448 (1989), the disclosure of which is hereby incorporated by reference in its entirety.

Further, cancer is an area ripe with opportunities for antisense approaches. See WO 92/20348 the disclosure of which is hereby incorporated by reference in its entirety. Such application relates to antisense oligonucleotides to c-myb proto-oncogene in the treatment of colorectal cancer. See also Ensoli et al. WO 94/29,444 the disclosure of which is hereby incorporated by reference in its entirety. Such application relates to antisense oligonucleotides to basic fibroblast growth factor (bFGF) in the treatment of Kaposi's sarcoma. See further Bayever et al. *Antisense Res. and Dev.* 2:109–110 (1992) the disclosure of which is hereby incorporated by reference in its entirety. Such article discusses antisense oligoribodinucleotides to p53 for the treatment of acute myeloblastic leukemia (AML).

However, antisense oligonucleotides, while appearing to be exceptionally effective in certain tests, appear to suffer from several problems. It is postulated that the major limitations on antisense oligonucleotides for use in therapeutic applications is their apparent limited membrane permeability and high susceptibility to enzymatic degradation, both within and without cells. These two factors combine to limit both the concentration and the duration (half-life) of the oligonucleotides within cells. With such limited concentration and half-life of the oligonucleotides within the cells, it appears as though much of the therapeutic potential of the antisense oligonucleotides is lost.

Thus, researchers have expended considerable effort to overcome the problems of limited membrane permeability and rapid enzymatic degradation of antisense oligonucleotides. To this end, researchers have utilized a variety of techniques designed to increase membrane permeability and mitigate the enzymatic degradation of antisense oligonucleotides.

A detailed discussion of oligonucleotide design and synthesis is presented in Uhlmann et al. *Chemical Renews* 90:543–584 (1990), the disclosure of which is hereby incorporated by reference in its entirety.

A preferred approach that has been used to enhance membrane permeability and stability of oligonucleotides is the use of alkyl-for-O substituted and S-for-O substituted nucleotide analogues. In connection with the alkyl substituted oligonucleotides, one of the phosphate oxygen atoms that is not involved with the bridge between nucleotides is substituted with an alkyl group (particularly, methyl or ethyl). Similarly, in the S-substituted oligonucleotides (phosphorothioates), one of the phosphate oxygen atoms that is not involved in the bridge is substituted with a sulfur. In the alkyl substituted oligonucleotides, a negatively charged oxygen is replaced with a neutral and sterically undemanding alkyl group (particularly methyl). With S-substituted oligonucleotides, the negative charge on the non-bridge oxygen atoms is shared asymmetrically and located primarily on the sulfur. While, with each type of substituted oligonucleotide, membrane permeability and stability appear to be enhanced, two stereoisomers are prepared that require separation following synthesis or use of non-stereoselective synthetic methods. In S-substituted oligonucleotides, this problem can be minimized through the substitution of both of the non-bridge oxygen atoms with sulfur (phosphorodithioates). Further, each type of these substituted oligonucleotides appear to suffer from a decreased hybridization affinity with RNA in cells.

While inhibition of mRNA translation is possible utilizing either antisense oligoribonucleotides or oligodeoxyribonucleotides, free oligoribonucleotides are more susceptible to enzymatic attack by ribonucleases than oligodeoxyribonucleotides. Hence, oligodeoxyribonucleotides have generally been preferred because, upon hybridization with particular mRNA, the resulting DNA-RNA hybrid duplex is a substrate for RNase H, which specifically attacks the RNA portion of DNA-RNA hybrid at the free 2'-OH. Degradation of the mRNA strand of the duplex releases the antisense oligodeoxynucleotide strand for hybridization with additional messages from the gene.

With this problem in mind, a variety of other modified oligonucleotides have been synthesized to overcome this problem. See Uhlmann et al., supra. 2'-O-methyloligoribonucleotides have been synthesized and reportedly are completely resistant to RNA- and DNA-specific nucleases. See Sproat et al. *Nucleic Acids Res.*

17:3373 (1989), the disclosure of which is hereby incorporated by reference in its entirety. Less specific nucleases, however, cleave the 2'-O-methyloligoribonucleotides with varying efficiencies. Further, the same group reported the synthesis of other, larger, 2'-O-allyl-substituted oligoribonucleotides. See Iribarren et al. *Proc. Nat. Acad. Sci. U.S.A.*, 87:7747 (1990), the disclosure of which is hereby incorporated by reference in its entirety. The paper reports that 2'-O-(2-propylene)-oligoribonucleotides are more stable than 2'-O-methyloligoribonucleotides and show improved specific binding. A branched, five carbon allyl substituted oligoribonucleotide (2'-O-(3,3-dimethyl-2-butene)-oligoribonucleotide) also substantially improved the resistance of the oligonucleotide to nuclease digestion. However, such oligonucleotide showed a substantially reduced hybridization with complementary RNA sequences.

In addition to the approaches described above for enhancing permeability and stability of oligonucleotides, a variety of groups have worked on incorporating oligonucleotides into specific carriers or binding oligonucleotides to specific or nonspecific delivery agents. For example, liposomal delivery of oligonucleotides appears to hold great promise. Liposomes are microscopic vesicles composed of mono- or multi-lamellar lipid bilayers which enter cells by phagocytosis or endocytosis. In addition to liposomes, pol-L-lysine has been used as a delivery agent to enhance interaction with cells. Other possible strategies are discussed by Uhlmann et al., supra. Nevertheless, there remains a need in the antisense oligonucleotide art for an effective approach to enhance the delivery of oligonucleotides. Further, there remains a need in the art for an effective approach to mitigate enzymatic degradation of oligonucleotides. Moreover, it would be advantageous if such benefits could be achieved without a substantial reduction in the hybridization affinity of antisense oligonucleotides to cellular RNA.

SUMMARY OF THE INVENTION

To overcome the problems of the prior art, this invention provides for oligoribonucleotides with improved membrane permeability and stability, both inside and outside cells. The oligoribonucleotides of this invention therefore can be used to alter gene transcription and/or translation for any gene or gene segment responsible for expression.

In accordance with the first aspect of this invention, oligoribonucleotides are provided which inhibit viral reverse transcriptase, inhibit the expression of leukemia virus, hepatitis virus, oncogenes, and human immunodeficiency virus. Using the oligoribonucleotides of this invention, it is possible to inhibit any gene for which the sequences of critical domains or regulatory elements are known.

In accordance with another aspect of the present invention, there is provided an antisense oligoribonucleotide conjugated at the 2'-O position with a compound of the following general structure:

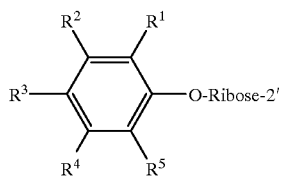

wherein $R^1$, $R^2$, $R^3$, $R^4$, and $R^5$ are independently H, $NO_2$, halide, linear or branched alkyl, linear or branched acyl, linear or branched alkylene, linear or branched O-alkyl, linear or branched amido, linear or branched S-alkyl, mono or disubstituted amine, linear or branched thioamido, phosphothionate, or phosphothioate.

In a preferred embodiment, $R^1$ and $R^3$ are $NO_2$ as follows:

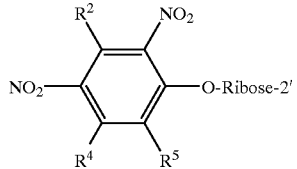

In another preferred embodiment, $R^2$, $R^4$, and $R^5$ are H. In a preferred embodiment, the oligoribonucleotide has a length of between 10 and 50 nucleotides or alternatively, 10 and 40 nucleotides. In another preferred embodiment, the oligoribonucleotide has a length of between 12 and 30 nucleotides. In another preferred embodiment, the oligoribonucleotide has a length of between 15 and 25 nucleotides.

In another preferred embodiment, at least one of the 5'-OH and 3'-OH ends of the oligoribonucleotide is conjugated with a compound of the following general structure:

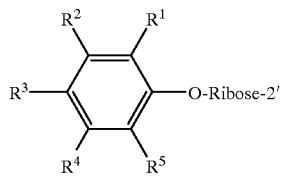

wherein $R^1$, $R^2$, $R^3$, $R^4$, and $R^5$ are independently H, $NO_2$, halide, linear or branched alkyl, linear or branched acyl, linear or branched alkylene, linear or branched O-alkyl, linear or branched amido, linear or branched S-alkyl, mono or disubstituted amine, linear or branched thioamido, phosphothionate, or phosphothioate.

In a preferred embodiment, $R^1$ and $R^3$ are $NO_2$. In another preferred embodiment, $R^2$, $R^4$, and $R^5$ are H.

In accordance with a second aspect of the present invention, there is provided an antisense oligoribonucleotide derivatized at a plurality of 2'-O positions with a hydrophobic group selected from the group consisting of a 2,4-dintrophenyl group and a 3-fluoro-4,6-dintrophenyl group. In a preferred embodiment, the oligoribonucleotide has a length of between 10 and 50 nucleotides, alternatively 10 and 40 nucleotides. In another preferred embodiment, the oligoribonucleotide has a length of between 12 and 30 nucleotides. In another preferred embodiment, the oligoribonucleotide has a length of between 15 and 25 nucleotides.

In accordance with a third aspect of the present invention, there is provided a method of enhancing membrane permeability and stability of an antisense oligoribonucleotide, comprising: providing an antisense oligoribonucleotide having a plurality of 2'-O positions, conjugating a compound of the following general structure to the 2'-O position of the oligoribonucleotide:

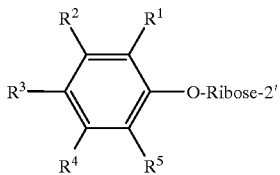

wherein $R^1$, $R^2$, $R^3$, $R^4$, and $R^5$ are independently H, $NO_2$, halide, linear or branched alkyl, linear or branched acyl, linear or branched alkylene, linear or branched O-alkyl, linear or branched amido, linear or branched S-alkyl, mono or disubstituted amine, linear or branched thioamido, phosphothionate, or phosphothioate.

In a preferred embodiment, $R^1$ and $R^3$ are $NO_2$. In another preferred embodiment, $R^2$, $R^4$, and $R^5$ are H. In a preferred embodiment, the oligoribonucleotide has a length of between 10 and 50 nucleotides, alternatively 10 and 40 nucleotides. In another preferred embodiment, the oligoribonucleotide has a length of between 12 and 30 nucleotides. In another preferred embodiment, the oligoribonucleotide has a length of between 15 and 25 nucleotides. In another preferred embodiment, at least one of the 5'-OH and 3'-OH ends of the oligoribonucleotide is conjugated with a compound of the following general structure:

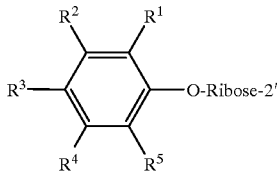

wherein $R^1$, $R^2$, $R^3$, $R^4$, and $R^5$ are independently H, $NO_2$, halide, linear or branched alkyl, linear or branched acyl, linear or branched alkylene, linear or branched O-alkyl, linear or branched amido, linear or branched S-alkyl, mono or disubstituted amine, linear or branched thioamido, phosphothionate, or phosphothioate. In a preferred embodiment, $R^1$ and $R^3$ are $NO_2$. In another preferred embodiment, $R^2$, $R^4$, and $R^5$ are H.

The nucleotide sequences of a preferred embodiment comprise sequences complementary to at least one region of a gene or gene transcript, wherein the region is important for expression of the gene product. Preferred oligoribonucleotide include multifunctional oligoribonucleotides comprising nucleotide sequences complementary to portions of different genes or gene transcripts. A preferred embodiment comprises multifunctional oligoribonucleotides having a length of between 10 and 50 nucleotides. In another preferred embodiment, the oligoribonucleotides have a length of between 10 and 40 nucleotides. In yet another preferred embodiment, the oligoribonucleotides have lengths between about 10 and about 30 nucleotides. In another preferred embodiment, the oligoribonucleotides have a length of between 15 and 25 nucleotides.

In accordance with a fourth aspect of the present invention, there is provided an improved method for inhibiting gene expression, comprising administering an antisense oligonucleotide comprising a plurality of 2'-O positions in a manner designed inhibit gene expression, the improvement comprising: derivatizing the antisense oligonucleotide at a plurality of the 2'-O positions with a compound of the following structure:

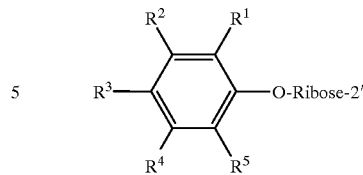

wherein $R^1$, $R^2$, $R^3$, $R^4$, and $R^5$ are independently H, $NO_2$, halide, linear or branched alkyl, linear or branched acyl, linear or branched alkylene, linear or branched O-alkyl, linear or branched amido, linear or branched S-alkyl, mono or disubstituted amine, linear or branched thioamido, phosphothionate, or phosphothioate.

In a preferred embodiment, $R^1$ and $R^3$ are $NO_2$. In another preferred embodiment, $R^2$, $R^4$, and $R^5$ are H. In another preferred embodiment, the oligoribonucleotide has a length of between 10 and 50 nucleotides. In another preferred embodiment, the oligoribonucleotide has a length of between 10 and 40 nucleotides, preferably between 12 and 30 nucleotides. In another preferred embodiment, the oligoribonucleotide has a length of between 15 and 25 nucleotides. In another preferred embodiment, at least one of the 5'-OH and 3'-OH ends of the oligoribonucleotide is conjugated with a compound of the following general structure:

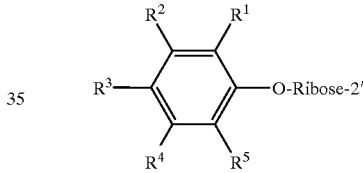

wherein $R^1$, $R^2$, $R^3$, $R^4$, and $R^5$ are independently H, $NO_2$, halide, linear or branched alkyl, linear or branched acyl, linear or branched alkylene, linear or branched O-alkyl, linear or branched amido, linear or branched S-alkyl, mono or disubstituted amine, linear or branched thioamido, phosphothionate, or phosphothioate. In another preferred embodiment, $R^1$ and $R^3$ are $NO_2$. In another preferred embodiment, $R^2$, $R^4$, and $R^5$ are H.

In accordance with a fifth aspect of the present invention, there is provided an improved antisense method, comprising administering an antisense oligonucleotide comprising a plurality of 2'-O positions in a manner designed inhibit gene expression, comprising derivatizing the antisense oligonucleotide at a plurality of the 2'-O positions with a group selected from the group consisting of a 2,4-dintrophenyl group and a 3-fluoro-4,6-dintrophenyl group. In a preferred embodiment, the oligoribonucleotide has a length of between 10 and 50 nucleotides, preferably between 10 and 40 nucleotides. In another preferred embodiment, the oligoribonucleotide has a length of between 12 and 30 nucleotides. In another preferred embodiment, the oligoribonucleotide has a length of between 15 and 25 nucleotides. In another preferred embodiment, at least one of the 5'-OH and 3'-OH ends of the oligoribonucleotide is conjugated with a compound of the following general structure:

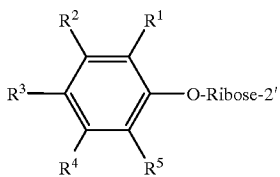

wherein $R^1$, $R^2$, $R^3$, $R^4$, and $R^5$ are independently H, $NO_2$, halide, linear or branched alkyl, linear or branched acyl, linear or branched alkylene, linear or branched O-alkyl, linear or branched amido, linear or branched S-alkyl, mono or disubstituted amine, linear or branched thioamido, phosphothionate, or phosphothioate. In another preferred embodiment, $R^1$ and $R^3$ are $NO_2$. In another preferred embodiment, $R^2$, $R^4$, and $R^5$ are H.

In accordance with another method of the present invention, a preferred method for inhibiting gene expression comprises administering an oligoribonucleotide to an animal, wherein the expression of a gene is inhibited by the oligoribonucleotide. In another preferred embodiment, a multifunctional oligoribonucleotide is administered to an animal in order to inhibit the expression of at least one gene in the animal or a virus. In another preferred embodiment of the invention, the oligoribonucleotide is in the range of between 10 and 50 nucleotides in length. In another preferred embodiment, the oligoribonucleotide is between 10 and 40 nucleotides in length. In another preferred embodiment, the oligoribonucleotide is between 12 and 30 nucleotides in length. In another preferred embodiment, the oligoribonucleotide is between 15 and 25 nucleotides in length.

BRIEF DESCRIPTION OF THE DRAWING FIGURES

■ [$^{14}C$] DNP-poly [A] into lymphocytes;

△ [$^{14}C$] DNP-poly [A] into leukocytes;

○ [$^{14}C$] poly [A] into lymphocytes; and

● [$^{14}C$] poly [A] into leukocytes.

Figure 3:
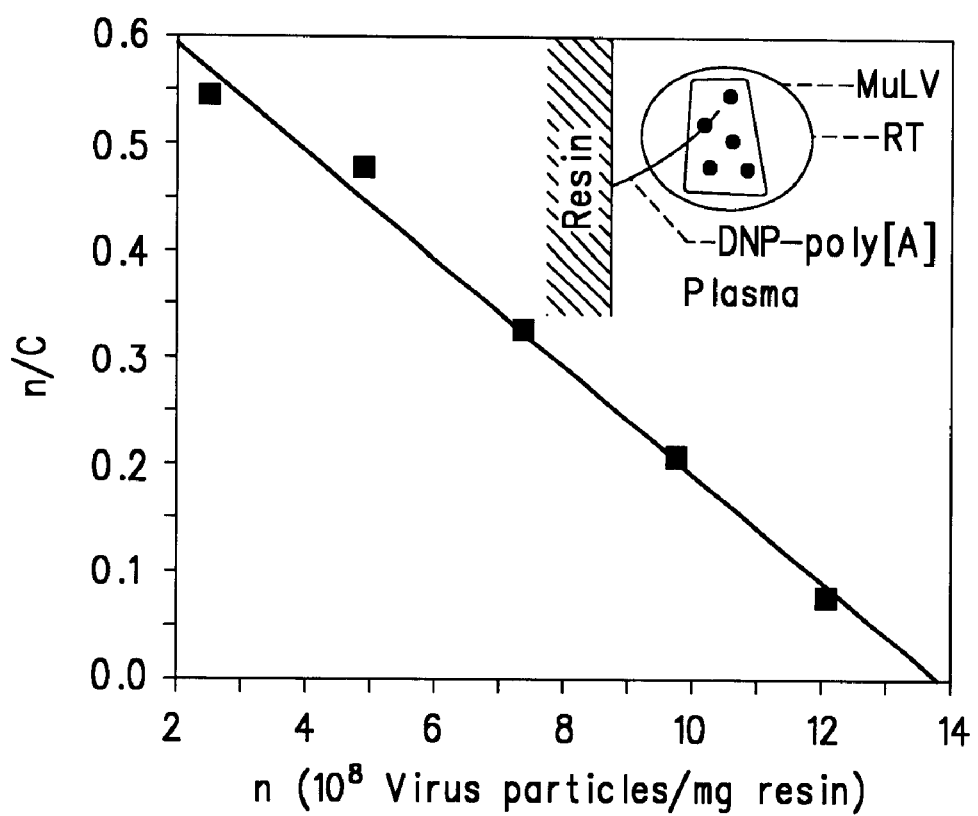

FIG. 3 is a graph showing the observed binding equilibrium of MuLV in human plasma to acrylamide beads covalently attached to DNP-poly [A]. The inset shows the assumed mode of binding. C denotes the molar concentration of free virus; n denotes the number of moles of virus bound per milligram of resin.

Figure 4:
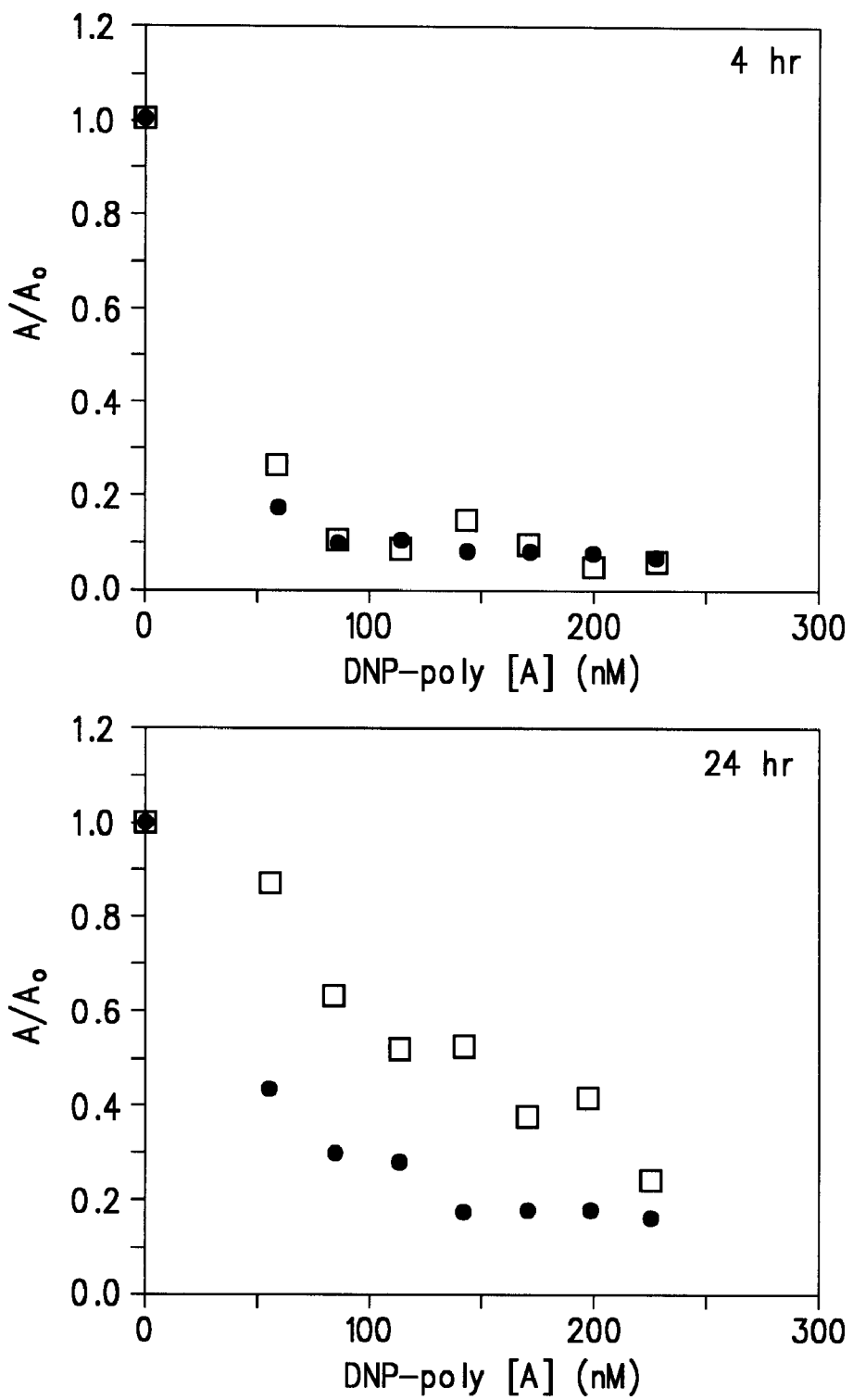

FIG. 4 shows two graphs showing the effects of 4 hour (top) and 24 hour (bottom) preincubation at 37° C. on the inhibition potency of DNP-poly [A] on 25 nM concentration of HIV RT, as follows:

☐ preincubation in 0.01 M HCl; and

● preincubation in DEPC-treated water.

Figure 5:
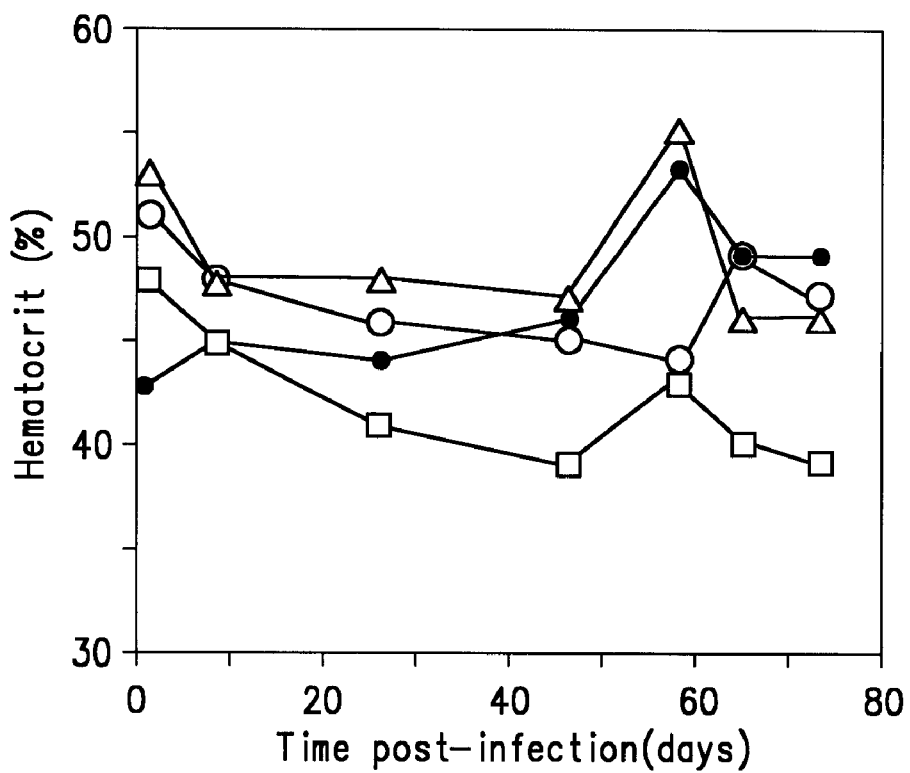

FIG. 5 is a graph showing hematocrit readings for mice infected with $10^4$–$10^5$ virus particles i.p. at 1–73 days after injection, as follows:

☐ viremia;

● normal;

○ drug (1–10 mg DNP-poly [A]/kg in one dose); and

△ viremia+drug (1–10 mg DNP-poly [A]/kg in one dose).

Figure 6A:
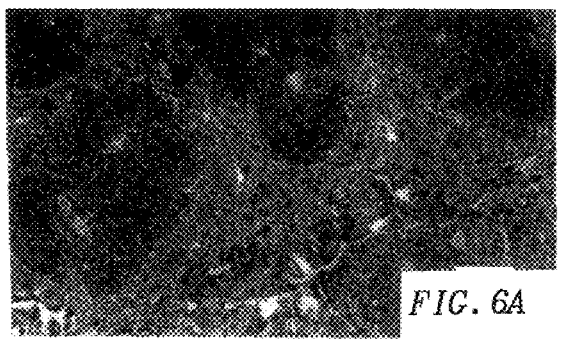
Figure 6B:
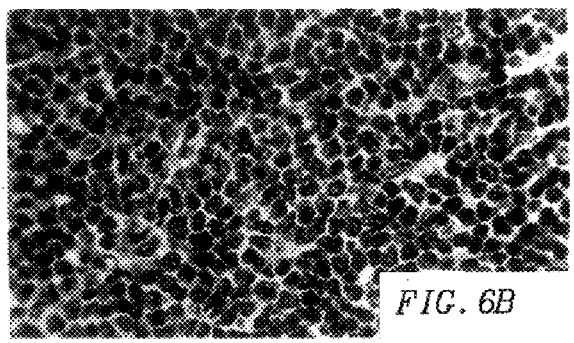
Figure 6C:
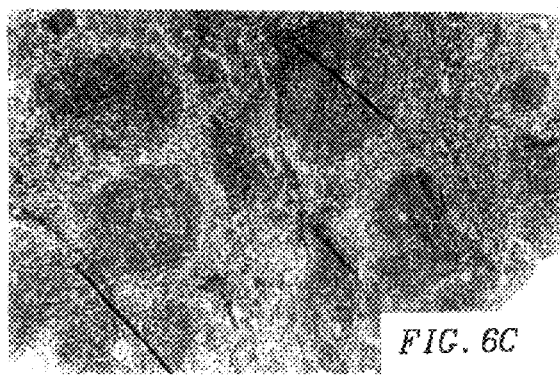

FIGS. 6a to 6d are a series of photomicrographs showing sections of spleens from mice that were treated with 10 mg of DNP-poly [A], 3 times over 1 week, immediately after virus injection, as follows:

FIG. 6a infected and treated (160×);

FIG. 6b infected and treated (1600×);

FIG. 6c uninfected but treated (160×); and

Figure 6D:
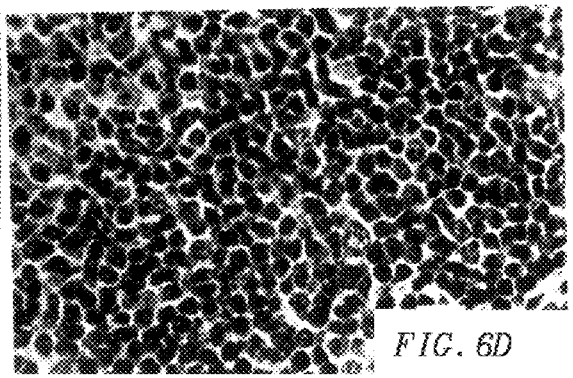

FIG. 6d uninfected but treated (1600×).

The mice were sacrificed at approximately 3 months after virus infection. The spleens were preserved in formalin and subsequently stained with hematoxylin and eosin (H & E).

Figure 7A:
Figure 7B:
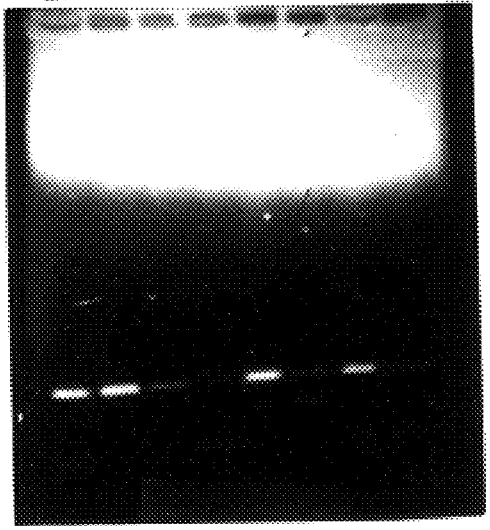
Figure 7C:

FIGS. 7a to FIG. 7d are a series of photographs of electrophoresis gels showing the effect on mice that were infected with $10^8$ virus particles of MuLV when treated with 100 mg DNP-poly [A]/kg body weight. The mice were infected for up to four months and then treated with DNP-poly [A] by i.p. injection, as follows:

FIG. 7a shows the results prior to treatment (Lanes 1–8 correspond to mouse numbers 1–8);

FIG. 7b shows the results after 1 week of treatment (Lanes 1–8 correspond to mouse numbers 1–8);

FIG. 7c shows the results two weeks after treatment (Lane 1=PCR Ladder; Lane 2=normal mouse; Lane 3=mouse 1; Lanes 4–7 correspond to mouse numbers 3–6; and Lane 8=mouse 8).

Figure 7D:

FIG. 7d shows the results three weeks after treatment (Lane 1=molecular size ladder; Lane 2=mouse 1; Lanes 3–6 correspond to mouse numbers 3–6; Lane 7=mouse 8; and Lane 8=normal mouse).

Figure 1:
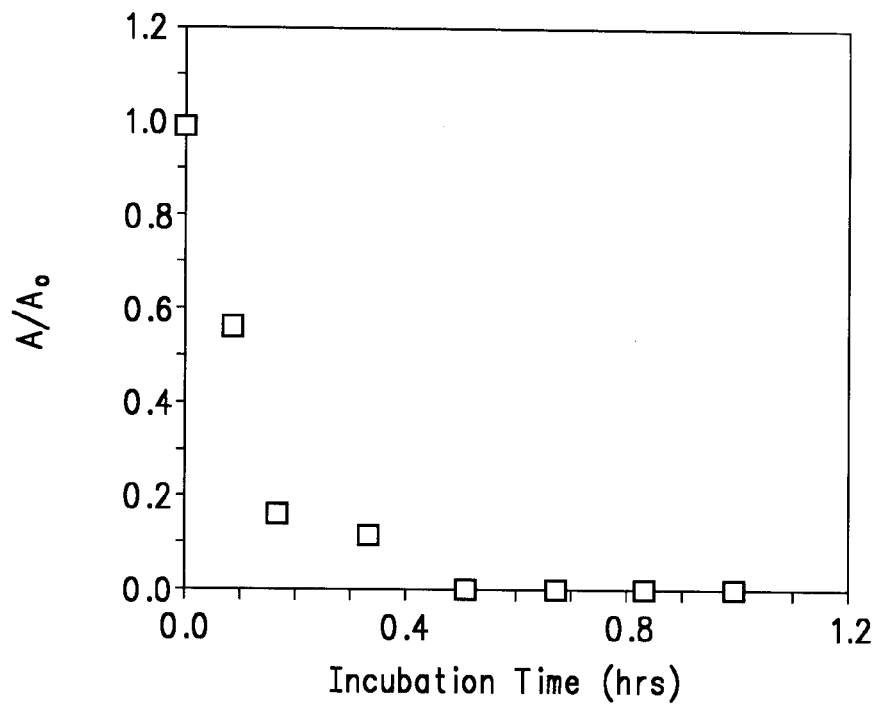
FIG. 1 is a graph showing the transport of DNP-poly [A] into MuLV virus particles and inhibition of the MuLV RT inside as a function of incubation time at 0° C.
Figure 2:
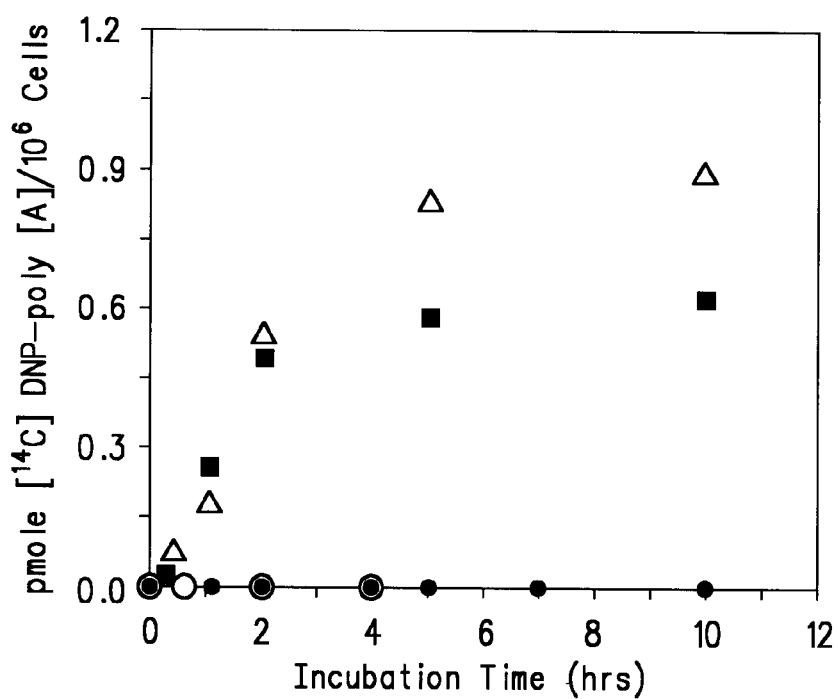
FIG. 2 is a graph showing the transport of DNP derivatized labeled poly [A] and the lack of transport of underivatized labeled poly [A] molecules into human cells at 37° C. as follows.

FIG. 8a1 to FIG. 8d2 are a series of photomicrographs showing immunohistochemical staining of spleens of mice used in the experiments related to DNP-poly [A], as follows:

FIGS. 8a1–8a2 normal mouse spleen at (1; left) 160× and (2; right) 1600×;

FIGS. 8b1–8b2 infected ($10^9$ virus particles) and untreated spleen at (1; left) 160× and (2; right) 1600×;

FIGS. 8c1–8c2 infected with $10^9$ virus particles for four months and treated 3× per week with 100 mg DNP-poly [A]/kg at (1; left) 160× and (2; right) 1600×; and FIGS. 8d1–8d2 uninfected but treated 3× per week with 100 mg DNP-poly [A]/kg at (1; left) 160× and (2; right) 1600×.

FIGS. 9a to FIG. 9d are a series of photographs of electrophoresis gels showing the results of RT-PCR assays on mice infected with MuLV and demonstrating the time course of the abolition of the virus in mice treated with a DNP-derivatized antisense oligoribonucleotide to the MuLV envelope protein.

FIG. 10 is diagram of a multifunctional retroviral inhibitor comprising nucleotide sequences complementary to two genes or gene transcripts (left) SEQ ID NO:5, shown in complementary base pairing to a portion of the mRNA of a retrovirus sequence (right). The attachment of DNP groups to nucleotide residues is arbitrarily assigned in FIG. 10 for the purpose of illustration only.

Figure 11:
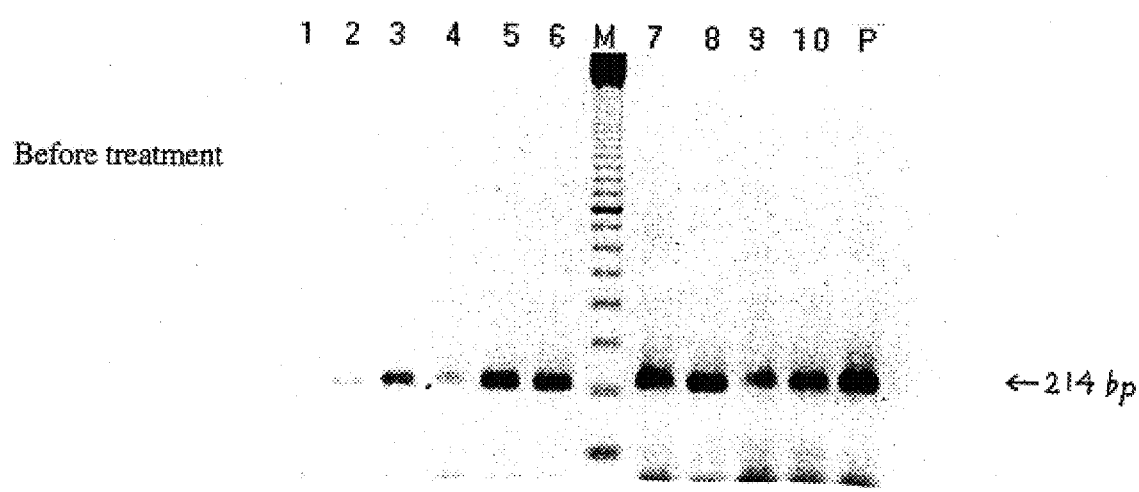

FIG. 11 is a photograph of an electrophoresis gel of PCR products derived from ducks infected with DHBV.

Figure 12A:
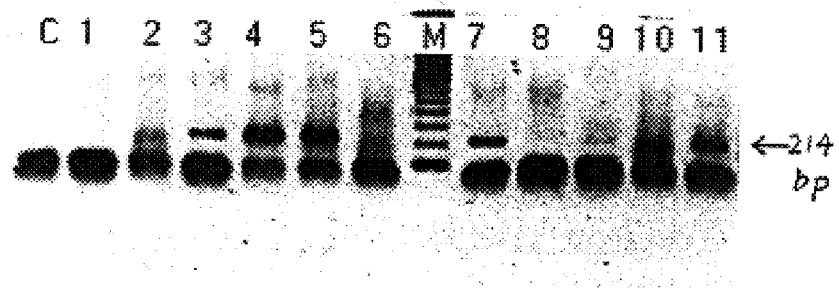
Figure 12B:
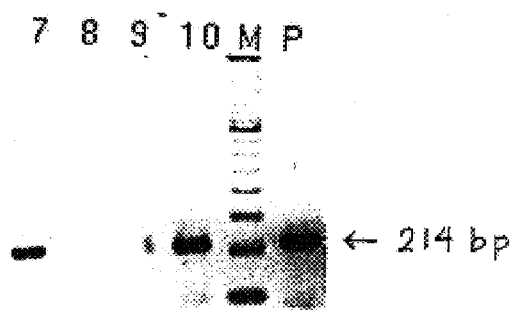

FIGS. 12a and 12b are photographs of two electrophoresis gels showing PCR transcripts of a DHBV gene after two weeks (FIG. 12a) of treatment, and 10 weeks after cessation of treatment (FIG. 12b) with an antisense inhibitor of this invention.

Figure 13A:
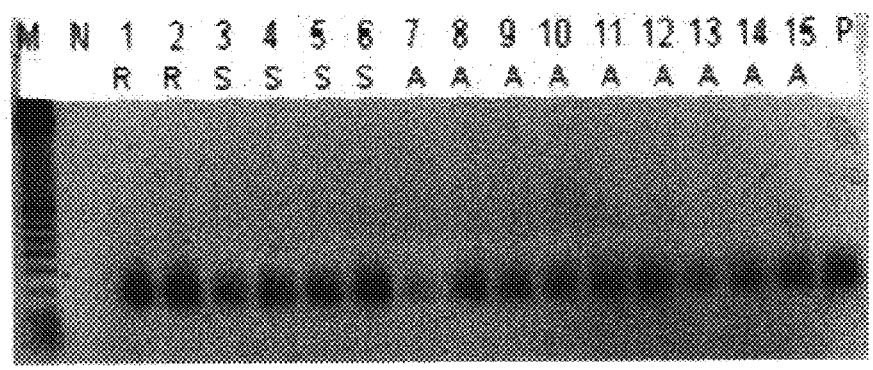
Figure 13B:
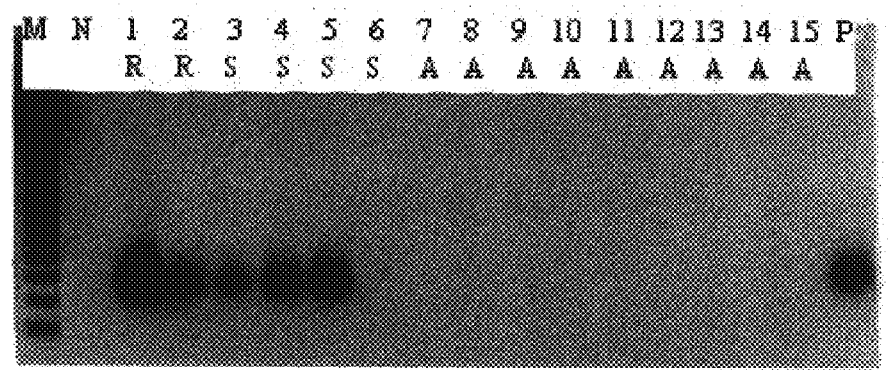
Figure 13C:
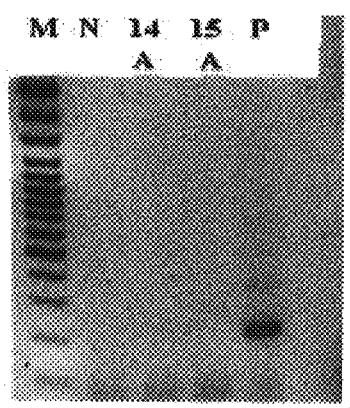

FIGS. 13a to 13c are photographs of electrophoresis gels of PCR products derived from ducks treated with antisense oligoribonucleotides of this invention directed against DHBV. FIG. 13a shows PCR products from ducks 15 days after inoculation with virus. FIG. 13b shows PCR products from ducks 15 days after treatment. FIG. 13c shows PCR products from ducks 8 months after treatment.

Figure 14:
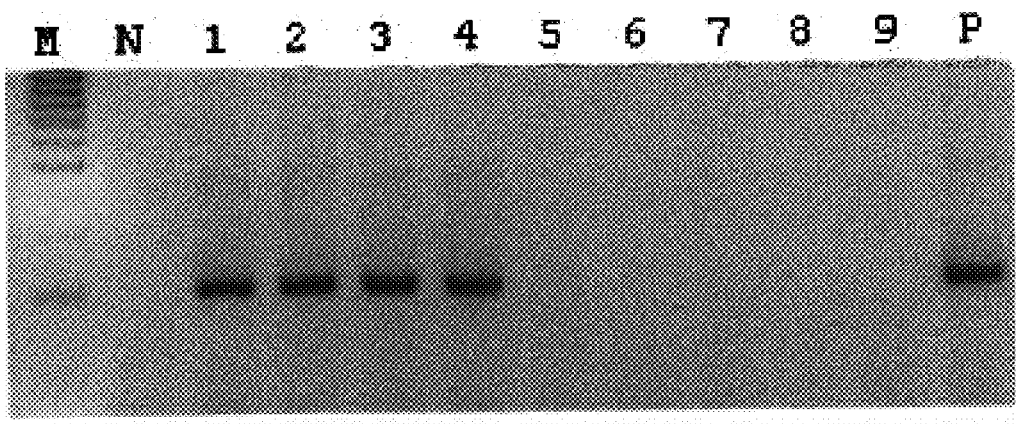

FIG. 14 show is a photograph of an electrophoresis gel of PCR products derived from the livers of ducks treated with antisense oligoribonucleotides of this invention directed against DHBV.

Figure 15:
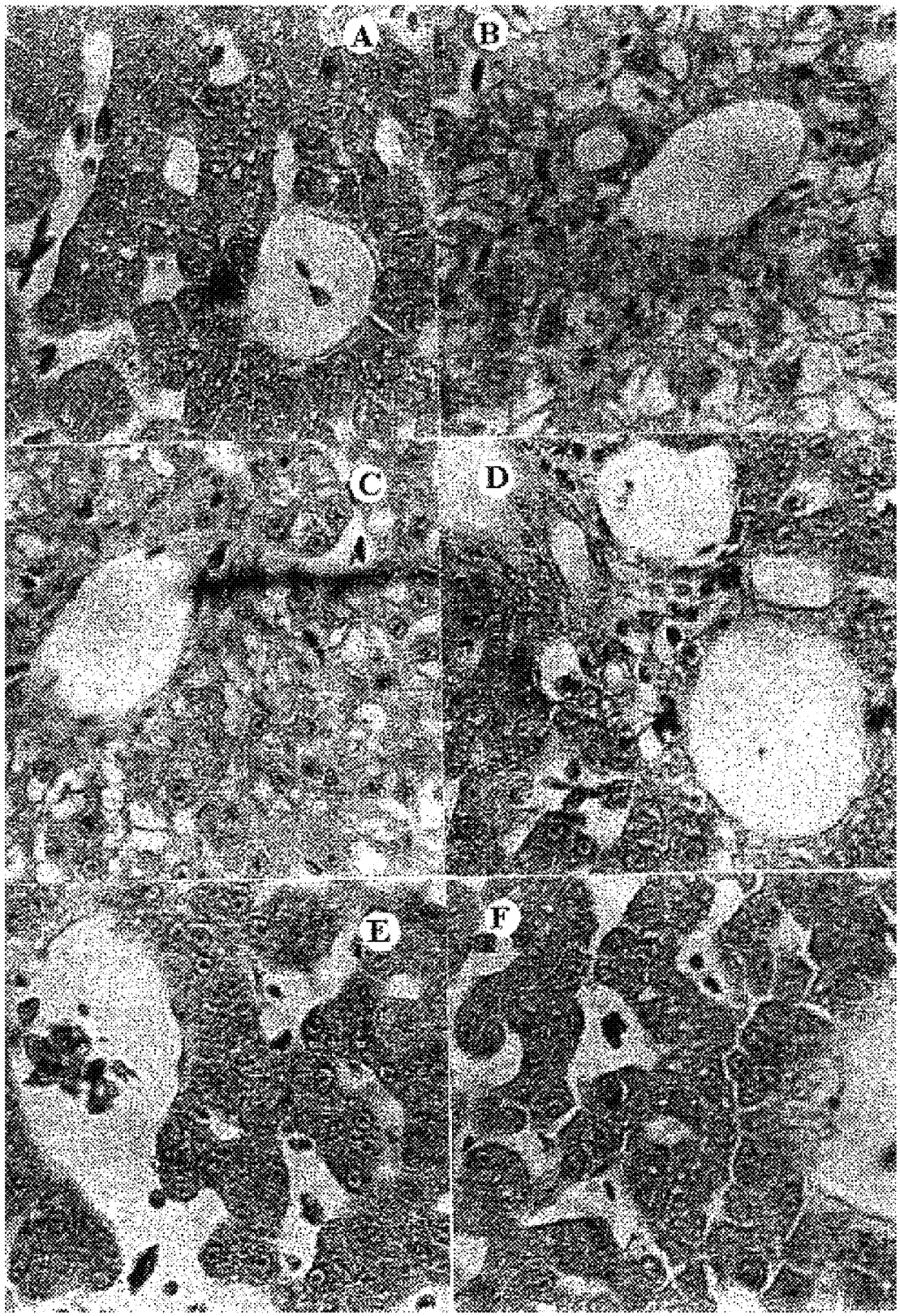

FIGS. 15a–15f are photographs of the livers of ducks, either untreated or treated with the oligoribonucleotides of this invention directed against DHBV. FIG. 15a shows the liver of an uninfected duck. FIG. 15b shows the liver of a duck infected with DHBV but not treated. FIGS. 15c, 15d, 15e, and 15f show the livers of ducks infected with DHBV and after treatment with antisense oligoribonucleotides directed against DHBV for increasing periods of time.

Figure 16:
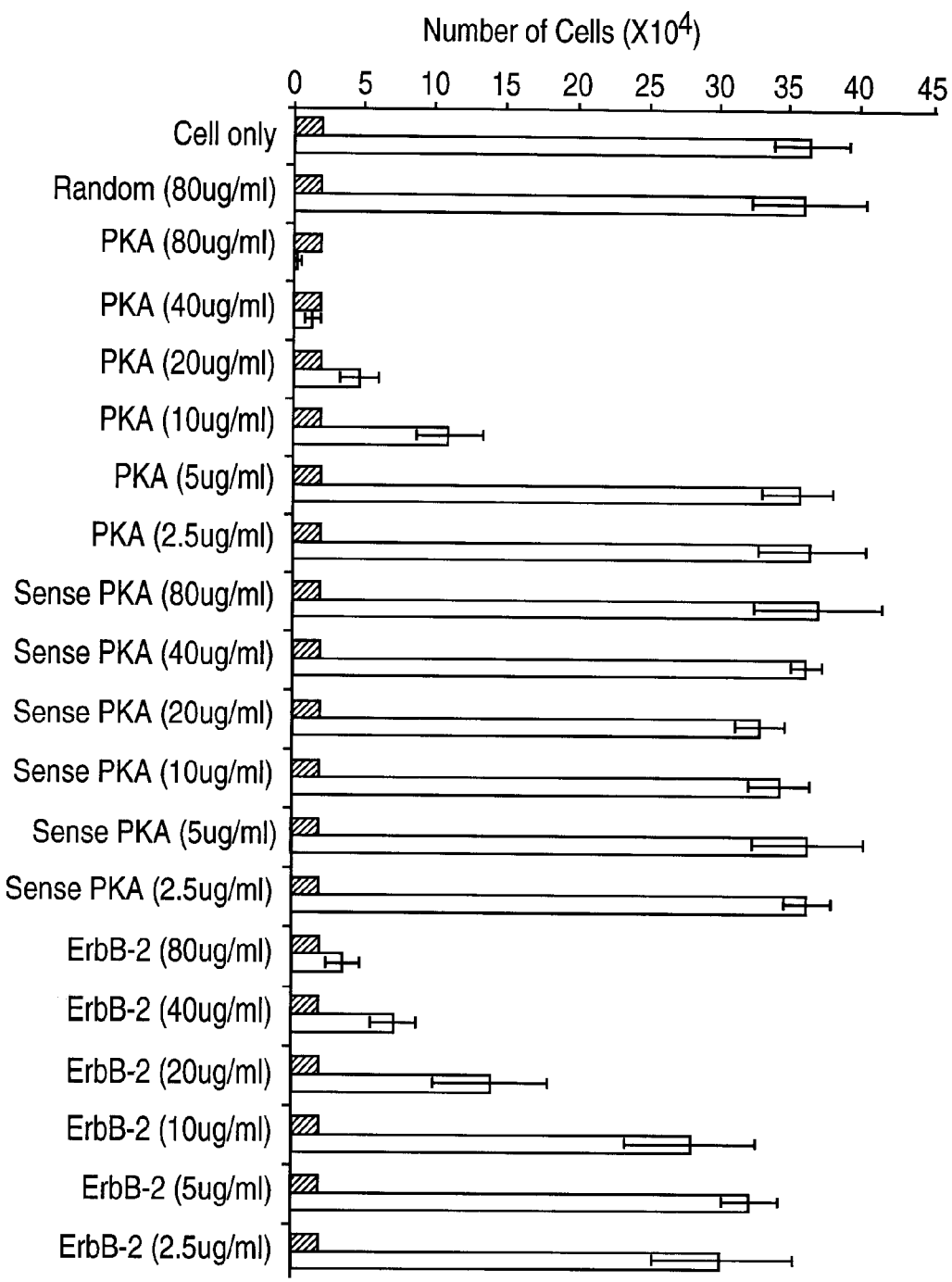

FIG. 16 is a graph of the results of an in vitro study of antisense oligoribonucleotides of this invention directed against RIα/PKA and/or erbB-2 genes in SK-Br-3 breast cancer cells.

Figure 17:
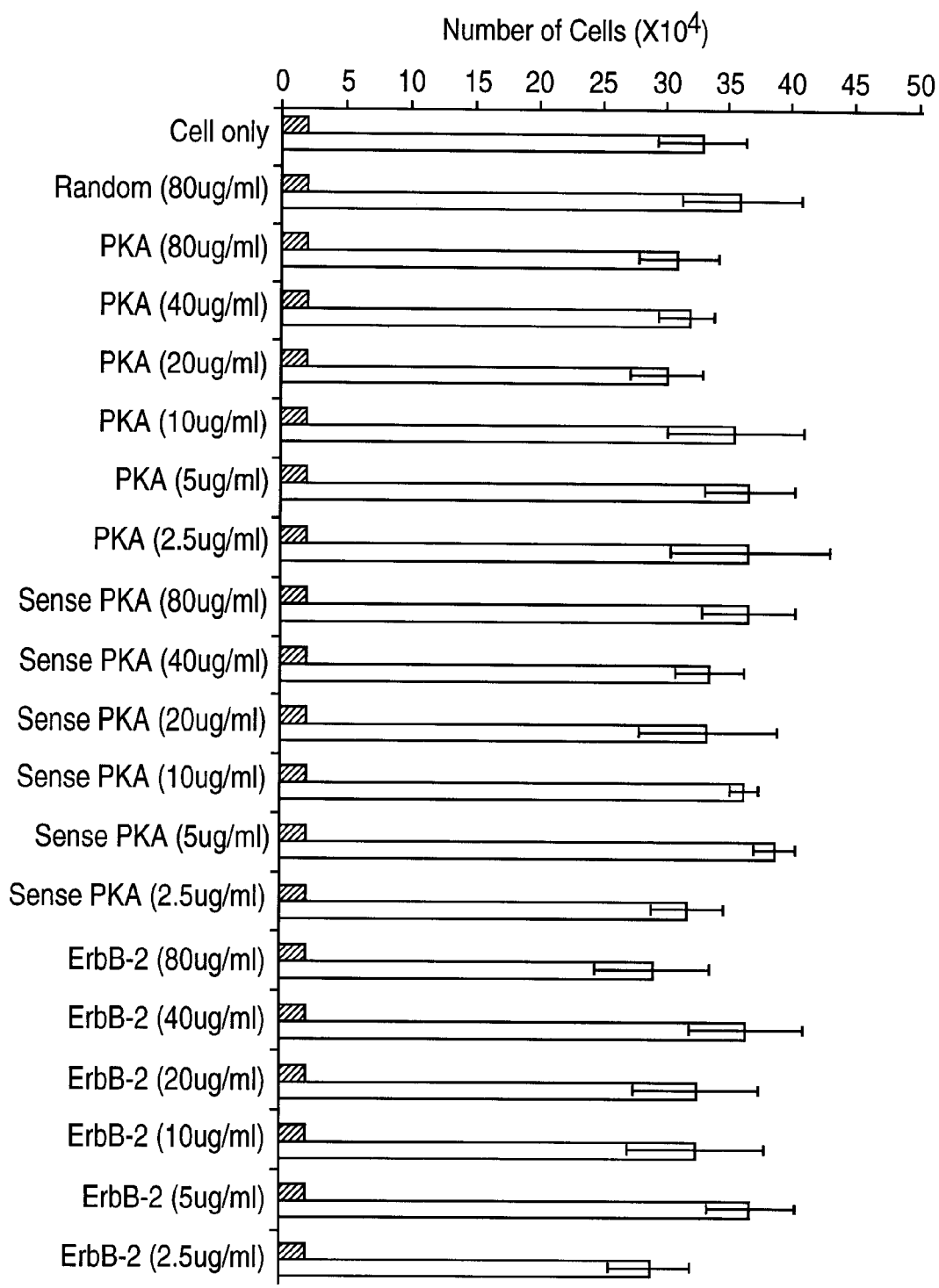

FIG. 17 is a graph of the results of an in vitro study of antisense oligoribonucleotides of this invention directed against RIα/PKA and/or erbB-2 genes in MAF-10A non-cancerous breast cells.

Figure 18:
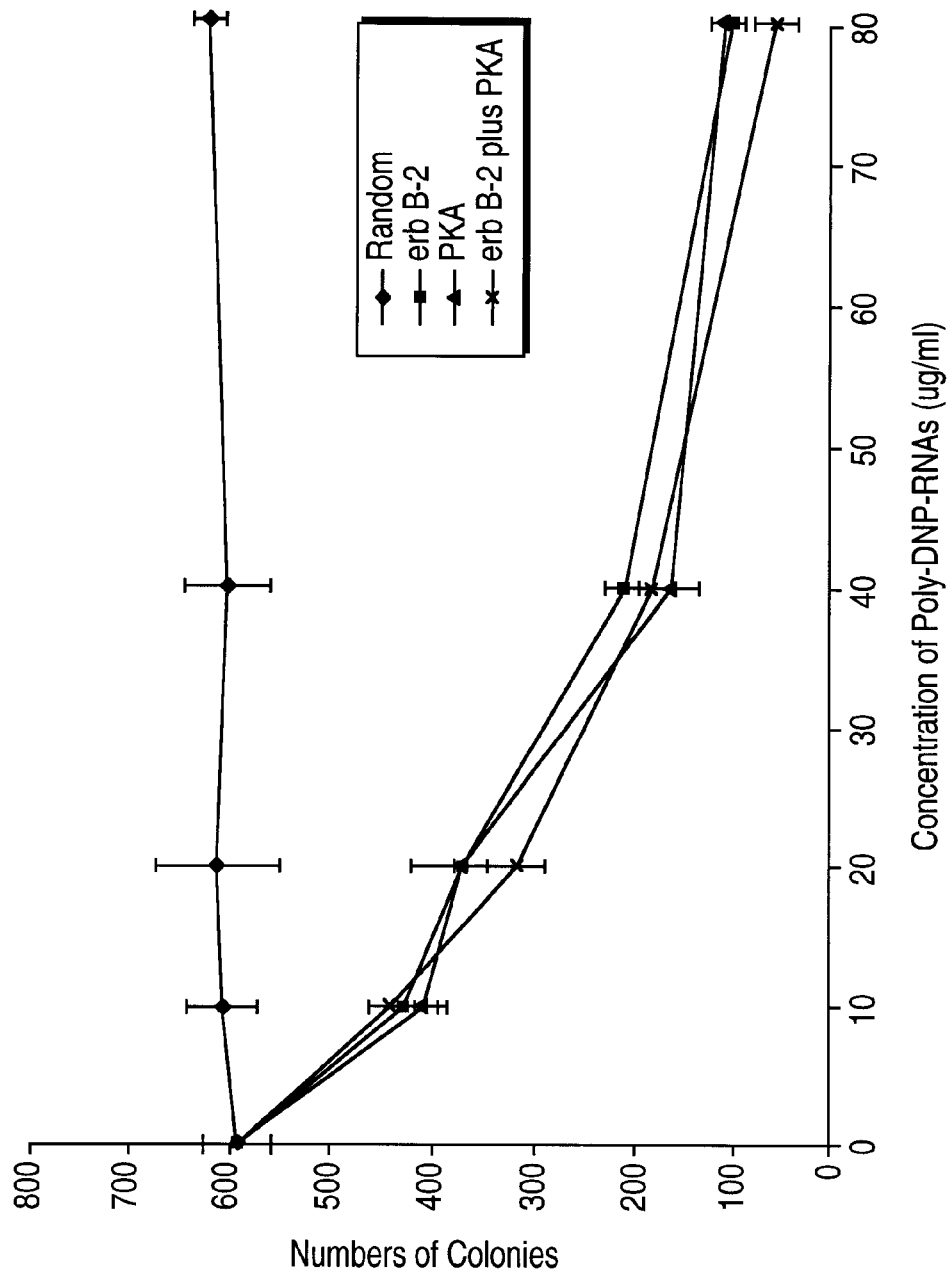

FIG. 18 is a graph of the effect of antisense oligoribonucleotides of this invention on colony formation of breast cancer cells grown in semi-solid medium.

Figure 19:
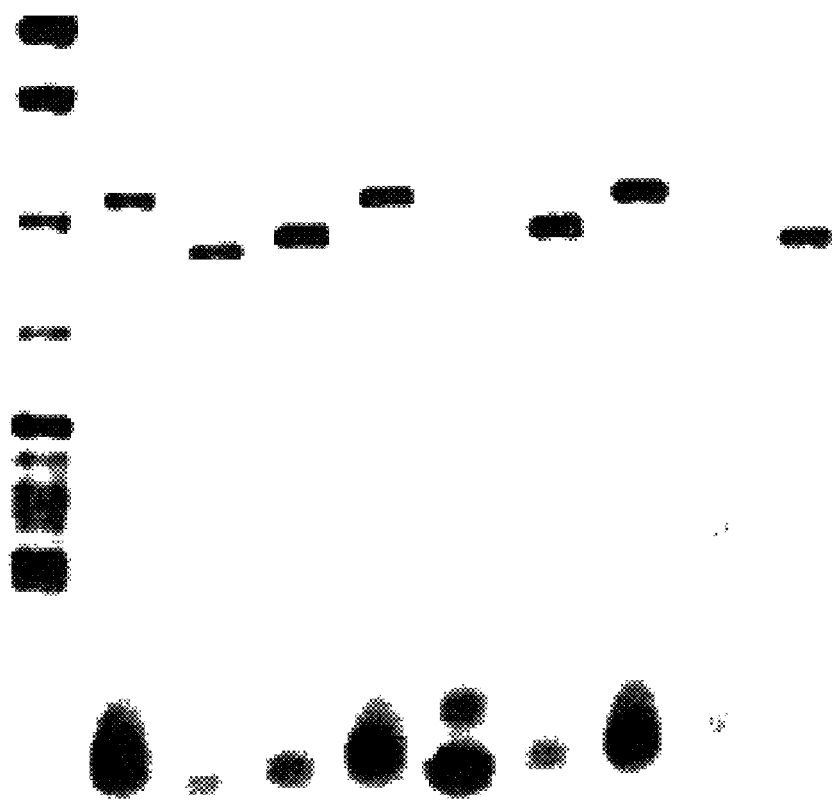

FIG. 19 is a photograph of an electrophoresis gel showing PCR products of SK-Br-3 breast cancer cells before or after treatment with oligoribonucleotides of this invention directed against RIα/PKA and/or erbB-2.

FIGS. 20a–20d are photographs of SK-Br-3 breast cancer cells (FIGS. 20a–20b) and non-cancerous breast cells, MAF-10A cells (FIGS. 20c–20d). Photographs on the left (1) are taken through a red filter and photographs on the right are taken through a green filter (2).

Figure 21:
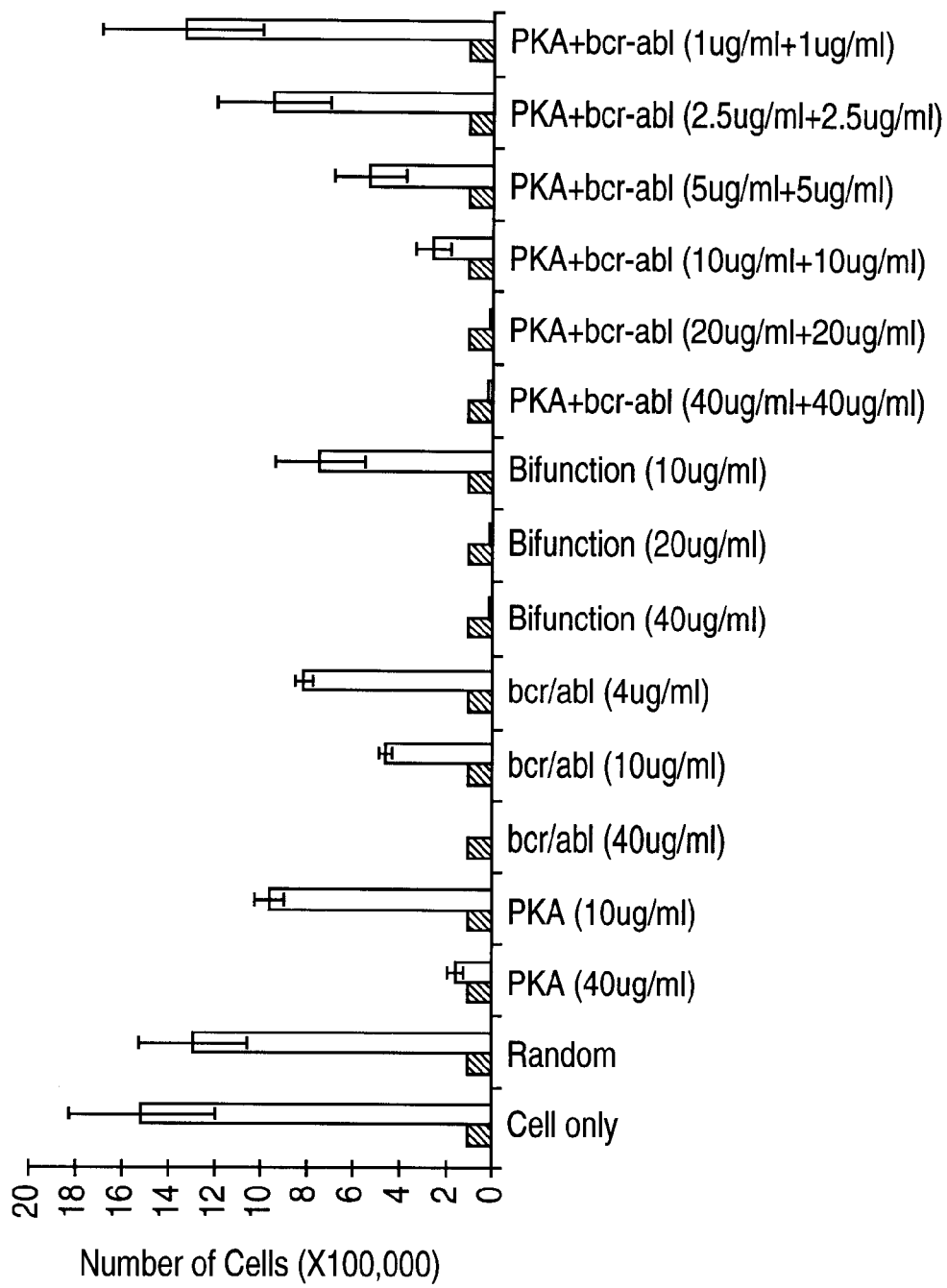

FIG. 21 is a graph of the results of a study of RIα/PKA and/or bcr-abl antisense oligoribonucleotides of this invention on the cancer cell line, BV173 cells.

FIG. 22 is a graph of the results of a study of RIα/PKA and/or bcr-abl antisense oligoribonucleotides of this invention on the formation of colonies of BV173 cells in semi-solid medium.

DETAILED DESCRIPTION OF THE INVENTION

In accordance with the present invention, it has been unexpectedly discovered that through the simple derivatization of antisense oligonucleotides at the 2'-O position with a hydrophobic carrier agent comprising a poly-substituted phenyl group, suitably, 2,4-dinitrophenyl groups or 3-fluoro-4,6-dinitrophenyl groups, the resulting derivatized antisense oligonucleotides are rendered substantially more membrane permeable and are extremely resistant to enzymatic degradation. In accordance with the invention, it is therefore possible to use "natural" oligonucleotides (i.e., those oligonucleotides formed from naturally occurring nucleotides). Beneficially, the use of these derivatized natural antisense oligonucleotides either improves or at least does not destabilize the hybridization of the antisense sequence with the sense RNA strand. This fact improves the therapeutic potential of any given antisense approach, making it possible to decrease the dose necessary to suppress gene expression.

Oligonucleotides derivatized in accordance with the invention withstand extreme conditions in which their underivatized brethren would completely fail. Further, oligonucleotides derivatized in accordance with the invention are exceptionally bioavailable and appear to pass through cell membranes in tissue culture as well as in vivo in mammals. In contrast, underivatized oligonucleotides are substantially less bioavailable. Ultimately, oligonucleotides derivatized in accordance with invention appear to be substantially nontoxic to cells and well tolerated in mammals and other animals.

As mentioned above, while natural oligonucleotides are preferably used in accordance with the invention, it is expected that virtually any oligonucleotide or oligonucleotide analogue containing a 2'-OH can be derivatized and used with similar benefits of enhanced membrane permeability and stability as natural oligonucleotides. Further, while it is not believed to be necessary, the derivatized oligonucleotides of the invention can be delivered using conventional delivery vehicles and agents that have been used in the art to enhance delivery of oligonucleotides, such as liposomes, cationic lipids, and the like.

In general, appropriate hydrophobic carrier agents in accordance with the invention have the following general structure:

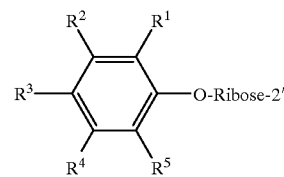

wherein $R^1$, $R^2$, $R^3$, $R^4$, and $R^5$ are independently H, $NO_2$, halide, linear or branched alkyl, linear or branched acyl, linear or branched alkylene, linear or branched O-alkyl, linear or branched O-acyl, linear or branched O-alkylene, linear or branched amido, linear or branched S-alkyl, linear or branched S-acyl, linear or branched S-alkylene, mono or disubstituted amine, linear or branched amido, linear or branched thioamido, phosphothionate, or phosphothioate. Preferably, no one of $R^1$, $R^2$, $R^3$, $R^4$, and $R^5$ exceeds 9 atoms excluding protons.

In a preferred embodiment, $R^1$ and $R^3$ are $NO_2$ and $R^2$, $R^4$, and $R^5$ are as above, as follows:

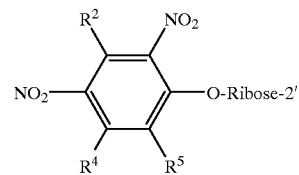

It will be appreciated that when $R^2$, $R^4$, and $R^5$ are H, the compound is DNP.

In another preferred embodiment, the $R^1$ and $R^3$ are $NO_2$, $R^2$ and $R^5$ are as described above, and $R^4$ is a halide (fluorine), as follows:

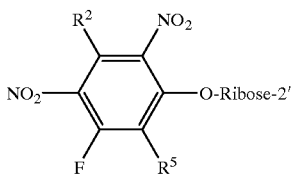

It will be appreciated that when $R^2$ and $R^5$ are H, the compound is FDNP.

In a preferred embodiment, the hydrophobic carrier agents of the present invention as described above are conjugated to oligonucleotides for the purpose of stabilizing and enhancing delivery of antisense oligonucleotides.

As used herein, the term "oligonucleotide" includes not only oligomers and polymers of the common biologically significant nucleotides, i.e., the nucleotides adenine ("A" or "a"), guanine ("G" or "g"), cytosine ("C" or "c"), thymine ("T" or "t") and uracil ("U" or "u"), but also include oligomers and polymers hybridizable to an RNA transcript of the particular gene of interest which may contain other nucleotides. Likewise, the term "oligonucleotides" may include oligomers and polymers wherein one or more purine or pyrimidine moieties, sugar moieties or internucleotide linkages is chemically modified. The term "oligonucleotide" is thus understood to also include oligomers which may not properly be designated as "oligonucleotides" because of modification of the internucleotide phosphodiester bond. Such modified oligonucleotides include, for example, the alkylphosphonate oligonucleotides, discussed below.

The term "phosphorothioate oligonucleotides" is defined as an oligonucleotide wherein one more of the internucleotide linkages is a phosphorothioate group,

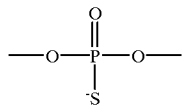

as opposed to the common phosphodiester group

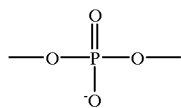

which is characteristic of unmodified oligonucleotides.

An "alkylphosphonate oligonucleotide" is defined as an oligonucleotide wherein one or more of the internucleotide linkages is an alkylphosphonate group,

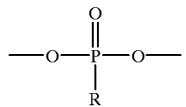

where R is an alkyl group preferably methyl or ethyl.

The term "gene RNA transcript" is defined herein as the RNA transcript encoding the protein of interest. It will be understood that a variety of methods for determining the level of a gene's expression are well-known to those skilled in the art. Such methods include, for example, reverse transcriptase polymerase chain reaction (RT-PCR) analysis.

The term "multifunctional inhibitor" is defined herein as an oligoribonucleotide or derivatized oligoribonucleotide that comprises different functional inhibitory characteristics, including either multiple antisense sequences and/or the capability of inhibiting multiple or different cellular functions, including, but not limited to inhibition of reverse transcriptase and inhibition of expression of DNA or translation of mRNA.

The term "regulatory domain" is defined herein as a portion of a gene which controls the expression of another portion of the same gene or another gene. The term "regulatory domain" also is defined herein as a portion of a gene or a gene transcript, which when hybridized to a complementary oligonucleotide, inhibits the transcription or translation of at least that portion of the gene.

The antisense oligonucleotides of the present invention may be synthesized by any of the known chemical oligonucleotide synthesis methods. Such methods are generally described, for example, in Winnacker *From Genes to Clones: Introduction to Gene Technology*, VCH Verlagsgesellschaft mhH (H. Ibelgaufts trans. 1987), the disclosure of which is hereby incorporated by reference in its entirety. Any of the known methods of oligonucleotide synthesis may be utilized in preparing the instant antisense oligonucleotides.

The antisense oligonucleotides are most advantageously prepared by utilizing any of the commercially available, automated nucleic acid synthesizers. One such device, the Applied Biosystems 380B DNA Synthesizer, utilizes β-cyanoethyl phosphoramidite chemistry. Further, many antisense oligonucleotides are commercially available. For example, Oligo Therapeutics, Inc. has a broad line of commercially available oligonucleotides and, further, provides contract manufacturing services for the preparation of oligonucleotides.

Since the complete nucleotide sequence of DNA complementary to many gene RNA transcripts are known, antisense oligonucleotides hybridizable with any portion of the particular gene transcript may be prepared by oligonucleotide synthesis methods known to those skilled in the art.

Prior work indicates that while any length oligonucleotide may be utilized in the practice of antisense therapeutics, sequences shorter than 10 to 12 bases may be less specific in hybridizing to the target gene RNA. Further, such sequences may be more easily destroyed by enzymatic digestion within and without cells. In addition, such sequences may be destabilized by enzymatic digestion. Hence, oligonucleotides having 10 to 12 or more nucleotides are preferred.

Prior work has also shown that long sequences, particularly sequences longer than about 40 nucleotides, may be somewhat less effective in inhibiting gene translation because of decreased uptake by the target cell. It is believed that the present invention is less susceptible to this problem owing to the coupling of the antisense oligonucleotide with the carrier groups. Nevertheless, oligomers comprising single antisense sequences of 10 to 50 nucleotides are suitable, sequences of 10–40 nucleotide residues are preferred, more preferably 12–30 nucleotide residues, most preferably 15–25 nucleotide residues. Thus, sequences of 15–25 nucleotide residues are most particularly preferred for the design of oligoribonucleotides with a single antisense sequence. However, multifunctional inhibitors comprising more than one antisense sequence can be longer than 25 nucleotides in length. In connection with the present invention, membrane permeability and stability to enzymatic degradation of derivatized oligonucleotides is essentially not a problem. Therefore, the choice of the length of any particular nucleotide sequence will revolve around the ability of the oligonucleotide to form a stable hybrid with the particular RNA transcript and the stability of the duplex hybrid to enzymatic degradation.

Additionally, multi-functional antisense inhibitors comprise oligoribonucleotides having two or more antisense sequences directed at the same gene or different genes. By way of example only, any oligoribonucleotide sufficiently long to substantially fill the cleft of the viral reverse transcriptase is an inhibitor of that enzyme. Therefore, any antisense oligoribonucleotide of sufficient length to substantially fill the cleft is an inhibitor of both viral reverse transcriptase and the specific gene to which the oligoribonucleotide is complementary. Such oligoribonucleotides are herein termed "bifunctional" inhibitors. Similarly, oligoribonucleotides comprising two different antisense sequences which are also of sufficient length to substantially fin the cleft of the viral reverse transcriptase can inhibit three functions, viral reverse transcriptase, and the two antisense targets. In this way, the transport of a single antisense oligoribonucleotide can provide several inhibitory functionalities into a cell.

Oligonucleotides complementary to and hybridizable with any accessible portion of the particular gene transcript can, in principle, be effective for inhibiting translation of the transcript, and capable of inducing the effects herein described. Such oligoribonucleotides are considered useful if they hybridize to the target gene or gene transcript in vitro or in vivo, or are capable of hybridizing to a gene or gene transcript under stringent hybridization conditions. By stringent conditions, we mean hybridization at 5–10° C. below the melting temperature of the oligonucleotide-gene or oligoribonucleotide-transcript complex, and using high concentrations of the oligoribonucleotide. Determination of the melting temperature can be found by referring to standard methods in the art, such as, by way of example only, Sambrook et al. Molecular Cloning: A Laboratory Manual, Second Edition, Cold Springs Harbor Laboratory Press (1989), incorporated herein fully by reference. It appears that translation is often most effectively inhibited by blocking the RNA at a site at or near the initiation codon. Thus, oligonucleotides complementary to the 5'-terminal region of the gene RNA transcript are often used. It is believed that secondary or tertiary structure which might interfere with hybridization is minimal in this region. Moreover, it has been suggested that sequences that are too distant in the 3'-direction from the initiation site may be less effective in hybridizing the RNA transcripts because of a "read-through" phenomenon whereby the ribosome is postulated to unravel the antisense/sense duplex to permit translation of the message. See, e.g., Shakin, *J. Biochemistry* 261:16018 (1986). Similarly, antisense oligonucleotides can additionally be directed to a site at or near a splice donor-acceptor sites. For example, in the case of basic fibroblast growth factor (bFGF), which contains two splice donor-acceptor sites, oligonucleotides can be directed to the splice donor-acceptor site 1 (codon 60) or splice donor-acceptor site 2 (codon 94–95). See Ensoli et al. WO 94/29,444.

Ensoli et al. point out that in respect of bFGF, it is preferable to utilize antisense oligomers that are complementary to one of the two splice donor-acceptor sites of the bFGF transcript, and, particularly the region including the first splice donor-acceptor site. In the case of other genes, it will be appreciated that useful antisense oligomers are not limited to that complementary to the sequences found in the translated portion of the RNA transcript, but also includes oligomers complementary to nucleotide sequences including the initiation codon, or contained in, or extending into, the 5'-and 3'-untranslated regions.

The S1 nuclease assay procedure of *Molecular Cloning*, 2nd edition (Sambrook et al., Eds. 1989), pages 7.66–7.70 (incorporated herein by reference) can be utilized to map the location of cap sites using RNA isolated from cell lines expressing the gene. The location of the longest clearly visible band can be located as indicative of the putative principle cap site. S1 protection assays may also be used to reveal faint bands in addition to the main band corresponding to the cap site. These other bands may represent rare or unstable transcripts of the gene. Multiple sites of transcription initiation are not uncommon in genes which lack a perfect TATAA box. The nucleotide sequence of the RNA transcript 5'-terminus beginning with the cap nucleotide may be readily established, and antisense oligonucleotides complementary and hybridizable thereto may be prepared.

The oligonucleotide employed may represent an unmodified oligonucleotide or an oligonucleotide analog. Thus, oligonucleotides hybridizable to the particular gene RNA transcript finding utility according to the present invention include not only oligomers of the biologically significant native nucleotides but also oligonucleotide species which have been modified for improved stability and/or lipid solubility. For example, it is known that enhanced lipid solubility and/or resistance to nuclease digestion results by substituting an alkyl or alkoxy group for a phosphate oxygen in the internucleotide phosphodiester linkage to form an alkylphosphonate oligonucleotide or alkylphosphotriester oligonucleotide. However, such alkyl substituted oligonucleotides suffer from the problem that, owing to steric and electrochemical interactions, may not hybridize as well as natural oligonucleotides. The phosphorothioates are also stable to nuclease cleavage and soluble in lipids. They may be synthesized by known automatic synthesis methods. Phosphorothioates, however, have been identified as possessing similar potential hybridization problems as the alkyl substituted oligonucleotides. Non-ionic oligonucleotides such as alkyl substituted and phosphorothioates, are characterized by increased resistance to nuclease hydrolysis and/or increased cellular uptake, while retaining the ability to form reasonably stable complexes with complementary nucleic acid sequences. The alkylphosphonates in particular, are stable to nuclease cleavage and soluble in lipid. The preparation of alkylphosphonate oligonucleotides is disclosed in U.S. Pat. No. 4,469,863. The methylphosphonates, in particular, are preferred. Methylphosphonate oligomers can be prepared by a variety of methods, both in solution and on insoluble polymer supports (Agrawal et al. *Nucl. Acids Res.* 6:3009–3024 (1979)).

The most efficient procedure currently known for preparation of methylphosphonate oligonucleotides involves use of 5'-O-dimethoxytrityldeoxynucleotide-3'-O-diisopropylmethylphosphoramidite intermediates, which are similar to the methoxy or β-cyanoethyl phosphoramidite reagents used to prepare oligodeoxyribonucleotides. The methylphosphonate oligomers can be prepared on controlled pore glass polymer supports using an automated DNA synthesizer (Sarin et al. *Proc. Natl. Acad. Sci. USA* 85:7448–7451 (1988)).

Resistance to nuclease digestion may also be achieved by modifying the internucleotide linkage at both the 5' and 3' termini with phosphoroamidites according to the procedure of Dagle et al. *Nucleic Acids Res.* 18:4751–4757 (1990). Suitable nucleotide analogues for preparation of the antisense oligonucleotides described herein include but are not limited to the ethyl or methyl phosphonate analogues disclosed in U.S. Pat. No. 4,469,863.

Phosphorothioate oligonucleotides contain a sulfur-for-oxygen substitution in the internucleotide phosphodiester bond. Phosphorothioate oligonucleotides combine the properties of reasonably effective hybridization for duplex formation with substantial nuclease resistance, while retaining the water solubility of a charged phosphate analogue. The charge is believed to confer the property of cellular uptake via a receptor (Loke et al. *Proc. Natl. Acad. Sci. USA* 86:3474–3478 (1989)).

Phosphorothioate modified oligodeoxynucleotide are described by LaPlanche et al. *Nucleic Acids Research* 14:9081 (1986) and by Stec et al. *J. Am. Chem. Soc.* 106:6077 (1984). The general synthetic method for phosphorothioate oligonucleotides was modified by Stein et al. *Nucleic Acids Res.* 16:3209–3221 (1988), so that these compounds may readily be synthesized on an automatic synthesizer using the phosphoramidite approach. Also, additional modifications have been added by Zon et al. Zon et al. *Anti-Cancer Drug Design* 6:539–568 (1991); Zon et al. *Oligonucleotides and Analogues: A Practical Approach*, F. Eckstein, Ed. (Oxford University Press, Oxford, England), pp. 87–108 (1991)). See also Stec et al. U.S. Pat. No. 5,151,510.

Furthermore, recent advances in the production of oligoribonucleotide analogues mean that other agents may also be used for the purposes described here, e.g., 2'-O-methylribonucleotides (Inove et al. *Nucleic Acids Res.* 15:6131 (1987)) and chimeric oligonucleotides that are composite RNA-DNA analogues (Inove et al. *FEBS Lett.* 215:327 (1987)).

In general, the antisense oligonucleotides of the present invention will comprise a sequence which is completely complementary to the target portion of the message from the gene. Absolute complementarity is not however required, particularly in larger oligomers. Thus, reference herein to a "nucleotide sequence complementary to at least a portion of the RNA transcript" of a particular gene does not necessarily mean a sequence having 100% complementarity with the transcript. In general, any oligonucleotides having sufficient complementarity to form a stable duplex with RNA of the gene or the gene itself is suitable.

Stable duplex formation depends upon the sequence and length of the hybridizing oligonucleotide and the degree of complementarity with the target region of the gene or the message from the gene. Generally, the larger the hybridizing oligomer, the more mismatches that can be tolerated. One skilled in the art can readily determine the degree of mismatching that can be tolerated between any given antisense oligomer and the target message from the gene sequence, based upon the melting point, and therefore the stability, of the resulting duplex.

While oligonucleotides capable of stable hybridization with any region of the message for a particular gene are within the scope of the present invention, oligonucleotides complementary to a region including the initiation codon or a splice donor-acceptor site are believed particularly effective.

Earlier work performed and overseen by the inventor related to FDNP- and DNP-poly[A] oligonucleotides for use in the treatment of viral infections, and, particularly the treatment of HIV. See U.S. Pat. No. 5,496,546, filed on Feb. 23, 1994, which is a continuation-in-part of U.S. patent application, Ser. No. 08/022,055, filed on Feb. 24, 1993, the disclosures of which are hereby incorporated by reference in their entirety. That work originated based on the long-standing practice of labeling nucleophilic groups of proteins with Sanger's reagent 1-fluoro-2,4-dinitrobenzene. Thus, poly[A] was reacted with electrophilic 1,5-difluoro-2,4-dinitrobenzene (DFDNP) or 1-fluoro-2,4-dinitrobenzene (FDNB) to derivatize poly[A] at its 2'-OH positions through ether linkages. See Chuan and Wang, *J. Biol. Chem.* 263:13003 (1981), the disclosure of which is incorporated herein by reference in its entirety. These electrophilic groups serve to react with and to bind to nucleophilic groups in the active site cleft of reverse transcriptase, thus blocking its action. The structure of the resulting polymer derivative, designated as FDNP-poly[A], is represented by a structure shown below with general formula: $M_n(FDNP)_m X_i[A]_n$ where:

$[A]_n$ = polyadenylic acid (5') with $n$ adenylic acid residues, $FDNP$ = 3-fluoro-4,6-dinitrophenyl groups, attached covalently to $m$ of the $n$ 2'-OH groups of $[A]_n$ via ether linkage, $X$ = an acyl group, $i$ = 0 or 1, $M$ = a caution selected to provide a desired degree of solubility for the composition, and has one of the generic structures:

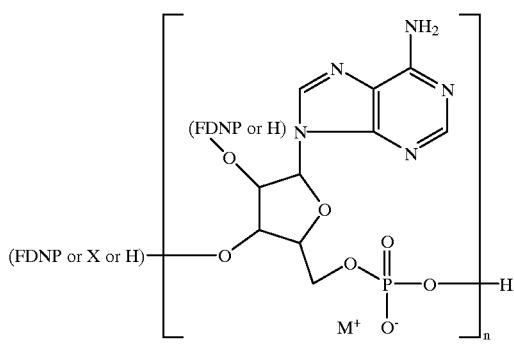

or

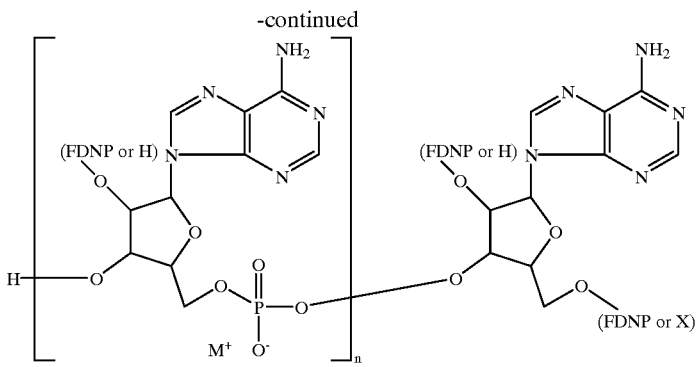

It was further discovered that DNP-poly[A] is also effective in inactivating reverse transcriptases and ribonucleases. Indeed, while the action of DNP-poly[A] is not irreversible it was found that with 1 DNP-group per 1.5 adenine residues, the latter is about twelve times as effective (i.e., is equally effective at one-twelfth the dosage) as is FDNP-poly [A]. The polymer derivative, designated as DNP-poly[A], is represented by a structure shown below with general formula: $M_n(DNP)_m X_i[A]_n$ where:

[A]$_n$ = polyadenylic acid (5′) with $n$ adenylic acid residues,

DNP = 2, 4-dinitrophenyl groups, attached covalently to $m$ of the $n$ 2′-OH groups of [A]$_n$ via ether linkage, X = an acyl group, $i$ = 0 or 1, M = a caution selected to provide a desired degree of solubility for the composition, and has one of the generic structures:

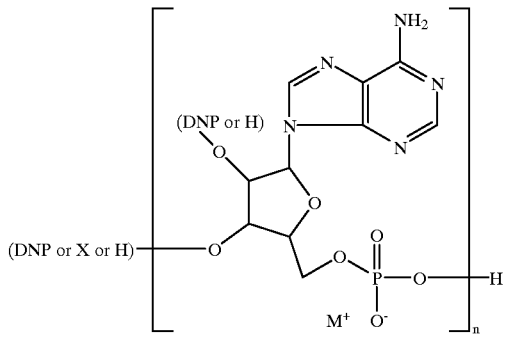

or

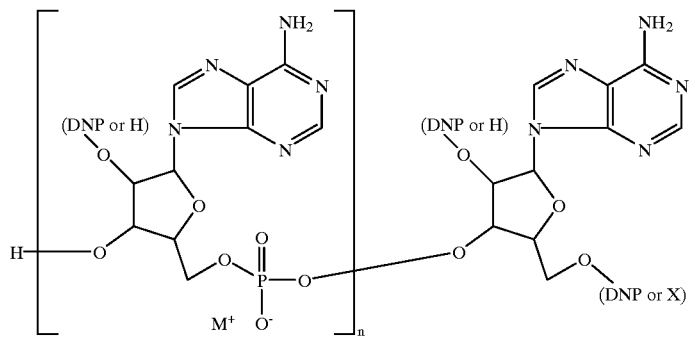

In both cases, n is sufficiently large so that the Y-poly[A] (where Y=DNP, FDNP or where some Y are DNP and others are FDNP) substantially completely fills the active site cleft of the RNA-virus RT to effectively inactivate the reverse transcriptase and/or can effectively inactivate ribonuclease. Generally it is preferred that n be relatively large, suitably 20 or greater and preferably 25 or greater. Actual experiments are set forth below for a relatively higher molecular weight Y-poly[A](h-$M_r$), n≈270, m≈69, $M_r$≈1.1×10$^5$ (where $M_r$ represents molecular weight) and for a relatively lower molecular weight Y-poly[A](l-$M_r$), n≈28, m≈9, $M_r$≈1.2×10$^4$.

FDNP groups are generally attachable to the poly[A] to provide a ratio of FDNP group to [A] of no more than about 1:4. DNP groups are attachable to the poly[A] to provide a considerably higher ratio of about 1:1.5. Mixed FDNP/DNP poly[A] polymers can also be formed. Generally, 1,3-difluoro-2,4-dinitrobenzene (DFNB) will first be reacted with the poly[A] to provide a ratio of FDNP to [A] of from about 1:4 to about 1:10. Then, the product will be reacted with 1-fluoro-2,4-dinitrobenzene (FDNB) so that the resulting composition will have an overall ratio of FDNP plus DNP groups to [A] which is as high as can be attained, generally of greater than 1:4, preferably greater than 1:2. Similar ratios of the hydrophobic carrier agent to nucleotide sequence are contemplated in accordance with the invention.

The cation, M, can be any cation which will provide a sufficient concentration of the composition to accomplish a desired purpose. While the potassium salt is preferred, ammonium, rubidium, cesium, among other salts can be utilized in its place.

Since the Y-poly [A] polymers were designed to inactivate all reverse transcriptases, they can be utilized for the treatment of virtually any diseases caused by RNA-viruses, e.g., adult T-cell leukemia/lymphoma, hepatitis A, C, D and E, influenza, parainfluenza, infant bronchiolitis and pneumonia, common cold, measles, mumps, etc. Thus, diseases caused by, by way of non-limiting example, the RNA-viruses HTLV (adult T-cell leukemia/lymphoma virus), HAV (Hepatitis A virus), HAC (hepatitis C virus), HDV Hepatitis D virus, including duck hepatitis B virus, DHBV), HAC (Hepatitis E virus), HEV (influenza virus), parainfluenza virus, RSV (respiratory syncytial virus), common cold causing coronavirus and rhinovirus, measles virus and mumps virus can be controlled by use of the Y-poly [A] compounds.

It has unexpectedly been discovered in accordance with the present invention that highly variable sequences of polynucleotides can be derivatized in a similar manner to poly [A]. Moreover, when derivatized with a hydrophobic carrier agent in accordance with the present invention, such as DNP or FDNP, such oligonucleotides are readily available to cells and are stable. This discovery provides another route to the treatment of diseases such as the foregoing, and many others, through enhanced delivery of highly stable oligonucleotides for antisense applications, among others. Thus, in accordance with the present invention, another approach to RNA-virus mediated or caused diseases, as well as to treating cancer is provided and such diseases can be controlled by use of derivatized polynucleotides in accordance with the invention.

Derivatized Antisense Oligonucleotides

As will be appreciated the antisense oligonucleotides of the present invention possess a structure similar to those illustrated above for poly [A], with the exception that, instead of having only adenine groups, the compounds possess the sequences of the individual nucleotides. It will also be appreciated that antisense oligonucleotides derivatized in accordance with the invention possess both the enhanced membrane permeability and resistance to enzymatic degradation that is observed with derivatized poly[A]. In addition, however, the presence of the antisense sequence enables highly specific action of the compositions of the invention on particular genes. That is to say that while derivatized poly [A] appears to possess a general action on reverse transcriptases, derivatized antisense oligonucleotides in accordance with the present invention have very specific action on whatever gene they are designed to hybridize, including viral genes and cancer genes.

In the disclosure that follows, several experiments are described that have been conducted relating to the Moloney murine leukemia virus (MuLV). First, work performed by or under the direction of the inventor has demonstrated that DNP-poly [A] is effective in the treatment of MuLV in mammals. Such work provides a back drop for recent work related to the preparation and effectiveness of antisense oligonucleotides, where it has been demonstrated that a DNP derivatized antisense oligonucleotide is effective to block the synthesis of the MuLV envelope protein results in abrogation of MuLV infection in mammals.

The MuLV virus is originated from Sarcoma 37. It is a transplantable connective tissue neoplasm of mice. Moloney, J. B "Biological studies on a lymphoid leukemia virus extracted from sarcoma 37.1. Origin and introductory investigations" J. Natl. Cancer Inst. 24:933–951 (1960), the disclosure of which is hereby incorporated by reference. It has been reported to produce a generalized lymphocytic neoplasm in mice within a short period (Dunn et al. "Pathogenesis of virus induced leukemia in mice" J. Nat. Cancer Inst. 26:382 (1961); Dmochowski et al. "Electron microscopic studies of rat leukemia induced with mouse leukemia virus" Proc. Soc. Exp. Biol. Med. 110:504–508 (1962), the disclosures of which are hereby incorporated by reference) and is specific with regard to age, strain and species that are susceptible to infection. Both MuLV and HIV belong to the group of (−) RNA viruses known as retroviruses which replicate through a DNA intermediate.

Since HIV is believed to be the causative agent of AIDS, arresting its replication has been the focus of much research. Current approved anti-HIV drugs AZT, ddI, and ddC serve as inhibitor and/or chain terminators of the RT reaction (Furman et al. "Phosphorylation of 3'-azido-3'-deoxythymidine and selective interaction of the 5'-triphosphate with Human Immunodeficiency Virus Reverse Transcriptase" Proc. Natl. Acad. Sci. USA 83:8333–8337 (1986); St. Clair et al. "3'-azido-3'-deoxythymidine triphosphate as an inhibitor and substrate of purified Human Immunodeficiency Virus Reverse Transcriptase" Antimicrobial Agents and Chemotherapy 31:1972–1977 (1987); Huang et al. "Selective action of 3'-azido-3'-deoxythymidine-5'-triphosphate on viral reverse transcriptases and human DNA polymerases" J. Biol. Chem. 265:11914–11918 (1990), the disclosures of which are hereby incorporated by reference). However, the virus is able to mutate in such a way that it is able to elude these drugs.

DNP-poly [A] was previously found to be an effective inhibitor of the reverse transcriptases from HIV-1, HIV-2, AZT and Nevirapine resistant strains of HIV as well as from MuLV in subnanomolar range in vitro (Kang, I and Wang, J. H. "Design of Structure-based Reverse Transcriptase Inhibitors" J. Biol. Chem. 269:12024–12031 (1994), the disclosure of which is hereby incorporated by reference). It is of great interest to find out the effect, if any, of this molecule on the progression of retroviral disease induced by the retrovirus. Below, the inhibitory effects of DNP-poly [A] and DNP derivatized antisense oligonucleotides on murine leukemia virus and on the MuLV-induced disease in Balb/c mice are described.

Moreover, the oligoribonucleotides of this invention can be used to decrease the expression of oncogenes and thereby decrease the growth of cancer cells which rely upon oncogene expression for their phenotypic and pathological properties.

Therapeutic Advantages of DNP-Derivatized Antisense Oligoribonucleotides

Antisense therapies in accordance with the invention provides a highly efficacious form of therapy compared to conventional antisense oligonucleotides. Naturally occurring oligonucleotides and oligoribonucleotides suffer from two major and distinct disadvantages. First, they are poorly soluble in cell membranes, making them poorly transported into cells and therefore attain access to the interior metabolic machinery of the cells only with great difficulty. To overcome this disadvantage, prior art oligonucleotides have been modified at the phosphodiester backbone by the addition of lipophilic residues such as thioate residues, thereby resulting in phosphothioate (PS) oligonucleotides. Many studies using PS-ODNs have been carried out with limited success. PS-ODNs are toxic to cells.

Further, the methods of manufacturing conventional oligonucleotides using solid-state synthesis suffers from the problem of heterogeneous stereospecificity. The conventionally manufactured phosphorous-derivatized oligonucleotides in that prior art oligonucleotides have chiral phosphorous atoms as part of the backbone of the oligonucleotide. This is because the PS derivatization occurs at the phosphodiester backbone, which has two configurations. Thus, there are two configurations in which the thioate residue may be linked to the phosphorous atom. Therefore, there are two possible stereoisomers at each chiral center of the phosphodiester bond, Rp and Sp. Because every phosphorous atom of prior art derivatized nucleotides has these two stereoisomers, the total number of different stereoisomers for an oligonucleotide of n residues in length is $2^n$. Thus, for an oligonucleotide containing 10 nucleotides, the total number of stereoisomers is $2^{10}$, or 1024. For an oligonucleotide 20 residues in length, there are over $10^6$ stereoisomers synthesized. For an oligonucleotide 40 nucleotides in length, there are over $10^{12}$ stereoisomers.

The melting temperature of a sense/antisense duplex of oligonucleotide reflects the tightness of their binding to each other. Tighter binding is reflected in a higher melting temperature, and weaker binding is reflected in a lower melting temperature. Thus, the duplex of pure stereoregular Rp PS-DNA has a higher melting temperature than that of synthetic PS-DNA, because Rp SP-DNA binds more tightly to native DNA or RNA than does the mixture of Rp plus Sp PS-DNAs. Moreover, a mixture of derivatized oligonucleotides synthesized according to the prior art methods has unpredictable ratios of Sp and Rp stereoisomers. Thus, a mixture of oligoribonucleotides made using prior art methods will have a melting temperature that is unpredictable because the ratio of Sp and Rp stereoisomers is unpredictable. It is therefore not surprising that synthetic PS-DNAs lack the specificity expected solely based upon the nucleotide base sequences of the oligonucleotides. For the same reasons, synthetic methylphosphonates (Miller et al., *Antisense Research and Applications* (Crooke, S. T. and Lebleu, B., Eds., pp: 189–203, CRC Press (1993)) will also be a mixture of $2^n$ stereoisomers and hence lack specificity.

Therefore, the concentration of the most tightly binding stereoisomer in such a heterogeneous mixture of $2^{10}$ nucleotide stereoisomers is only 1/1024 of the total concentration of the oligonucleotide present. Similarly, for oligonucleotides containing longer sequences, there are correspondingly more stereoisomers, and consequently, the concentration of the most effective oligonucleotide is reduced further. The poor specificity and efficacy of conventional phosphorothioate (PS) ODNs is partly due to the stereochemical heterogeneity.

The oligonucleotides of this invention, which can be derived from stereo homogeneous un-derivatized stereoisomers, can be made without chiral phosphorous atoms, and therefore, have no opportunity to for stereoisomers to form during the synthesis of derivatized oligonucleotides. Therefore, this aspect of the invention results in homogeneous stereoisomers of derivatized oligonucleotides, and thereby eliminates the above-discussed hybridization unpredictability due to stereochemical heterogeneity. For example, poly-DNP-poly [A] hybridizes with oligo-dT perfectly, with a melting temperature even tighter than the hybrid of poly [A] and oligo-dT (Kang and Wang, *J. Biol. Chem.* 269: 12023–12031 (1994)). The derivatized phenyl residues of this invention do not interfere with the base-paring in the hybrid, and the hybridization with mRNA can prevent programmed protein synthesis. According to this invention, many derivatized RNAs have been made and tested on target systems which include MuLV-infected mice, DHBV-infected ducks and in human breast cancer cell cultures. For each system, we found that the antisense oligoribonucleotides of this invention at sufficient dosage were 100% effective, but the control random sequences at the same dosage were 100% ineffective.

EXAMPLES

The following examples are intended to illustrate some features of this invention and are not intended to be exhaustive.

Example I

Inhibition of RNases by DNP-Poly A

To determine whether DNP-poly(A) is resistant to hydrolysis by ribonucleases (RNases), a series of experiments were performed in which the hydrolysis of radiolabeled poly(A) was measured in the absence and presence of DNP-poly(A). If DNP-poly(A) is resistant to hydrolysis, then DNP-poly(A) should inhibit the degradation of radiolabeled poly(A) by competitive inhibition of the nucleases responsible for the degradation of poly(A).

The inhibition of RNases by DNP-poly(A) was studied using methods described fully in Rahman et al. *Analytical Chem.* 68:143–138 (1996), hereby incorporated filly by reference. For each RNase assay, 10 $\mu$l of 0.1 M Tris-HCl (pH 7.0), 25 $\mu$l of 96 nM [$^3$H] poly(A) in 0.1 M Tris-HCl (pH 7.0), and 25 $\mu$l of RNase±inhibitor solution. The RNases studied included RNase A, B, S, T1, T2, and phosphodiesterases I and II. For each type of RNase, the enzyme concentration was fixed but the inhibitor concentration in different samples varied. The enzyme was pre-incubated with the inhibitor for 5 min at 37° C. before the reaction was started by the addition of radioactive substrate. After further incubation for 40–70 minutes, the reaction was terminated by the addition of 100 $\mu$l of 1% BSA solution and 600 $\mu$l of cold 12% trichloroacetic acid. The tubes containing the reaction mixtures were placed in crushed ice for 20 minutes and subsequently centrifuged for 20 minutes at 13,000 rpm. A 500 $\mu$l aliquot from each supernatant was mixed with 10 ml of scintillation cocktail and counted on a scintillation counter. Controls were run without inhibitor and without enzyme, respectively.

Using [3H] poly(A) as a substrate, we found that each RNase studied degraded the radiolabeled poly(A), and that DNP-poly(A) inhibited all of the RNases tested including RNase A, B, S, T1, T2, and phosphodiesterases I and II. In each determination, 5 $\mu$M of RNase B was pre-incubated with DNP-poly(A) for 5 minutes at 37° C. and then assayed as described. A and A denote the enzyme activities without and with inhibitor, respectively. Concentrations of [$^3$H]-poly (A) of 15–50 nM are hydrolyzed by 10 $\mu$M RNase B in a concentration-dependent fashion, but DNP-[3H]-poly(A)is not hydrolyzed. Thus, DNP-poly(A) acts as a competitive inhibitor of RNase B.

Example II

High Purity Synthesis of Phenyl-Derivatized Oligoribonucleotides

In another embodiment of the methods of this invention, an alternative procedure for derivatizing oligoribonucleotides is provided. The prior state of the art for solid-state synthesis for RNA gives at best a yield of 93% per cycle for native monomers and still lower values for chemically altered monomers. Thus, the expected yield for an n-mer oligoribonucleotide will be $(0.93)^n$. By way of example only, the expected yield for a 20-mer oligoribonucleotide will be lower than $(0.93)^{20}$, or 23%. Similarly, the expected yield for a 40-mer will be $(0.93)^{40}$, or less than 0.055%.

The methods of this invention can use a procedure to label the 2'-OH groups of preformed RNA with 1-fluoro-2,4-dinitrobenzene (FDNB) under mild conditions with negligible degradation. Because the RNAs used for these syntheses are already full length RNAs of the desired sequence and are pure, no oligomerization of derivatized oligoribonucleotides is necessary. Therefore, the reactants and products can be easily separated to yield pure, full length, derivatized RNA sequences with no stereoisomers being present. By way of example only, a DNA template with T7 promoter can be made by solid state synthesis. Since commercial DNA synthesis can reach a yield of 99% per cycle, the expected yield of a 20-mer is about 82%.

After purification by gel electrophoresis, the template is used to make RNA by in vitro transcription catalyzed by T7 polymerase. Conditions for such a reaction can include, by way of example only, 30 mM $MgCl_2$, 5 mM dithiothreitol, 1 mM spermidine, 50 mM Tris buffer (pH 8.1), 250 mM DNA template, 2 unit/µl T7 RNA polymerase and 4 mM of each ribonucleotide. The solution is then incubated at 37° C. for six hours. The DNA templates are subsequently digested by DNase I. The aqueous mixture is extracted using phenol/chloroform to remove proteins and the RNA in the aqueous phase is precipitated using 100% ethanol. The extracted RNA can then be derivatized with FDNB in a weakly basic mixture. Thirty mg of the oligoribonucleotide is dissolved in 2 ml of 0.4 M $KHCO_3/K_2CO_3$ (pH 8.8) buffer and 1 ml acetone, stirred gently and then added 200 µl of FDNB are added. The mixture is incubated at 37° C. Every two hours thereafter, 15 µl of FDNB is added and the pH kept between 8.7 and 8.9. In total, 150 µl of FDNB is added to the solution. After 24 hours, the reaction was maintained at 20° C. overnight for completion.

The unreacted FDNB and its other reaction products can then be removed from the derivatized RNA by extracting the solution of derivatized RNAs four times with DMSO/$CH_2Cl_2$ (V/V=1/7). The aqueous solution can then be put into cellulose tubing of pore size permitting molecules of about 3,500 M.W. and dialyzed against water to remove acetone, dinitrophenol and other solvents. Finally, the dialyzed solution can be lyophilized. The DNP/nucleotide molar ration, determined from the absorbances at 260 and 330 nm, respectively, is around 0.7. Electrophoresis of annealed mixtures confirmed that the synthetic complementary sDNA template hybridizes with the product, poly-DNP-RNA.

Because the phenyl groups are conjugated to the ribose moieties of the oligoribonucleotides of this invention, the derivatization is in no way dependent on the nucleotide sequence. Therefore, workers of ordinary skill in the art would know that the methods and oligoribonucleotides disclosed would be applicable to oligoribonucleotides of any sequence. This improved purity and results in improved therapeutic efficacy. In fact, the $IC_{50}$ of the inhibition of SK-Br-3 cells by Compound XII (antisense PKA) is about 8 µg/ml, which is one or two orders of magnitude lower than the $IC_{50}$ for conventional PS ODNs (see Example IX below).

Antisense and sense phosphorothioate oligonucleotides can be readily prepared on 1 µmol or 10 µmol scales with an Applied Biosystems Model 380B DNA synthesizer using reported procedures in Zon et al. *Oligonucleotides and Analogues: A Practical Approach,* F. Eckstein, Ed. (Oxford University Press, Oxford, England), pp. 87–108 (1991), the disclosure of which is hereby incorporated by reference. The process generally includes substitution of a sulfur-donor reagent (as described in U.S. Pat. No. 5,151,510, the disclosure of which is hereby incorporated by reference) for iodine-water-pyridine, reversing the normal oxidation-then-cap sequence within each cycle, preparative reversed-phase high-performance liquid chromatography, detritylation, isolation of the final product in the form of its sodium salt, and then analysis by capillary gel electrophoresis. See also Zon et al. *Anti-Cancer Drug Design* 6:539 (1991), the disclosure of which is hereby incorporated by reference. Product is generally recovered as greater than or equal to 85 percent of full-length product through comparison to size standards. Antisense therapy is a young art, however, some of the first antisense therapeutic agents have gone into human patients in the last several years. (e.g., Bayever et al. *Antisense Research and Development* 2:109–110 (1992). It is expected, therefore, that the antisense oligomers of the present invention can be suitably used in vivo in humans.

Example III

Treatment of MuLV in a Mammal with DNP-Poly [A]

Previous work performed by and under the direction of the inventor has demonstrated that poly-2'-O-(2,4-dinitrophenyl) poly [A] (Compound I) is a potent inhibitor of reverse transcriptases from a variety of sources. (Kang, I and Wang, J. H. "Design of Structure-based Reverse Transcriptase Inhibitors" *J. Biol. Chem.* 269:12024–12031 (1994)). In the present study, its inhibitory effect on the reverse transcriptase from Moloney Murine Leukemia Virus (MuLV RT) was investigated. We chose to study DNP-poly [A](DNP-[A]$_{15}$) for these studies, having a sequence as follows:

5'-aaaaaaaaaa aaaaa-3'                (SEQ ID NO: 1).

DNP-poly [A] (Compound I) was found to enter the virus spontaneously and completely inhibit the RT within 30 minutes at 0C. The inhibitor was also spontaneously transported into isolated human lymphocytes and leukocytes at 37° C.

Animal studies have demonstrated the effectiveness of DNP-poly [A] as an antiviral drug when administered i.p. with varying doses from 1 mg to 100 mg/kg body weight. MuLV-infected mice show the presence of RT in their blood as well as increased numbers of abnormal white blood cells. After the administration of DNP-poly [A] at a dose of 100 mg/kg body weight, three times a week over a 3 week period, RT cannot be detected by an ultrasensitive RT-PCR assay. Autopsy showed that the spleens of infected but untreated mice were enlarged 2–10 fold with fused nodules and proliferation of large abnormal lymphocytes whereas the spleens of infected but treated mice resemble the normal spleens of uninfected control mice.

As toxicity controls, uninfected mice were also injected with 1 to 100 mg DNP-poly [A]/kg body weight. They showed WBC and RBC counts within the normal range. Their spleens had normal weights and histology.

The macromolecular inhibitor poly-2'-O-(2,4-dinitrophenyl) poly[A] (DNP-poly[A]) was first designed (Kang, I and Wang, J. H. "Design of Structure-based Reverse Transcriptase Inhibitors" *J. Biol. Chem.* 269:12024–12031 (1994)) on the basis of crystallographic data on the active site of HIV RT (Kohlstaedt et al. "Crystal Structure at 3.5 Å Resolution of HIV-2 Reverse Transcriptase complexed with an inhibitor" *Science* 256:1783–1790 (1992), Arnold et al. "Structure of HIV-1 Reverse Transcriptase/DNA complex at 7 Å resolution showing active site locations" *Nature* 357: 85–89 (1992), the disclosures of which are hereby incorporated by reference) and was synthesized to investigate the inhibition of reverse transcriptases such as HIV RT (wild type) and other retroviruses. It is precisely those other retroviruses that are a focus of the present Example.

A. Materials and Methods 1.1 Compounds & Enzymes

[$^3$H] Poly [A] (22.8 Ci/mmol) was from Amersham, (Arlington Heights, Ill.) and [3H] dTTP (83.8 Ci/mmol) was from NEN Du Pont, (Boston, Mass.). GF/C filters were from Whatman's (Hillsboro, Oreg.). Oxirane acrylic beads (250 $\mu$m), epoxy activated Sepharose 6B, poly [A]•[dT]$_{12}$, Ultra Pure reagents for PCR and human plasma were all from Sigma Chemical Co., (St. Louis, Mo.). RNAsin was from Promega, (Madison, Wis.), MS2 RNA from Boehringer Mannheim, (Indianapolis, Ind.), Taq DNA Polymerase and gel electrophoresis reagents were purchased from Life Technologies, (Grand Island, N.Y.). HIV RT was purchased from Worthington Biochemical Corp., (Freehold, N.J.) and stored in 10 mM potassium phosphate (pH 7.1) with 1 mM DTT and 50% glycerol (v/v) at −20° C.

1.2 Virus and Cells

M-MuLV-ecotropic (suspended in Dulbecco's MEM (high glucose) with 10% FBS and 50 $\mu$g/ml gentamicin) and elutriated cell preparations of human lymphocytes and leukocytes were purchased from Advanced Biotechnologies, (Columbia, Md.).

1.3. Assay of RNA-Dependent DNA Polymerase Activity of MuLV RT

This was carried out according to the procedure of Sherr et al. "Murine Leukemia Virus Reverse Transcriptase assay" in: William B. Jakoby and Ira Pastan (Eds), *Methods in Enzymology* 58:12–417 (1979), the disclosure of which is hereby incorporated by reference in its entirety. A Beckman Airfuge was used for the high speed centrifugation step of the assay.

1.4. Testing the Stability of DNP-poly [A] in 0.01 M HCl at 37° C.

DNP-poly [A] was incubated in 0.01 M HCL at 37° C. for 4 hrs and 24 hrs. At the end of the incubation period, each tube was immersed in liquid nitrogen to stop any further inactivation. The IC$_{50}$ values of HIV RT (at 25 nM) were determined by the procedure described elsewhere (Kang and Wang, supra (1994)). Control experiments were also run with diethylpyrocarbonate (DEPC) treated water.

1.5 Preparation of Sepharose 6B with Covalently Attached DNP-poly [A]

About 200 mg of epoxy-activated sepharose 6B was suspended in 4 ml of DNP-poly [A] solution (2.5 mg/ml). The suspension was mixed with 1 ml of 1.0 M K$_2$CO$_3$ solution, adjusted to pH 10–11 with KHCO$_3$ and gently shaken for 2 days at 25° C. The derivatized resin suspension was transferred to a 3-ml syringe fitted with a filter. From the decreased absorbance of the filtrate at 259 nm, the yield was estimated to be 2 mg DNP-poly [A]/g resin. The resin was sequentially washed with water, 1.0 M KCl solution and buffered medium before use.

1.6 Preparation of Oxirane Beads with Covalently Attached DNP-poly [A]

Oxirane beads bound to DNP-poly [A] are prepared by the method of Rahman et al., *Anal. Chem.* 68:134–138 (1996).

1.7 Binding of Murine Leukemia Virus to DNP-poly [A] Covalently Attached to Oxirane Acrylic/Sepharose Beads Epoxy-activated Sepharose or oxirane acrylic beads with covalently attached DNP-poly [A] were pre-equilibrated with 1 ml of buffer/human plasma for 72 hrs at 25° C. At each titration step, a mixture of 10$^8$ MuLV in 100 $\mu$l buffer or plasma was added to the resin suspension and shaken at 0° C. for 60 minutes. An aliquot (50 $\mu$l) of the supernatant was then removed, airfuged through a glycerol layer (20% glycerol, 0.05 M Tris-HCL pH 7.8, 0.1 M KCL) at 100,000×g to pellet the virus and assayed for RT activity as described in Section 1.3.

1.8 Transport of DNP-poly [A] into Murine Leukemia Virus

Five $\mu$l of medium containing 6×10$^8$ virus particles was incubated at 0° C. with 10 $\mu$l of a 2 $\mu$M DNP-poly [A] stock solution. At a time 't', the virus was centrifuged through a glycerol layer for 10 minutes at 100,000×g. The supernatant was carefully removed and the pellet was washed with 200 $\mu$l Tris-HCL buffer (50 mM, pH 7.8) and again centrifuged. The pellet was then homogenized in 12 $\mu$l of 0.5% Triton X-100 at 0° C. for 3 minutes and incubated with MuLV RT assay mixture at 37° C. for 60 minutes. The assay reaction was terminated by the addition of 3 ml, 10% TCA. The incorporated radioactive product was collected on a GF/C filter, washed and counted in a Wallac Liquid Scintillation Counter.

1.9. Transport of DNP-poly [A] into Human Lymphocytes-Leukocytes at 37° C.

A 400 $\mu$l suspension containing 8×10$^6$ cells in 100 $\mu$l FSA, 3.2 ml RPMI 1640 and 300 $\mu$l [$^{14}$C] DNP-poly [A] (0.05 mg/ml, 3024 cpm/$\mu$g) was divided into several aliquots and incubated at 37° C. for various lengths of time. At time 't', the incubation mixture was centrifuged at 3000×g for 5 minutes in an Eppendorf Centrifuge and the supernatant was discarded. The pellet was carefully washed with 300 $\mu$l of PBS, centrifuged and the supernatant discarded. This washing procedure was performed three times. The homogenized pellet was then immersed in S ml of counting cocktail and counted in a Wallac Liquid Scintillation counter.

1.10. Animal Experiments

Fifty four male Balb/c mice, approximately 3 weeks old, were purchased from Harlan Sprague Dawley, (Indianapolis, Ind.) and weighed 12–15 g prior to infection and/or treatment. Thirty mice were infected i.p. or i.v. (via tail vein) with 10$^5$ to 10$^8$ virus particles (10$^{8.25}$ TCID$_{50}$/ml titered in SC-1/XC infectivity assay over a 12 day period) in saline. DNP-poly [A] was administered i.p. in saline in varying doses of 1 to 100 mg/kg body weight. Blood was periodically drawn from the tail and used in PERT assay.

1.11. Sample Pre-treatment for PERT (Product Enhanced RT) Assay

The method of Pyra et al. "Ultrasensitive retrovirus detection by a reverse transcriptase assay based on product enhancement" *Proc. Natl. Acad. Sci. USA* 91:1544–1548 (1994) (the disclosure of which is hereby incorporated by reference in its entirety) was used with some modifications. Briefly, 5 μl of whole blood was collected into 5 μl EDTA (13.8% w/v)+45 μl saline and frozen at −20° C. overnight. The hemolyzed blood was then centrifuged at 4000×g for 30 minutes at 4° C. The supernatant was removed and again centrifuged at 100,000×g for 30 minutes. The pellet was then homogenized in 20 μl Buffer A containing 50 mM KCL, 50% glycerol, 25 mM Tris HCL (pH 7.5), 0.25 mM EDTA, 0.5% Triton X-100 and 5 mM DTT. This suspension was kept at 0° C. for 15 minutes and 3 Al was removed and used in the PERT assay.

1.12. PERT & Product Amplification by PCR

The procedure described by Pyra et al. supra (1994) was carried out without any modifications.

B. Results

Intact MuLV particles in aqueous buffer exhibit no RT activity toward substrate and primer-template in external medium. But the activity can be measured by first releasing the endogenous RT with low concentrations of Triton X-100 (0.1–0.5%). In the present work, the transport of DNP-poly [A] into MuLV was monitored by mixing them in the absence of the detergent, taking aliquots of the mixture at different time intervals after mixing, centrifugation of each aliquot and washing each sediment to remove external DNP-poly [A]. The washed virus was subsequently treated with Triton X-100 to release the RT, and finally incubated in assay solution, and the processed virus was used for determination of RT activity. The result of a typical experiment is illustrated in FIG. 1 where the observed ratio $A/A_0$ of the RT activities observed before and after incubation with DNP-poly [A] is given as a function of incubation time. It shows that even at 0° C., the macromolecule was rapidly transported into MuLV to inhibit the endogenous RT. The DNP-poly [A] used in this study has an average molecular weight of $1.1 \times 10^5$ and adenine/DNP molar ratio of 1.5.

FIG. 2 illustrates similar results from experiments on the transport of DNP-[$^{14}$C] poly [A] into human lymphocytes and leukocytes, respectively, at 37° C. These observations show that the hydrophobic effect of a large number of DNP groups can compensate the hydrophilic effect of charged phosphate groups in each DNP-poly [A] molecule sufficiently to make it membrane-permeable. By contrast, the hydrophilic underivatized poly [A] of equal chain length was not at all transported under the same conditions.

To exploit this membrane-permeability, each DNP-poly [A] molecule was covalently linked to oxirane acrylic resin, and found that the resulting affinity resin can bind MuLV selectively from its suspension in human plasma. Presumably, the covalently anchored DNP-poly [A] (approximately 0.06 μm in length) can penetrate into the retrovirus (approximately 0.1 μm) and catch the particles by binding to the endogenous RT as illustrated in the inset of FIG. 3. It was found that shaking with this affinity resin can selectively remove MuLV suspended in human plasma. In order to determine the binding free energy, a suspension of the affinity resin was titrated with the retrovirus. At equilibrium, the concentration of free virus (C), the moles of virus bound per mg of resin (n) and the virus binding capacity (N) are related by the equation:

$$n/C = (N-n)K_d$$

where $K_d$ is the dissociation constant of the bound virus. The corresponding linear plot of experimental data in FIG. 4 gives $K_d = 3.4 \times 10^{-12}$ M and $N = 1.4 \times 10^9$ virus particles per mg.

Unlike the natural polynucleotides, DNP-poly [A] is completely stable in solutions containing ribonucleases A, B, S, $T_1$, $T_2$, and H, as well as phosphodiesterases 1 and 2 (see Example I, Rahman et al. supra (1996)). DNP-poly [A] was also found to be quite stable in acidic medium in that it was able to retain its inhibition potency when incubated several hours in 0.01 M HCL and water respectively at 37° C. FIG. 4 (top) and 4 (bottom) shows that in both situations, there is still inhibition after the incubation with acid for 4 and 24 hours, respectively. The membrane permeability and chemical stability of DNP-poly [A] suggest that this RT inhibitor could be used as an unusually effective anti-retroviral agent. As a test case, MuLV-infected mice were treated with doses of DNP-poly [A] in phosphate buffered saline (D-PBS) by i.p. injection and followed their blood chemistry and spleen histology in comparison with those of the control mice (infected and untreated, uninfected and untreated, uninfected and treated, respectively).

In the early stages of the diseases, HCT measurements gave some indication on the progress of infection (FIG. 5). Mice that were treated immediately after viral infection up to 3 times, at three day intervals with 10 mg/kg body weight, did not manifest leukemic symptoms such as large splenic cells, large spleens or low hematocrit (<40%) which was observed in infected but untreated mice (FIG. 6). The subsequently treated mice had normal spleen architecture. After about 4 months, the blood from infected but untreated mice showed a strong signal on ethidium bromide stained gels obtained by PERT assay due to circulating virus particles and infected cells. This band corresponds to approximately 100 bp according to the PCR marker which was run alongside it. FIG. 7 shows that these bands progressively lost their intensity after the DNP-poly [A] treatment of 100 ng/kg was introduced and continued for up to 3 weeks, and eventually disappeared. These mice, had twice the normal spleen weight at autopsy. FIG. 8B shows an infected but untreated mouse spleen (10× normal spleen weight) that is greatly enlarged and has lost the normal spleen architecture. Under high magnification, large abnormal cells can be seen to proliferate within the infected but untreated spleen to such an extent that normal lymphocytes are very rare in the whole field. Spleens of infected but treated mice had some regions of hypemodularity (FIG. 8C) but there were still distinct regions of white and red pulp and their blood films looked more normal than abnormal. As toxicity controls, uninfected mice were also administered with 1 to 100 mg DNP-poly [A] (FIG. 8D). The WBC, HCT and RBC counts for these animals were within normal limits.

C. Discussion

The use of macromolecular inhibitors as therapeutic agents is often hampered by their failure to cross biological transport barriers. It has now been discovered that derivatives of poly [A] with DNP groups attached to the 2'-O positions via ether linkage can be transported freely and rapidly into viruses and cells, whereas poly [A] itself cannot. This poly [A] derivative was previously shown to protect susceptible lymphocytes from HIV (Kang and Wang supra (1994)). The new transport data suggest a protection mechanism involving permeation of the inhibitor through viral and cellular membranes followed by inhibition of the reverse transcriptase inside. Although the MuLV-infected mice reported in this work were treated with DNP-poly [A] by i.p. injection, the membrane permeability and chemical stability of DNP-poly [A] suggest that oral or transdermal administration of inhibitor should also be explored.

In MuLV infected mice, more and more abnormal giant cells were observed within the spleen as the RBC population decreased eventually giving rise to anemia. The mice that were treated after 4 months of infection had obviously already developed the disease to such an extent that although viral load in blood was markedly decreased, the spleen was still infiltrated by abnormal looking cells. These large pathological cells dominated the spleen population as the disease progressed. Mice are lymphocytic animals and various investigators have documented blood lymphocyte/neutrophil ratios of $\geq 2$. Shermer "The White Mouse" In: *The Blood Morphology of Laboratory Animals*, pp. 61–74 (1967), the disclosure of which is hereby incorporated by reference in its entirety. However, in the infected but untreated animals the ratio of lymphocyte/neutrophil was found to be <½. This observation has not been documented in MuLV infected mice. Since the mouse is an animal with very small blood volume (5.5%–8.0% body weight) multiple tests can only be performed on microscale. In the present work RT-PCR was used to monitor viral load because it requires only 5 $\mu$l of whole blood per assay.

When MuLV replicates, thereby giving rise to more virus particles, the amount of RT increases. Consequently, the cDNA produced by reverse transcription increases also. Conversely, a decrease in the intensity of the 100 bp band on ethidium bromide stained gels demonstrates a decrease in cDNA and therefore RT. The results indicate that multiple treatment with DNP-poly [A] can decrease viral load to zero. Indeed, the viral RT was still not detectable two weeks after treatment was terminated (data not shown). The PERT and RT-PCR assays developed by Pyra et al. "Ultrasensitive retrovirus detection by a reverse transcriptase assay based on product enhancement" *Proc. Natl. Acad. Sci. USA* 91:1544–1548 (1994) (the disclosure of which is hereby incorporated by reference in its entirety) are sufficiently sensitive to detect $10^{-9}$ unit of RT activity.

MuLV RT has a molecular weight of 71,000 and a specific activity of about 40,000 units/mg and, therefore, $10^{-9}$ unit of RT would represent $2.1 \times 10^2$ RT molecules. In avian and mammalian type C retroviruses, it has been estimated that there are 20–70 RT molecules per virion. Stromberg et al. "Structural studies of Avian Myeloblastosis Virus: Comparison of polypeptides in virion and core components by dodecyl sulfate-polyacrylamide gel electrophoresis" *J. Virology* 13:513–528 (1974), the disclosure of which is hereby incorporated by reference in its entirety. This would correspond to as little as 3–11 virions detectable. Pyra et al. supra (1994). The positive controls (pure virus) gave strong signals whereas negative controls (normal uninfected blood or buffer) showed no bands. Therefore, this assay is useful and reliable for quantitation of virus load as well as determination of susceptibility of MuLV to DNP-poly [A]. One of the main problems of in vivo drug administration is the possible side effects caused by the drug. However, at the doses used in the present experiments, no toxic effects were observed. On the basis of previous in vitro studies and the present work, it seems reasonable to attribute the decrease in viral load and maintenance of normal spleen architecture to the antiretroviral activity of DNP-poly [A] although the possibility that some form of cellular immunity may have been activated during the course of treatment cannot be excluded as a possible explanation.

Example IV

Treatment of Murine Leukemia Virus (MuLV) Using Antisense Oligoribonucleotides I 1.1 Design of an Antisense Oligoribonucleotide The complete sequence of Murine Leukemia Virus has been published by Shinnick et al. *Nature* 293:543–548 (1981). The gene is 8333 bases in length. A portion of the sequence, from base 8107 to base 8131, corresponding to a polypeptide segment in the env protein that is essential for the replication of MuLV was selected. Granowitz et al. showed that mutants with altered sequence in this region of the env gene are replication-defective. Granowitz et al. *Virology* 183:545 (1991). The selected sequence is as follows:

5'-ggacccugca uucuuauucg auua-3'    (SEQ ID NO:2).

A 15-mer antisense oligonucleotide was designed to be complementary to the 5' end of SEQ ID NO:2, so as to block the synthesis of the envelope protein, env, of MuLV. The oligoribonucleotide has the following sequence:

5'-aagaaugcag ggucc-3' (SEQ ID NO:3).

The antisense oligoribonucleotide was ordered from, and custom synthesized by, Oligo Therapeutics, Inc.

1.2 Derivatization of the Antisense Oligoribonucleotide

In order to derivatize the antisense oligonucleotide for therapeutic evaluation, the oligoribonucleotide of SEQ ID NO:3 was reacted with 1-fluoro-2,4-dinitrobenzene as follows:

2 mg of SEQ ID NO:3 was dissolved in 0.1 ml of diethylpyrocarbonate (DEPC) treated water and 20 $\mu$l of 0.1 M K$_2$CO$_3$+2.0 M KHCO$_3$ buffer (pH 8.8). 3.5 $\mu$l of 1-fluoro-2,4-dinitrobenzene (FDNB) in 60 $\mu$l of acetone was mixed in. The mixture was gently stirred in a capped glass vial at 35° C. for 48 hours. As the reaction progressed, additional FDNB and K$_2$CO$_3$ or KHCO$_3$ were added from time to time to replenish the reagent and maintain the pH at approximately 8.8 as described in Table 1 below.

TABLE I

Derivatization of Antisense Oligoribonucleotides

| Elapsed Time | FDNB added | pH | Temperature |
|---|---|---|---|
| Start | 3.5 $\mu$l | 8.8 | 35° C. |
| 1 Hour | 3.5 $\mu$l | 8.7 | 35° C. |
| 2.5 Hours | 3.5 $\mu$l | 9.1 | 35° C. |
| 5 Hours | 7 $\mu$l | 9.3 -> 8.8 | 35° C. |
| 9 Hours | 3.5 $\mu$l | 9.1 | 35° C. |
| 20 Hours | 3.5 $\mu$l | 8.3 -> 8.7 | 35° C. |
| 24 Hours | 3.5 $\mu$l | 8.6 | 35° C. |
| 29 Hours | — | — | 25° C. |
| 48 hours | reaction terminated | | |

The reaction mixture was extracted with pH 8.8 buffer plus half its volume of acetone. The extract was dialyzed for 3 days against fresh water through a membrane permeable to molecules with an M$_r$<1000. The dialyzed sample was recovered and its UV absorbance at 259 and 330 was measured to determine the molar ratio of DNP to nucleotide. The absorbances, A$_{259}$=0.151 and A$_{330}$=0.023, yielded a molar ratio of 0.81 DNP to nucleotide. The overall yield of the reaction was calculated to be 72%. The resulting anti-env DNP derivatized oligoribonucleotide is hereinafter denoted Compound II. A 15-mer random sequence having the following sequence:

5'-ugacccugca uucug-3'    (SEQ ID NO:4)

was also synthesized and derivatized as described above, and denoted Compound III.

1.3 In Vivo Treatment of MuLV

In order to test the effectiveness of the DNP derivatized antisense oligonucleotide (SEQ ID NO:2) prepared as above, six Balb/c mice (all male litter mates at 3–6 weeks of age) were infected with MuLV (mice A, B, C, D, E, and F).

were again withdrawn from all of the mice. Mice A, B, and G remained free of virus and mice C, D, and E continued to express the viral gene. See FIG. 9c.

Figure 9A:
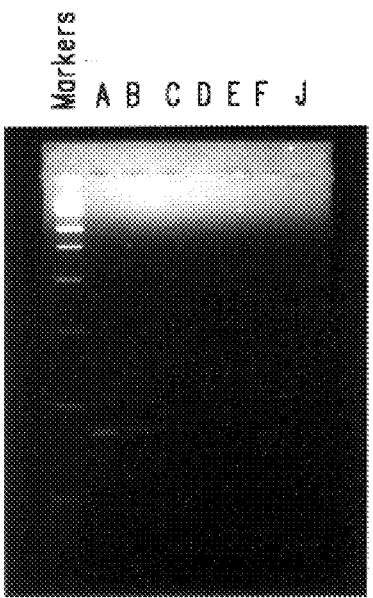
Figure 9B:
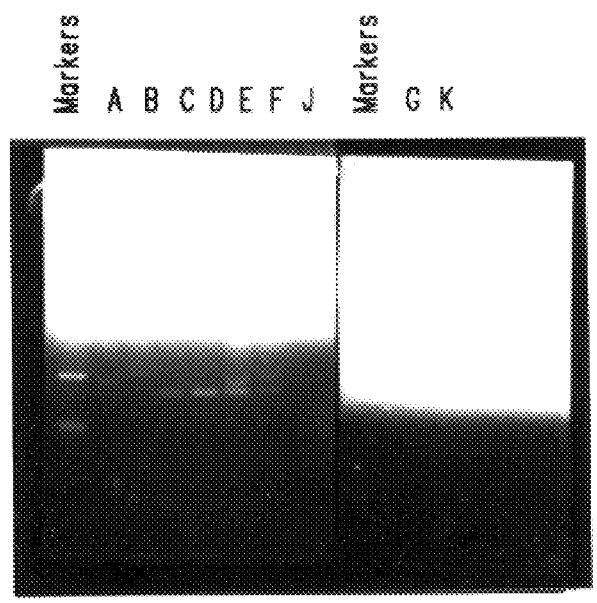
Figure 9C:
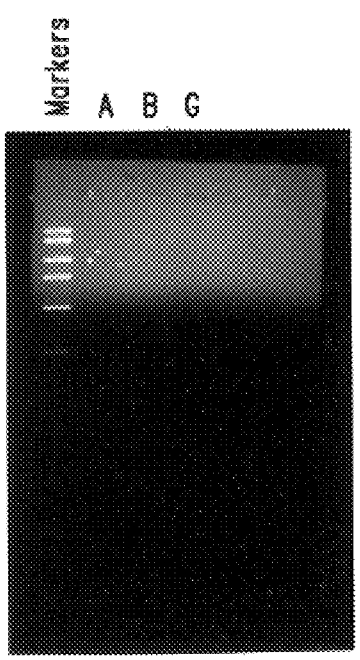
Figure 9D:
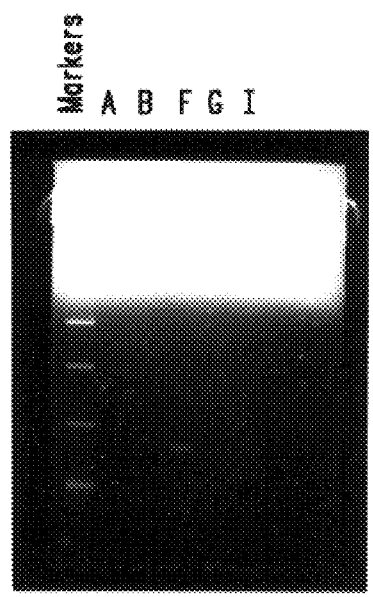

On day forty, the treatment of mouse B was discontinued while the treatment of mice A and G was continued on a reduced dosing schedule (2.5 mg/kg, two times/week). On day 50, blood samples were withdrawn from all of the mice. Mice A, B, and G remained free from virus while mice C, D, and E continued to express the viral gene (FIG. 9d).

The results of the experiment are summarized in the following Table II.

TABLE II

Antisense Oligoribonucleotides Inhibit MuLV in Vivo

| Mouse | Day 1 | Day 5 RT-PCR for Virus | Day 20 RT-PCR for Virus[2] | Day 24 Treatment | Treatment | Day 30 RT-PCR for Virus[3] | Treatment | Day 38 RT-PCR for Virus[4] | Day 40 Treatment | Treatment | Day 50 RT-PCR for Virus[5] |
|---|---|---|---|---|---|---|---|---|---|---|---|
| A | Inoculated[1] | − | + | 2.5 mg/kg, 3x/week | 2.5 mg/kg, 3x/week | − | 2.5 mg/kg, 3x/week | − | NT | NT | − |
| B | Inoculated[1] | − | + | 2.5 mg/kg, 3x/week | 2.5 mg/kg, 3x/week | − | 2.5 mg/kg, 3x/week | − | 2.5 mg/kg, 2x/week | 2.5 mg/kg, 2x/week | − |
| C | Inoculated[1] | − | − | NT | NT | + | NT | + | NT | NT | + |
| D | Inoculated[1] | − | − | NT | NT | + | NT | + | NT | NT | + |
| E | Inoculated[1] | − | − | NT | NT | + | NT | + | NT | NT | + |
| F | Inoculated[1] | − | + | NT | NT | + | NT | + | NT | NT | + |
| G | Control | − | − | 2.5 mg/kg, 3x/week | 2.5 mg/kg, 3x/week | − | 2.5 mg/kg, 3x/week | − | 2.5 mg/kg, 2x/week | 2.5 mg/kg, 2x/week | − |

NT = Not treated.
Note
[1]= Inoculation was accomplished with 8.3 × 10$^6$ virus particles per mouse.
Note
[2]= See FIG. 9a.
Note
[3]= See FIG. 9b.
Note
[4]= See FIG. 9c.
Note
[5]= See FIG. 9d.

To this end, the mice received 8.3×10$^6$ VP/mouse via intravenous injection. Approximately five days later, blood samples were withdrawn from all six mice and from a normal, uninfected mouse (G) as a control. An RT-PCR assay was performed on the blood samples to determine the presence of virus. None of the seven samples exhibited virus based on electrophoresis.

On day twenty, blood samples were again withdrawn from all six mice and the samples tested for the presence of virus through RT-PCR. Three of the mice showed evidence of the virus (A, B, and F), while three others did not (C, D, and E) (FIG. 9a). On day twenty-four, two of the mice evidencing infection (A and B) were treated for a week with the antisense DNP-oligo with a dosage of 2.5 mg/kg, three times/week by intraperitoneal injection. The control mouse G that was not infected with the virus was also treated. Mouse F, which showed evidence of virus on day 20 was left untreated, as were mice C, D, and E.

Blood samples were again withdrawn from all of the mice on day thirty. Evidence of virus through RT-PCR assay and electrophoresis disappeared in the infected/treated mice (A and B). Mouse G is also free from evidence of virus. However, mice C, D, and E indicate presence of the virus (FIG. 9b).

Treatment of mice A, B, and G was continued for an additional seven days. On day thirty-eight, blood samples The above data indicate that the antisense DNP oligonucleotides of the present invention operate to block synthesis of the viral envelope protein of MuLV. The nucleotides appeared to have been freely available to infected cells. This finding is supported by the results presented in Example I relating to the bioavailability of DNP-poly [A]. Moreover, the nucleotides did not appear to be susceptible to enzymatic degradation. This finding is again supported by the results demonstrated in Example I related to the enzymatic degradation of DNP-poly [A]. Particularly impressive with respect to the data was the fact that upon discontinuing treatment in mouse B there was no evidence of viral infection persisting. This fact appears to demonstrate that either the oligonucleotide persisted in hybridizing to the MuLV gene or that the MuLV infection was vanquished by the host mouse.

Example V

Design of Antisense Oligoribonucleotides and Their Use for Treating Murine Leukemia in Vivo II A multi-functional, poly-2'-O-(2,4-dinitrophenyl) inhibitor (FIG. 10; Compound IV) was synthesized with the following sequence:

5'-gggacagucu gguacauaag aaugcagggu cc-3'    (SEQ ID NO:5).

This inhibitor was designed to inhibit viral reverse transcriptase, a gene for viral envelope synthesis, env, and a protease of MuLV. FIG. 10 illustrates the complementary binding of the anti-envelope portion of the antisense Compound IV (left side of FIG. 10) to the complementary portion of the retroviral mRNA (right of FIG. 10).

Methods for determining therapeutic efficacy of Compound IV were carried out according to the methods described in Example IV. Intraperitoneal administration of Compound IV to MuLV-infected mice for 3 weeks was found to decrease viremia to undetectable levels (Table III). Viremia did not reappear even after 8 weeks after termination of treatment, at which time the mice were sacrificed for autopsy. The infected but untreated mice died within 6 months with enlarged spleens that exhibited abnormal histology and were found by PCR to contain integrated MuLV genomic sequences. The infected but subsequently treated mice had normal spleens and showed no integrated viral genome in either their spleens or bone marrows for as long as three months after termination of treatment, the longest time after treatment currently available. The effective intraperitoneal dosages ($ED_{50}$) were 50, 0.25, and 0.1 mg/kg for the monofunctional poly-DNP-oligo A (Compound I), the antisense Compound II and the multifunctional Compound IV, respectively. Oral administration of Compounds I or IV were also effective, but with approximately 10-fold higher $ED_{50}$ values. For comparison, poly-DNP-oligo A (Compound I) and Compound V, a DNP-derivatized 32 mer oligoribonucleotide containing the sense sequence:

5'-cccugucaga ccauguauuc uuacguccca gg-3'         (SEQ ID NO:6), and Compound VI, a DNP-derivatized oligoribonucleotide 47-mer with random sequence:

5'-ggguccagcu aaaugcaggc auaaauguga acgcgaacgg uaucagc-3'         (SEQ ID NO:7)

were also tested. Compound IV inhibited MuLV by binding either to the mRNA of envelope gene as illustrated in FIG. 10 or to that of the protease gene or to the reverse transcriptase. The data are summarized in the following table.

TABLE III

Treatment of MuL V-infected mice with trifunctional compound IV and control poly-DNP-oligoribonucleotides

| Class of mice | No. of mice | Antisense RNA Used | Viremia (%) after treatment for 3 weeks | 7 weeks |
|---|---|---|---|---|
| Normal | 7 | None | −100[d] | −100[d] |
| Infected | 10 | IV (0.25 mg/Kg, ip)[a] | −50 | −90 |
| Infected | 10 | IV (0.025 mg/Kg, ip)[a] | −30 | −30 |
| Infected | 2 | IV (2.5 mg/Kg, ip)[b] | −100 | −100 |
| Infected | 2 | I (100 mg/Kg, ip)[b] | −100 | −100 |
| Infected | 2 | I (50 mg/Kg, ip)[b] | −50 | −50 |
| Infected | 2 | I (2.5 mg/Kg, ip)[b] | + | + |
| Infected | 2 | V (2.5 mg/Kg, ip)[a] | + | + |
| Infected | 2 | VI (2.5 mg/Kg, ip)[a] | + | + |
| Infected | 6 | IV (2.5 mg/Kg, oral)[c] |  | −100 |
| Infected | 6 | IV (1 mg/Kg, oral)[c] |  | −40 |
| Infected | 5 | IV (0.25 mg/Kg, oral)[c] |  | + |
| Infected | 7 | None | +100 | + |

TABLE III-continued

Treatment of MuL V-infected mice with trifunctional compound IV and control poly-DNP-oligoribonucleotides

| Class of mice | No. of mice | Antisense RNA Used | Viremia (%) after treatment for 3 weeks | 7 weeks |
|---|---|---|---|---|

All treatments are by ip or oral administration either daily[a] or 3 times/week[b], or every other day[c]; [d]The minus (−) sign indicates that the amount of cDNA produced by RT-PCR assay is below detectable level in gel electrophoresis. The plus (+) sigh indicates that cDNA was detected by RT-PCR assay.

The effective concentrations in vivo of the multifunctional Compound IV are substantially lower than the concentrations of either native oligoribonucleotides or oligoribonucleotides derivatized using any prior art methods.

Antisense thiolated oligonucleotides have been used by many investigators as anticancer agents. They can suppress cancer growth but have quite high toxicity. One of the advantages of poly-DNP-oligoribonucleotides of this invention is their low toxicity. Table III shows that dosages of up to 100 mg/Kg of poly-DNP-oligo A (Compound I) has no noticeable ill effect and that the $ED_{50}$ of Compound IV (a 32-mer oligoribonucleotide with the same type of structure as DNP-oligo A) is only 0.1 mg/Kg. Thus, the therapeutic ratio, Example VI Treatment of Hepatitis B in Ducks In Vivo I To determine whether DNP-derivatized antisense oligoribonucleotides can inhibit hepatitis, we performed a series of experiments in ducks infected with the avian hepatitis B virus (DHBV). The complete sequence of Duck Hepatitis B Virus has been published by Schneider et al. in GenBank, Title: GBVRL2.SEQ, Locus: DHVBCG, Accession: X60213 (Nov. 19, 1992). The gene is 3027 bases in length. A bifunctional inhibitor comprising DNP groups and an antisense sequence directed at a region of the polymerase of DHBV. The target sequence was:

5'-aauccugcug acggccc-3'         (SEQ ID NO: 8).

This represents nucleotides 2428–2445 of the polymerase gene of DHBV. The antisense oligoribonucleotide was:

5'-gggccgucag caggauu-3'         (SEQ ID NO:9).

The antisense oligoribonucleotide was synthesized in vitro using T7 polymerase and synthetic promoter-template ds-DNA. The antisense oligoribonucleotide was purified and then covalently labeled with 1-fluoro-2,4-dinitrobenzene at the 2'-O positions resulting in a DNP derivatized oligoribonucleotide (Compound VII). The DNP/nucleotide molar ratio in the derivatized product (DNP-antisense oligoribonucleotide) was 0.57. This antisense DNP-oligoribonucleotide Compound VII was found to have the following properties in vitro. First, it is not hydrolyzed by RNases. Second, it hybridizes with the complementary sense DNA and hence was expected to inhibit the biosynthesis of polymerase in DHBV. Third, it inhibits the enzyme activity of human immunodeficiency virus (HIV) reverse transcriptase (RT).

Nine ducks were infected with DHBV intravenously, and their PCR products were loaded on a polyacrylamide gel, in lanes 2–10 (FIG. 11). Lane 1 was a sample treated identically as those from the infected ducks, except that it was derived from an uninfected duck. Lane M is a molecular size ladder, and lane P is a positive control. The bands present at 214 bp represents the PCR produce of the DHBV.

Subsequently, the presence of DHBV PCR products after treatment was determined (FIG. 12a). Each infected duck was treated with either 0.5 mg/kg (lanes 2–6) or 1.0 mg/kg (lanes 7–10) of the DNP-antisense oligoribonucleotide against DHBV (Compound VII). Lane C is a negative control (PCR reagents only), lane 1 is from an uninfected duck, lane M is a molecular size ladder, and lane 11 is the PCR positive control. FIG. 12a shows that after 2 weeks of treatment, the intensity of the PCR product at 214 bp is of lower intensity in several of the ducks, with reduced intensity present for the animals treated with 1.0 mg/kg. Ten weeks after termination of treatment (FIG. 12b), the intensity of the PCR product in animals 8 and 9 is not visible, the intensity of the band in lane 10 is reduced compared to the same animal at 2 weeks, whereas the positive control in lane P is present with the same intensity as in FIG. 12a.

Example VII

Oligoribonucleotides of The Invention Effectively Treat Avian Hepatitis II

In another study to determine the therapeutic efficacy of the oligoribonucleotides of this invention, a sequence of the DHBV gene (nucleotide positions 2468–2487) was selected as the target sequence. This sequence is completely different from the sequence used in the previously described study (Example VI). The complementary antisense DNP-derivatized oligoribonucleotide (Compound VIII) used in this study had the sequence:

5'-ggguguaugg aaaagccguc-3'           (SEQ ID NO: 10).

For one control (Compound IX), the sense sequence chosen was:

5'-gacggcuuuu ccauacacc-3'            (SEQ ID NO: 11)

(nucleotide positions 2469–2488). An additional control (Compound X) consisted of the random sequence:

5'-gggauucugu cagucgguac-3'           (SEQ ID NO:12), which is not complementary to any sequence of DHBV.

A single naturally DHBV-infected duck, which was shown to have DHBV DNA in its blood, was used as the sole source of DHBV in all experiments. The serum from this duck was injected into the leg muscles of 30 ducklings. Viremia became detectable by day 5 after the inoculation. Only 1 out of the 30 ducklings lost its virus spontaneously by day 20. One duck which has been kept for 20 months still has its virus. All the other ducks were sacrificed for autopsy after the viremia had been followed for 3 months.

Fifteen days after inoculation with DHBV, all the ducks showed positive viremia as detected by PCR method (FIG. 13a, lanes 1–15; lane M is a molecular size ladder and lane P is a positive control). The ducks were randomly assigned to three groups for treatment with different poly-DNP-RNAs: 9 ducks were treated with antisense oligoribonucleotide to 2468–2487 (Compound VIII) (A), 4 ducks were treated with sense oligoribonucleotide Compound IX (S) and 2 ducks were treated with random sequence oligoribonucleotide Compound X (R). Starting from the 16th day after inoculation, each group of ducks received poly-DNP-RNA with either antisense, sense, or random sequence by intravenous injection via foot veins at a daily dosage of 1 mg/kg. Blood samples were collected every five days for DHBV detection. After 15 days of treatment, viremia began to disappear in the antisense group treated with Compound VIII. After 25 days of treatment, none of the nine ducks treated with antisense poly-DNP-RNA (Compound VIII) showed viremia, while three out of four ducks in sense group still had viremia and both ducks in random group also showed persistent viremia (FIG. 13b, lanes 1–15; lane M is a molecular size ladder and lane P is a positive control). After 25 days, the dosage was decreased to 0.5 mg/kg for another 20 days for maintenance. None of the ten ducks had virus re-emergence after another thirty days follow-up. Of the two ducks from the antisense group kept for an additional 8 months for follow-up, neither of them showed re-emergence of viremia 8 months after the termination of treatment (FIG. 13c, lanes 14, 15; lane M is a molecular size ladder and lane P is a positive control).

Recently Offensperger et al. (Offensperger et al., *EMBO Journal* 12, 1257–1262 (1993); Offensperger *Nature Biotechnology: Antisense* 97:26 (1997)) reported the treatment of viremia in DHBV-infected ducks with an antisense PS-DNA by daily administration of 20 mg/Kg for 8 weeks. However, the virus returned after a remission of 26 weeks. In contrast, the oligoribonucleotides of this invention are effective in concentrations as low as 0.5 mg/Kg, or about 40 times lower than the PS-DNA used by Offensperger et al. Even at a concentration of 0.5 mg/Kg, the oligoribonucleotides of this invention unexpectedly prevented the recurrence of viremia, even after 36 weeks after cessation of treatment.

In another set of experiments, eight infected ducks were treated after detection of viremia and one was left for control, using the same protocol dosage as in the previous experiments. After 25 days of treatment with antisense Compound VIII, DHBV was no longer detectable in the blood of any of the treated ducks. However, DHBV persisted for at least another ten days in the liver samples. Results are shown in FIG. 14. Lane M is a molecular size ladder and lane N is a negative control from an uninfected duck. Lane 1 is a liver sample from infected but untreated duck. Lanes 2–9 are from infected ducks treated with antisense poly-DNP-RNA (Compound VIII) and sacrificed after 25, 30, 35, 40, 55, 70, and 95 days, respectively, from the beginning of treatment. Lane P is a positive control. Histological conditions of the ducks is shown in FIGS. 15A–15F, which shows six hematoxylin-eosin stained slides of liver photographed at 640× magnification. The normal uninfected duck was killed at the same time as the first infected, untreated duck (FIG. 15B), had normal histological appearance (FIG. 15A). FIG. 15B clearly shows diffuse fatty change in its swollen hepatocytes. The hepatic sinuses were compressed and there was obvious mononuclear cell infiltration around central vein areas. After 25 days of treatment with the antisense oligoribonucleotide of this invention (Compound VIII; FIG. 15C), the fatty change of the hepatocytes improved and became localized near central vein areas. The viremia of this duck had disappeared, but viral DNA could still be detected in the liver homogenate. After 45 days of treatment (FIG. 15D), there were still localized fatty changes and moderate inflammatory cell infiltration around the central vein area, though PCR assay showed no DBV DNA in either blood or liver. Ten days after the end of treatment (55 days after the beginning of the treatment; FIG. 15E), the liver almost returned to normal with only a trace of mononuclear cell infiltration. Fifty days after stopping treatment (90 days after the beginning of treatment; FIG. 15F), the liver appeared completely recovered from the infection.

These studies represent the first demonstration of the unexpectedly complete reversal of hepatitis B infection in vivo. Moreover, these studies are also the first demonstration of a complete recovery of an animal's liver after infection by hepatitis B virus. None of the prior art oligoribonucleotides have produced such a therapeutic efficacy in vivo.

Example VIII

Design of Antisense Oligonucleotide to Duck Hepatitis B Virus (DHBV) m 1.1 Introduction In a third study of DHBV, we selected portion of the sequence, from base 798 to base 813, at the initiation site of the pre-S gene. Offensberger et al. *EMBO J.* 12:1257–1262 (1993), incorporated herein fully by reference, showed that the phosphorothioate modified antisense corresponding to bases 795 through 812 inhibited the replication of HBV in ducks (DHBV). The selected sequence is as follows:

5'-cugaugggac aacaa-3'     (SEQ ID NO: 13).

A 15-mer antisense oligonucleotide was designed to block the synthesis of HBV. The oligoribonucleotide has the following sequence:

5'-uuguuguccc aucag-3'     (SEQ ID NO: 14).

The antisense oligoribonucleotide is ordered from, and custom synthesized by, Oligo Therapeutics, Inc.

1.2 Preparation Of DNP-derivatized Antisense Oligonucleotide

In order to derivatize the antisense oligonucleotide described above, the oligoribonucleotide of SEQ ID NO: 14 is reacted with 1-fluoro-2,4-dinitrobenzene as described above to produce Compound XI.

1.3 Antisense Treatment of Duck (Avian) HBV

Approximately 25% to 30% of all ducklings are naturally infected with HBV. Ducks testing positive for HBV by RT-PCR and ducks testing negative for HBV will be used to test the effectiveness of the antisense therapy. Ducks can be obtained from Metzer Farms, Gonzales, Calif. A similar experimental design is used as was used in Example VII.

It is expected that ducks testing positive for HBV that are not treated with Compound XI, the derivatized antisense oligonucleotide of SEQ ID NO:14 will continue to be infected while ducks testing positive for HBV that are treated with the derivatized antisense oligonucleotide of SEQ ID NO: 14 will cease to be infected.

As reported by Offensberger et al. *EMBO J.* 12:1257–1262 (1993), infected ducklings were treated with daily intravenous injections of the phosphorothioate modified antisense DNA and the effective dosage was found to be 20 mg/kg. It is expected that the effective concentration of the present antisense oligonucleotides will be much lower than Offensberger et al. because of the enhanced membrane permeability and stability of nucleotides derivatized in accordance with the invention. In the present experiment, dosing will be started at 0.2 mg/kg and will be scaled up in the range of 0.2 mg/kg to less than about 20 mg/kg to determine efficacy. It is expected that efficacy will be apparent in the range of about 1 mg/kg to about 10 mg/kg and may well be apparent in the same range as that observed for the other sequences of DHBV described above in Examples VI and VII.

Example IX

Treatment of Human Breast Cancer Cells In Vitro I

In another embodiment of this invention, poly DNP-derivatized oligoribonucleotides with antisense sequences specific for human breast cancer genes.

A. Introduction

Overexpression of cellular genes such as protein kinase A (PKA) has been strongly implicated in the pathogenesis of several cancers. There are two types of protein kinase A, which share the homologous catalytic (C) subunits and different regulatory (R) subunits. Four distinct R subunits, RIα, RIβ, RIIα, and RIIβ have been identified (Taylor et al., *FASEB J.* 2:2677–2685 (1988), incorporated herein by reference). The complete nucleic acid sequence of PKA is known (Sandberg et al., *Biochem. Biophys. Res. Commun.* 149:939–945 (1987), incorporated herein fully by reference). Recent studies demonstrated that the overexpression of RIα subunit of PKA is associated with the cell proliferation while the RIIβ subunit of PKA induces the differentiation of cells (Cho-Chung et al., *Antisense Nucleic Acid Drug Develop.* 7:217–223 (1997), incorporated herein fully by reference).

An example of a specific oncogene involved in tumorogenesis is the erbB-2 oncogene, whose complete nucleotide sequence is known (Yamamoto et al., *Nature* 319:230–234 (1986), incorporated herein fully by reference. The erbB-2 oncogene encodes a 185 kD transmembrane receptor with tyrosine kinase activity. Amplification and overexpression of erbB-2 takes place in many types of cancers and is overexpressed in about 25%–30% of breast cancer patients. Amplification of the erbB-2 gene is linked with tumor cell metastasis, shortened survival time of patients with breast cancer, and adverse prognosis (Lofts et al., *Cancer Treatment and Research* 61:161–179 (1992), incorporated by reference). In vitro and in vivo assays also suggest that the overexpression of erbB-2 results in the neoplastic transformation of normal cell lines (DiFiore et al. *Science* 237:178–182 (1987); Muller et al. *Cell* 54:105–115 (1988), both incorporated by reference). Several phosphorothioate oligodeoxynucleotides complementary to the translation initiation site of the erbB-2 gene were found to be susceptible to antisense inhibition of the production of the erbB-2 protein (Vaughn et al., *Nucleic Acids Res.* 24:4558–4564 (1996) incorporated by reference).

Based on these observations, two types of antisense poly-DNP-RNAs corresponding to the RIα/PKA gene and the erbB-2 gene, respectively, were designed and synthesized.

B. Materials and Methods 1.1 Cell Lines

The experiments were performed on two human breast cell lines. SK-Br-3 is a human breast cancer cell line characteristic of human breast cancer. They were purchased from ATCC (American Type Culture Collection, Rockville, Md.). The cells were stored in DMEM/F12 medium (Gibco BRL, Grand Island, N.Y.) with 10% fetal bovine serum and 10% glycerin. A sample of SK-Br-3 cells was thawed at room temperature and plated in RPMI 1640 medium (Gibco BRL) supplemented with 10% fetal bovine serum. The cells were incubated at 37° C. in a humidified atmosphere of air containing 5% $CO_2$, and was subcultured once every week.

MAF-10A cells were obtained from Barbara Ann Karmanos Cancer Institute (Detroit, Mich.) and maintained in the DMEM/F12 medium containing 5% horse serum, insulin (10 μg/ml) (Sigma, St. Louis, Mo.), EGF (20 ng/ml), cholera toxin (100 ng/ml) (Gibco BRL), and hydrocortisol (0.5 μg/ml). The medium was changed every 5 days and cells were passaged after detaching them with trypsin solution (0.5% trypsin and 0.53 mM EDTA in PBS) every 10 days. MAF-10A cells have the characteristics of normal breast epithelial cells (Soule et al. *Cancer Research* 50:6075–6080 (1990) incorporated by reference).

1.2 Synthesis of Oligoribonucleotides

Four oligoribonucleotides were synthesized by in vitro transcription and were derivatized to manufacture corresponding DNP oligoribonucleotides.

5'-gggcgugccu ccucacugg c-3'    (SEQ ID NO:15)

is antisense to the RIα/PKA gene (derivatized to form Compound XII).

5'-gggugcucac ugcggcuccg ggc-3'    (SEQ ID NO:16)

is antisense to the erbB-2 gene (derivatized to form Compound XIII).

5'-gggaucguuc agagucua-3'    (SEQ ID NO: 17)

is a random sequence control (derivatized to form Compound XIV).

5'-gggccaguga ggaggcacgc-3'    (SEQ ID NO:18)

is a sense control for SEQ ID NO: 15, (derivatized to form Compound XV).

1.3 In Vitro Transcription

The templates with T7 promoter for in vitro transcription were purchased from IDT (Integrated DNA Technologies, Coralville, Iowa). The method of in vitro transcription was described previously (Milligan et al. *Nucleic Acids Research* 15: 8783–8798 (1987), incorporated herein fully by reference). The reaction was run in 50 mM Tris buffer (pH 8.1), 5 mM dithiothreitol, 1 mM spermidine, 0.2 μg/μl BSA, 25 mM MgCl$_2$, 5 mM NTPs, 20 μg/ml DNA template, 0.2 U/μl RNase inhibitor (Amersham, Arlington Heights, Ill.), 2 U/ml pyrophosphates (Sigma), 2 U/μl T7 RNA polymerase (Promega, Madison, Wis.). The reaction mixtures were incubated at 37° C. for 6 hours. After digestion with DNase I, the reaction mixtures were extracted with phenol and chloroform and precipitated with ethanol. The yield of the RNA product was determined by running 16% urea denaturing PAGE.

1.4 Derivatization of RNA

The RNA was derivatized as described (Kang et al. *J. Biol. Chem.* 269:12024–12031 (1994), incorporated herein fully by reference). 1 mg of RNA was dissolved in 750 μl of water and mixed with 125 μl of buffer solution (2 M KHCO$_3$, 0.1 M K2CO$_3$, pH 8.8). Thereafter, 375 μl of acetone containing 50 μl of 1-fluoro-2,4-dinitrobenzene (FDNB) was added to the reaction mixtures. The reaction was incubated at 35° C. for 24 hours, and the pH was maintained around 8.8. After that, the reaction was kept at room temperature for another 24 hours and extracted with phenol/chloroform. The resulting mixture was dialyzed against water for 3 days to remove unreacted FDNB. The ration of DNP/RNA and the actual concentration of poly-DNP-RNA was calculated from the observed absorbance at 260 nm and 330 nm, because the oligonucleotides absorb only at 260 nm, while the DNP absorbs at both 260 and 330 nm.

1.5 Cell Growth Assay

About $2 \times 10^4$ cells were plated on 30 mm culture dishes one day before the treatment with the antisense poly DNP-RNAs. Each culture received one dose of poly-DNP-RNA at the start of the experiment, and another dose 24 hours later. After incubation for 8 days, the cells were collected and counted using a Coulter counter and viability was determined using Trypan Blue. All samples were run in quadruplicate.

1.6 Colony Formation Assay

SK-Br-3 cells were exposed to poly-DNP-RNA at different concentrations for two days. After incubation, the cells were washed with PBS twice and plated at $2 \times 10^4$ cells/dish in methylcellulose containing 10% fetal bovine serum (StemCell Technologies, Vancouver, B.C., Canada). Cells were incubated for 9 days at 37° C. in air containing 5% CO$_2$. Colonies containing more than 16 cells were counted. All samples were run in triplicate.

1.7 Reverse Transcriptase-PCR

The total RNA was extracted according to the protocol of Molecular Research Center, Inc. (Cincinnati, Ohio). The collected cells were mixed with TRI REAGENT vigorously and extracted with chloroform. The aqueous phase was precipitated with isopropanol and washed with 75% ethanol. The subsequent reverse transcription was carried out in the presence of 1 μM oligo (dT$_{15}$) primer, reaction buffer (Promega), 1 mM MgSO$_4$, 0.2 mM dNTP and 0.1 U/μl AMV reverse transcriptase. The reaction was run at 48° C. for 45 minutes. About ⅟₅₀ of the mixture containing the cDNA from the reverse transcription reaction was amplified using PCR in a final volume of 50 μl. The PCR reaction was performed as described with some modification (Biernaux et al. *Blood* 86:3118–3122 (1995), incorporated herein fully by reference). The 30 cycles of the PCR (1 minute at 94° C., 1 minute at 60° C., and 1 minute at 72° C.) were preceded by 2 minutes of denaturation and followed by 5 minutes of elongation at 72° C., using β-actin as an internal control (Nakajima-Iijima et al. *Proc. National Acad. Sci. USA* 82:6133–6137 (1985), incorporated herein fully by reference).

1.8 TUNEL Assay

When apoptosis and cell death occurs, the nuclear DNA becomes digested, resulting in increased numbers of DNA molecules in the cells. The increased numbers of DNA molecules can be detected using the TdT-mediated dUTP Nick-End Labeling (TUNEL) method, in which a fluorescent label is attached to the free ends of the DNA using terminal deoxynucleotidyl transferase. As apoptosis proceeds, the number of free ends of DNA increases, more fluorescent label can be added to the DNA, and the increased amount of bound label can be detected using a fluorescent microscope. Thus, as apoptosis occurs progressively, the amount of fluorescence observed in cells increases.

To use the TUNEL assay, after their treatment with poly-DNP-RNA for 3 days, the cells were fixed with 4% formaldehyde and washed with PBS twice. Then the fixed cells were permeabilized with 0.2% Triton X-100 (Sigma) solution in PBS for 10 minutes on ice. After rinsing with PBS twice, the samples were subjected to TUNEL staining, using Apoptosis Detection System (Promega) with fluorescein-12-dUTP at 37° C. for 1 hour, which adds fluorescein to the 3'-OH ends of fragmented DNA. The reaction was stopped with 2× SSC solution, and the background was stained with 1 μg/ml propidium iodide (Promega). The green apoptotic signal was detected by fluorescent microscopy in a red background.

C. Results 1.1 Poly-DNP Antisense oligoribonucleotides After derivatization of the in vitro transcription-synthesized RNAs, the following four purified compounds were tested on SK-Br-3 cells and on MCF-10A cells:

Compound XII

Poly-DNP (5'-gggcgugccu ccucacugg c-3')

(antisense to RIα/PKA gene);
Compound XIII

Poly-DNP (5'-gggugcucac ugcggcuccg ggc-3')

(antisense to erbB-2 gene);
Compound XIV

Poly-DNP (5'-gggaucguuc agagucua-3')

(random control sequence);
Compound XV

Poly-DNP (5'-gggccaguga ggaggcacgc-3'

(sense control for the sequence of compound XII for the RIα/PKA gene).

1.2 Inhibition of SK-Br-3 Cell Proliferation by the Antisense Poly-DNP-RNAs

We studied the effect of antisense poly-DNP-RNA on the growth of two human breast cell lines, the breast cancer cell line SK-Br-3 (FIG. 16), and the nontumorigenic breast cell MAF-10A (FIG. 17). The SK-Br-3 cells were incubated for 8 days with Compound XII (anti-RIα/PKA) and Compound XIII (anti-erbB-2) antisense DNP-RNAs, respectively. Filled columns (■) represent the cell numbers in the culture dishes at the beginning of the experiment, and open columns (□) represent the cell numbers in the culture dishes after 8 days of exposure to control or antisense oligoribonucleotides. Data is expressed as mean±standard deviation; n=4 each.

After 4 days of treatment with poly DNP-RNAs, the SK-Br-3 cells became detached form the culture dishes. After 8 days of the study (FIG. 16), untreated cells (Cell only) or cultures treated with the Compound XIV (Random sequence) grew so that an average of greater than $35 \times 10^4$ cells were present. In cultures treated with the antisense RIα/PKA Compound XII (PKA) at a concentration of below 5 μg/ml, there was no observable inhibition of cell growth. However, at concentrations of 10 μg/ml and above, there was progressive inhibition, with complete inhibition of cell growth at a concentration of 40 μg/ml, so that the cells failed to grow after initial plating. The $IC_{50}$ of this inhibitory effect is below 10 μg/ml. Moreover, increasing the concentration to 80 μg/ml actually killed the SK-Br-3 cells, reducing the cell number to nearly zero.

In contrast with the striking inhibition of cell growth by PKA antisense inhibitor, Compound XV (Sense PKA) was ineffective at inhibiting the growth of SK-Br-3 cells at concentrations up to 80 μg/ml; the average cell numbers were above $35 \times 10^4$. The finding that the sense strand of PKA inhibitor had no effect indicates that the inhibition due to the antisense DNP PKA inhibitor was due to specific inhibition of the transcription of the mRNA of the RIα/PKA gene in the cells.

This concentration dependent inhibition with an $IC_{50}$ of below 10 μg/ml is unexpectedly more potent than any previously described antisense inhibitor of any oncogene. Furthermore, the finding that Compound XII actually killed the breast cancer cells is completely unexpected, based on any prior study.

Similarly to inhibition of the RIα/PKA gene, inhibition of the erbB-2 gene by Compound XIII (anti-erbB:2) was very effective at inhibiting growth of SK-Br-3 cells. At concentrations above about 10 μg/ml, there was a concentration-dependent decrease in cell numbers, with nearly complete inhibition of cell growth observed at 80 μg/ml. The $IC_{50}$ was about 15 μg/ml. Thus, the inhibition of erbB-2 by the poly-DNP-antisense RNA was unexpectedly more potent than any previously studied inhibitor.

1.3 Lack of Inhibition of Normal Breast Cell Growth By Poly-DNP-Antisense RNAs

In contrast with the concentration-dependent, complete inhibition of growth of breast cancer cells observed with the antisense inhibitors, the same oligoribonucleotides had no observable effects on non-tumorigenic cells (FIG. 17). Filled columns (■) represent the cell numbers plated at the beginning of each study. Open columns (□) represent the cell numbers observed after treatment with the oligoribonucleotides of this invention.

Treatment of MAF 10-A cells using any of the oligoribonucleotides of this invention or any control oligoribonucleotides resulted in no change in cell number in any experiment (FIG. 17). Thus, the inhibition of growth of the SK-Br-3 cells was due to a specific antisense effect to decrease the expression of the oncogenes in the cancer cells, and was not due to any non-specific metabolic effects on cells generally.

1.4 Effect of Poly-DNP-RNA on Colony Formation of Breast Cancer Cells

To further examine the efficiency and specificity of the antisense poly-DNP-RNA on cancer cell growth, we studied the formation of colonies of cancer cells in semi-solid growth medium. Colonial growth of cells lines in semi-solid medium has been used widely to study the characteristics of tumor cells and their sensitivity to anticancer agents. Because malignant cells lose the anchorage dependence of growth and acquire the ability to grow in semi-soft medium, we employed methylcellulose medium to assess the anticancer activity of both RIα/PKA and erbB-2 antisense poly-DNP-RNAs on the SK-Br-3 cell line.

SK-Br-3 cells were exposed to poly-DNP-RNAs at the concentrations shown for 2 days. Each culture received one dose of the poly-DNP-RNA at the start and another dose 24 hours later. After incubation, the cells were washed with PBS and plated at $2 \times 10^4$ cells /dish in FBS containing methylcellulose. The cells were subsequently incubated for 9 days at 37° C. in air containing 5% $CO_2$. Colonies containing more than 16 cells were counted.

FIG. 18 is a graph showing the number of SK-Br-3 colonies as a function of concentration of poly-DNP-RNAs of this invention. The number of colonies which formed in dishes without any treatment was 590, which is represented by a point at 0 concentration of Poly-DNP-RNA.

Treatment of SK-Br-3 cells with the random-sequence (Compound XIV; ♦) resulted in no inhibition of colony formation. However, treatment of SK-Br-3 cells with either Compound XII, anti-RIα/PKA (PKA), ▼; Compound XIII, anti- erbB-2, (erbB-2), ■; or the combination of PKA and erbB-2 together (x) resulted in concentration-dependent decreases in the numbers of colonies formed. At a concentration of 80 μg/ml for each inhibitor, the inhibition was nearly complete, with less than about 100 colonies formed. This represents inhibition of over 80%. The IC$_{50}$s of the inhibition were about 27 μg/ml for anti-PKA and anti-erbB-2 alone, and was about 21 μg/ml for the combination of PKA and erbB-2 together. In contrast with the inhibition by the antisense oligoribonucleotides of this invention, Compound XV (sense sequence) had no effects on colony growth.

1.5 Effect of Antisense Inhibitors on Specific RNA Expression

To determine whether antisense inhibitors of this invention decreased RNA expression in SK-Br-3 cells, we measured specific mRNAs for β-actin, RIα/PKA and erbB-2 using a reverse transcriptase polymerase chain reaction (RT-PCR) method. mRNAs for β-actin, RIα/PKA and erbB-2 were amplified by their respective primers and the relative concentrations of the corresponding cDNAs were estimated by comparing the intensities of ethidium bromide-stained bands in the same 1.5% agarose electrophoresis gel (FIG. 13).

The left lane of FIG. 19 shows molecular size markers. Lanes 1–3 show SK-Br-3 cells without any treatment and whose RNAs were amplified with β-actin, RIα/PKA and erbB-2 primers, respectively. Lanes 4–6 show SK-Br-3 cells treated otherwise identically with those shown in Lanes 1–3 except for the addition of Compound XII (antisense RIα/PKA). The absence of a band in Lane S reflects PKA mRNA being reduced to undetectable levels by the antisense treatment. Lanes 7–9 show SK-Br-3 cells treated otherwise identically with those shown in Lanes 1–3 except for the addition of Compound XIII (antisense-erbB-2). The absence of a band in Lane 8 reflects erbB-2 mRNA being reduced to undetectable levels by the antisense treatment. The inhibition of RNA transcription was specific because antisense-PKA did not inhibit erbB-2 mRNA expression (Lane 6), and antisense-erbB-2 did not inhibit PKA mRNA expression (Lane 9). In contrast to the inhibitory effects of Compounds XII and XIII, Compound XIV (random sequence) and Compound XV (sense PKA sequence) had not effect on mRNA expression (data now shown).

1.6 Antisense oligoribonucleotide Killed Breast Cancer Cells

Figure 20:
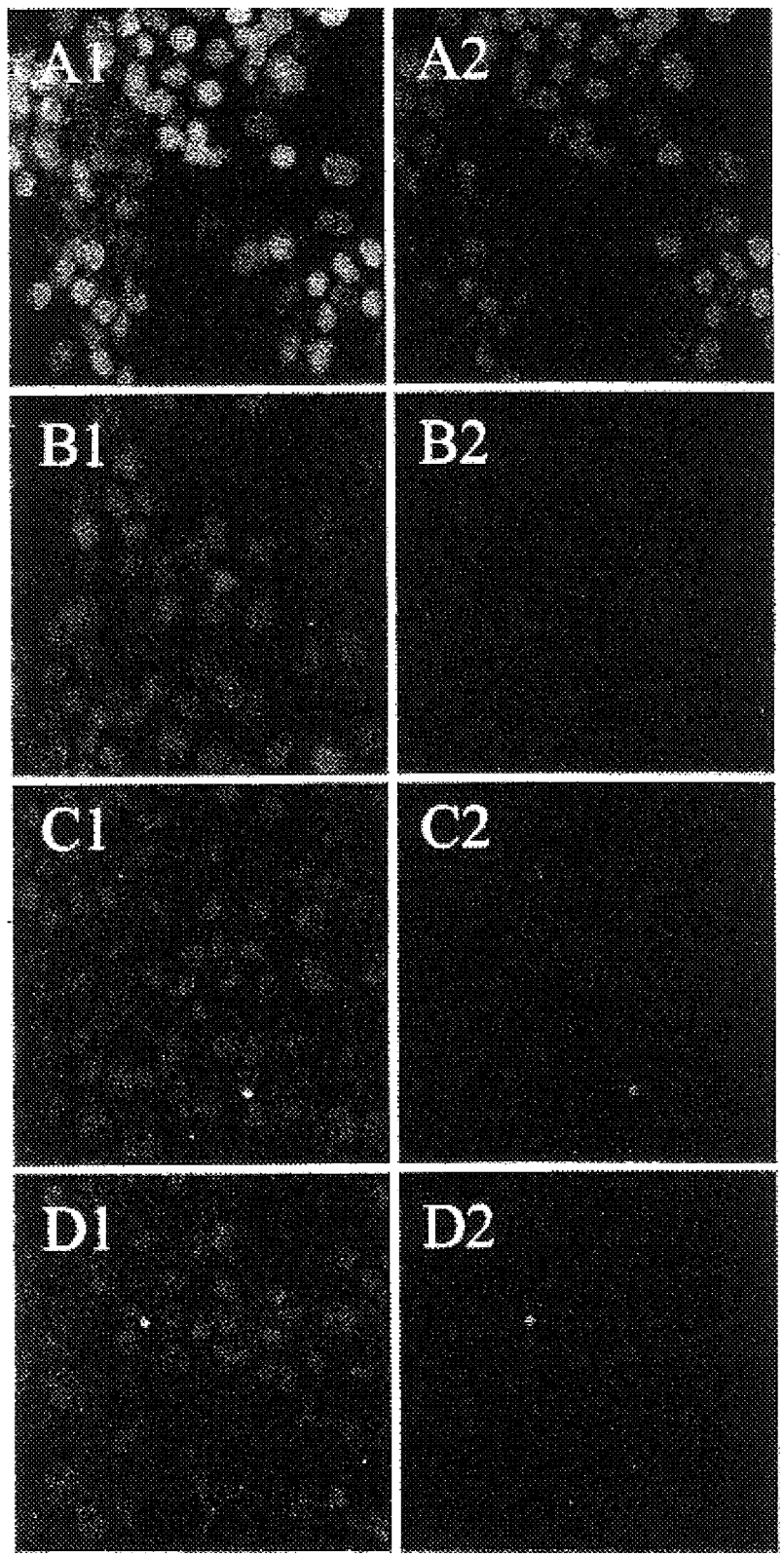

As shown above in FIG. 16, the antisense poly-DNP-PKA oligoribonucleotide (Compound XII) at a concentration of 80 μg/ml decreased the numbers of SK-Br-3 cells compared to controls. To determine whether the decreased cell number was due to cell killing, we measured apoptosis using the TUNEL assay. The methods for this assay were described in section 1.8 above. FIG. 20 shows photographs of cells labeled with fluorescein-12-dUTP either before or after treatment.

The photomicrograph shown in panel A1 of FIG. 20 shows SK-Br-3 cells which had been treated with 80 μg/ml Compound XII (antisense PKA). The photomicrograph was taken through a red filter, showing the presence of numerous fluorescent cells, indicating apoptosis. Panel A2 shows a photomicrograph taken through a green filter of the same field as shown in A1. The absence of detectable signal in panel A2 means that the signal detected in panel A1 was specific for fluorescein. Compounds XIV (random sequence) and XV (sense PKA sequence) did not increase the amount of fluorescence observed in similarly treated cultures (data not shown).

The photograph shown in panel B1 of FIG. 20 shows untreated SK-Br-3 cells exhibiting no detectable fluorescence, indicating little if any apoptosis. The photograph was taken through a red filter. The photograph shown in panel B2 of the same field as in panel B1, but taken through a green filter also shows no detectable label. Similarly, SK-Br-3 cells treated with Compounds XIV (random sequence) or XV (sense PKA sequence) exhibit no fluorescence (data not shown).

The photograph, taken through a red filter shown in panel C1 of FIG. 20, shows that treatment with 80 μg/ml Compound XII (antisense PKA) does not induce apoptosis in normal, MAF-10A cells. The photograph taken through a green filter shown in panel C2 of the same field as that shown in panel C1 shows no fluorescence. Similarly, Compounds XIV (random sequence) and XV (sense PKA sequence) do not induce apoptosis (data now shown).

The photographs shown in FIG. 20 in panels D1 (taken through a red filter) and D2 (taken through a green filter) show untreated MAF-10A cells. Neither of these photographs show any fluorescence, indicating that little, if any apoptosis occurred.

Example X

Treatment of Murine Leukemia Virus In Vitro III

In another study to determine the effects of the oligoribonucleotides of this invention on cancer cells, we selected another series of antisense oligoribonucleotides and tested them on a different human cancer cell line, BV173 cells, a murine leukemia cell line. The inhibitory effects of the oligoribonucleotides of this invention are similar on BV173 cells as they are on SK-Br-3 cells.

A. Introduction

Antisense thiolated oligoribonucleotides have been used by many investigators as anticancer agents. They can suppress cancer cell growth but have quite high toxicity. In the majority of patients with chronic myelogenous leukemia (CML) a cellular oncogene is activated by chromosomal translocation involving the Philadelphia (Ph) chromosome. This Ph translocation results in the activation of the abl gene downstream of the bcr promoter which is unique to CML (Skorski et al., *Proc. Natl. Acad. Sci. USA* 91:4504–4508 (1994)). Recent studies also show that the expression of RIα subunit of protein kinase A (PKA) was increased in many human cancer cell lines and in primary tumors. Overexpression of the RIα subunit of PKA is associated with cell proliferation, in competition with the expression of the RIIβ subunit of PKA which induces the differentiation of cells (Tortora et al., *Cell Growth & Differentiation* 5:753–759 (1994)).

B. Methods

Based on these observations, we designed, synthesized and tested three separate dinitro-phenyl-derivatized oligonucleotides for suppressing the bcr-abl gene and the RIα/PKA gene, respectively.

1.1 Selection of Antisense Sequences

Studies were carried out in fashions similar to those described above for the SK-Br-3 cells in Example IX. The sequences selected included:

5'-gggucucuca ggucgagc-3'     (SEQ ID NO: 19)

(Compound XVI; anti-RIα/PKA);

5'-gggcuucuuc cuuauuga-3'     (SEQ ID NO:20)

(Compound XVII; anti bcr-abl); an inhibitor comprising two antisense sequences:

5'-gggcuucuuc cuuauugaug ggucucucag gucgagc-3' (SEQ ID NO:21)

(Compound XVIII; anti bcr-abl-anti-RIα/PKA); and

5'-gggaucguuc agagtcta-3' (SEQ ID NO:22)

(Compound XIX; random sequence).

1.2 Inhibition of Cell Growth

Cultures of BV173 cells were exposed to control medium in the absence of any antisense nucleotides (Cell only), the random oligoribonucleotide sequence (Compound I; Random), or anti-PKA (Compound XVI; PKA), anti-bcr-abl (Compound XVII; bcr/abl), the bifunctional inhibitor (Compound XVIII; Bifunction), the combination of anti-PKA and anti-bcr-abl together (PKA+bcr-abl) in the concentrations indicated. The number of cells at the beginning of the study are indicated by filled columns (■), and the number of cells after treatment for 9 days is indicated by hatched columns in FIG. 21.

1.3 Inhibition of Growth in Semi-Solid Medium

To determine the concentration dependence of the inhibitory effect, BV173 cultures were incubated in the absence of antisense oligoribonucleotides, in the presence of random sequence (Compound XIX), anti-bcr-abl (Compound XVII), anti PKA (Compound XVI), the bifunctional antisense inhibitor (Compound XVIII), or the combination of anti-PKA and anti-bcr-abl nucleotides together. Each culture was seeded with $4 \times 10^4$ cells and was exposed to poly-DNP oligoribonucleotides at the concentrations indicated for two days. Each culture received the oligoribonucleotide at the start of the study and 24 hours later. After incubation, cells were washed with PBS and plated at $2 \times 10^4$ cells/dish in methyl cellulose as described in Example IX.

C. Results

1.1 Cell Growth

FIG. 21 shows the results of the studies described on the effects of antisense oligoribonucleotides on cell growth. With either no antisense oligoribonucleotide ("Cell only") or a random sequence oligoribonucleotide, Compound XIX ("Random"), no inhibition of cell growth occurred. In contrast, the DNP-derivatized oligoribonucleotide specific for RIα/PKA (PKA) and a DNP-derivatized antisense oligoribonucleotide (Compound XVII) specific for the bcr-abl oncogene (bcr/abl), each completely inhibited cell growth at concentrations of 20 µg/ml or higher. A multifunctional inhibitor containing the anti-RIα/PKA sequence and the anti bcr-abl sequence together (Compound XVIII; Bifunction), also completely inhibited cancer cell growth at a concentration of 20 µg/ml, and in fact, killed the cells. Moreover, the combination of anti-PKA plus anti-bcr-abl inhibitors (PKA+bcr-abl) inhibited cancer cell growth in a concentration-dependent fashion.

1.2 Inhibition of Colony Formation in Semi-Solid Medium

FIG. 22 shows the dose-inhibition relationships for the inhibitors used in FIG. 21. Random sequence antisense oligoribonucleotides (Compound XIX; Random ◇) did not inhibit colony formation in semi-solid medium. In contrast, the DNP-derivatized anti-RIα/PKA sequence (Compound XVI; PKA) and the DNP-derivatized anti-bcr-abl sequence (Compound XVII; bcr-abl) each inhibited colony formation with $ED_{50}$s of about 15 µg/ml, or about 2.4 µM. The multifunctional inhibitor containing both sequences in the same oligoribonucleotide (Compound XVIII; bifunctional X) also inhibited cancer cell colony formation with and $ED_{50}$ of about 15 µg/ml. A mixture of individual antisense oligoribonucleotides specific for anti-RIα/PKA and anti-bcr-abl ("bcr-abl plus PKA") also inhibited cancer colony formation with an $ED_{50}$ of about 20 µg/ml for each oligoribonucleotide. Not only did the specific antisense oligoribonucleotides inhibit cancer colony formation, they actually killed the cancer cells (FIG. 21).

In summary of the above section on cancer cells, the studies described above show that growth of cancer cells in vitro can be inhibited in a concentration-dependent fashion by the derivatized oligoribonucleotides of my invention. The discovery of the selective killing of cancer cells by the oligoribonucleotides of this invention shows that these compounds are superior to the prior art antisense oligoribonucleotides. None of the prior art oligoribonucleotides have been shown to selectively kill cancer cells. Moreover, the concentrations of the derivatized oligoribonucleotides of my invention necessary to inhibit cancer cell growth in vitro can be in much lower concentrations than the prior art antisense oligoribonucleotides made according to prior art methods.

Example XI

Antisense Inhibitors Specific for Human Immunodeficiency Virus (HIV)

A. Introduction

Because HIV is a retrovirus, we designed an antisense inhibitor with the capability of inhibiting three aspects of HIV. First, the poly DNP nucleotides are inhibitors of reverse transcriptase, including that of HIV. Second, inhibitors of the tat gene have been used in designing a genetic treatment for HIV-infected tissue (Biasolo et al., *J. Virology* 70:2154–2161 (1996), incorporated herein fully by reference). Third, an anti-gag sequence has been used since 1992 for the inhibition of HIV-infected cells using a phosphorothioate oligodeoxynucleotide (PS-OLIGONUCLEOTIDE) under the name GEM 91 (Agrawal et al., *Antisense & Nucleic Acid Drug Development* 7:13–22 (1992), Liszicwicz et al., *Proc. Natl Acad. Sci USA* 91: 7942–7946 (1994), both references incorporated herein fully by reference).

1.1 Design of Anti-HIV Inhibitor

Using the same strategy as described for MuLV and breast cancer, new derivatized inhibitors of human immunodeficiency virus (HIV) were designed and tested. We selected to manufacture four antisense inhibitors, one containing a sequence complementary to the tat gene, two containing sequences complementary to regions of the gag gene, and a multifunctional inhibitor containing two sequences, one complementary to the tat gene and one complementary to the gag gene. The antisense sequences chosen were:

5'-ggcucucgca cccaucucuc uccuucu-3' (SEQ ID NO:23)

(27-mer; anti-gag sequence 1),

5'-ggcacccauc ucucuccuuc ua-3' (SEQ ID NO:24)

(22-mer; anti-gag sequence 2), and

5'-gggaaacaaa cuuggcaaug aaa-3' (SEQ ID NO:25)

(23-mer; anti-tat).

A phosphorothioate oligodeoxynucleotide (PS-DNA) containing the anti-gag sequence 1 has been shown to be an inhibitor of HIV infection in vitro and in vivo (Agrawal et al, *Antisense & Nucleic Acid Drug Development* 7: 13–22 (1992); Lisziewicz et al., *Proc. Nat. Acad. Sci. USA* 91:7942–7946 (1994), both references incorporated herein fully by reference. The anti-tat inhibitor has been effective as a genetic treatment of HIV-1 infected tissue (Biasolo et al, *J. Virology* 70:2154–2161 (1966), incorporated herein fully by reference. By incorporating anti-tat and anti-gag sequences into a single oligoribonucleotide molecule, we synthesized a multi-functional antisense inhibitor with the following sequence:

```
5'-gggaaacaaa cuuggcaaug aaa - cucucgcacc caucucucuc cuucu-3'.   (SEQ ID NO:26)
         anti-tat                       anti-gag
```

(SEQ ID NO:26). When derivatized as in the prior examples, the poly-DNP-anti-HIV multifunctional inhibitor is denoted Compound XX. The 27-mer anti-gag sequence, when derivatized with poly DNP is denoted Compound I, the 22-mer anti-gag sequence, when derivatized with poly DNP is denoted Compound XXII, and the 23-mer anti-tat sequence, when derivatized, is denoted Compound XXIII.

B. Methods

In Vitro Studies of Inhibition of IV By Antisense Compounds

To study the efficacy of Compound XX in inhibiting infection by HIV, we performed as series of studies using an in vitro system known in the art, using PHA stimulated PBMC cells selected for infectivity by HIV, grown at SRA Technologies, Inc. Rockville, Md..

The cells were infected with HIV strains HIV-1 MN, HIV-1 RF, and HIV multi-drug resistant strain HIV-US-1. The multi-drug resistant strain, HIV-US-1 is resistant to Indinivar, Ritonavir, Saquinavir, Nelinavir and to a lesser extent AZT. These strains have been shown to be responsible for infection in humans. The multi-drug resistant strain has been recently described to be resistant to multiple drugs, and is therefore very difficult to treat effectively using conventional, currently available compounds.

C. Results

The antisense inhibitor Compound XX inhibited HIV infection with an $EC_{50}$ of from 26 to 70 µg/ml. Furthermore, the inhibitor successfully inhibited infection by every of the HIV strains tested, including the recently discovered multi-drug resistant strain HIV-US-1. The finding that Compound XX inhibited the multi-drug resistant HIV strain was completely unexpected, in that this compound is the only compound yet found which can inhibit this strain of HIV.

Furthermore, we expect that Compounds XXI, XXII, and XXIII will be at least 10 times more potent at inhibiting HIV-1 than the PS-DNA inhibitors previously published.

Thus, these completely unexpected results show that derivatized antisense inhibitors of this invention are effective at inhibiting HIV infection.

Example XII

Inhibition of HIV Infection In Vivo

A. Introduction

Having showed the inhibitory capability of the antisense inhibitors of this invention against HIV infection in vitro, we then develop studies in vivo. Study of HIV infection in vivo can be accomplished using a strain of mice (SCID) in which their native immune systems have been eliminated. Previous studies have shown that these mice are susceptible to infection with human HIV, show the effects of infection, can respond to therapeutic intervention, and are therefore a model system for the studies of human HIV disease and its treatment (M. E. Harper, *Nucleic Acid-Based Therapeutics*, CHI Symposium, Jun. 19–20, 1995, incorporated herein fully by reference).

B. Methods 1.1 In Vivo Model for Human HIV

CB17 SCID mice are obtained from Tarconic, 273 Hover Avenue, Germantown, N.Y. 12526-5320. This strain of mice has been used for studies of HIV infection and is recognized to be useful in developing models for treatment of human HIV disease.

1.2 In Vivo Infection of SCID Mice With HIV

CB17 SCID mice are infected with IV strains HIV-1 MN, HIV-1 RF, and the Multi-drug Resistant strain, HIV-1 US-1, according to the methods of Harper et al. (1995).

1.3 Time Course of HIV Disease

The symptoms, signs, pathophysiological changes, viral titers and other aspects of the course of HIV disease will be monitored using methods of Harper et al. (1995).

1.4 Methods for Antisense Therapy of SCID Mice

Mice will be treated with either: (1) Compounds XX, XXI, XXII, and/or XXII, (2) the sense equivalents of either Compounds XX, XXI, XXII, XXIII, or (3) a random sequence oligoribonucleotide (Compound XX). Treatment will be via intraperitoneal and/or oral administration. Compounds will be given in increasing doses, beginning with a dose of about 0.25 µg/kg, and increasing in half-log doses until a dose of about 80 µg/kg is achieved.

C. Results

We expect that treatment of HIV-infected mice in vivo with Compounds XX, XXI, XXII, and/or XXIII will result in the inhibition of infection by HIV-1. We also expect that treatment with antisense Compounds will result in decreased HIV viral titers in the blood of infected mice. We further expect that the signs and symptoms of HIV disease in infected mice will be reduced by treatment with anti HIV oligoribonucleotides.

We expect that similar therapy in humans infected with HIV will show similar results. In the event that toxic side effects are observed, we will decrease the size of the derivatized antisense inhibitor.

Example XIII

Multifunctional Inhibitors Have An Entropy Advantage Over Monofunctional Inhibitors The design of the multifunctional Compound IV (FIG. 10) described in Example V, and Compound XVIII described in Example X above are based on a new concept. Compared to mixtures of monofunctional inhibitors used in combinatorial therapy, an equivalent multifunctional inhibitor has an entropy advantage which may become very large under certain circumstances.

In dilute solutions the molar entropy decrease due to the transport of a monofunctional inhibitor from external medium of volume V to the inside of virus or bacteria of total volume V', before binding to the target occurs, is given by $\Delta S_1 = R \ln (V'/V)$. Although binding has not yet occurred, this first step costs $T\Delta S_1$ to the overall binding free energy. When a mixture of n different monofunctional inhibitors is used, the entropy decrease for transporting 1 mole of each inhibitor is equal to $\Delta S_2 = n R \ln (V'/V)$. However, when this mixture is replaced by a multifunctional inhibitor with n different binding groups, the corresponding entropy decrease, $\Delta S_3$, is equal to: R ln (V'/V), because only 1 mole of the multifunctional inhibitor is transported. This smaller entropy decrease can reduce the effective concentration ($EC_{50}$) by a factor equal to $$r = \frac{(IC_{50})_3}{(IC_{50})_2} = \exp\left\{\left(\frac{n-1}{n}\right)\ln(V'/V)\right\}$$

where $(IC_{50})_3$ and $(IC_{50})_2$ represent the concentrations required for 50% inhibition for an n-functional inhibitor and that for an equivalent mixture of n mono-functional inhibitors, respectively.

On account of steric constraints, the multifunctional inhibitor cannot be bound simultaneously to more than one site. But when the number of inhibitor molecules is significantly larger than the number of specific sites inside a virus or cell, for any given site we could consider only its equilibrium with the inhibitor as a monodentate ligand. As an example, for V'/V=$5 \times 10^{-5}$, the calculated values of r are 1, 0.007, 0.001 and 0.00005 for n=1, 2, 3 and infinity, respectively.

The observed intraperitoneal $ED_{50}$ values shown in Table 3 for the monofunctional RT inhibitor poly-DNP-oligo A, for the bifunctional inhibitor Compound I and for the multifunctional inhibitor Compound IV were found to be 50, 0.25, and 0.1 mg/Kg (ip) respectively. These values illustrate the advantage of using multifunctional inhibitors. The enhanced efficacy of compounds IV and VIII are clearly due to their additional antisense function, because all the control compounds II, XVII and XVIII have lower inhibition activity. The entropy advantage gained by incorporating two antisense sequences in the structure of Compound IV has lowered its effective dosage by about 500-fold. Therefore a multifunctional inhibitor is effective in a lower total concentration of a mixture of monofunctional inhibitors, each of the same concentration as the multifunctional inhibitor. Because monofunctional inhibitors are which widely used in combinatorial therapies, lower effective dosages with multifunctional inhibitors results in reduced toxicity as well as reduced cost of treatment.

As will be understood, in order to effectively treat diseases with the antisense oligomers of the present invention, it is necessary that the oligomers are able to gain access to the afflicted area. Using the derivatized oligoribonucleotides of this invention, the oligomers have improved access to the cells and sub-cellular structures. Moreover, it will be appreciated that any of the antisense oligomers prepared in accordance with the present invention that show antiproliferative effect can be used in treatment.

It also is apparent from the above disclosure that the oligoribonucleotides of this invention can be delivered orally and retain inhibitory efficacy. The formulation of oral dosage forms is within the scope of the art of oral administration of therapeutic compounds and will not be discussed further.

It is expected that direct injection into lesions and intravenous administration of the antisense oligomers of the present invention are currently the most efficient and expedient forms of delivery. However, it is also anticipated that a variety of topical formulations will show similar efficacy. Intravenous administration is generally indicated in advanced cases of non-localized diseases.

The antisense oligomers of the present invention can be formulated into a medicament to aid in stabilizing and/or aiding their delivery to the afflicted site. A multitude of appropriate formulations can be found in the formulary known to all pharmaceutical chemists: *Remington's Pharmaceutical Sciences, 15th Edition,* 1975. Mack Publishing Company, Easton, Pa. 18042. (Chapter 87: Blaug, Seymour).

For direct injection or in intravenous administration of antisense oligomers it is conventional to include in the formulations physiologically acceptable buffers, excipients, and/or other delivery agents. For topical use, appropriate formulations include for example, pastes, ointments, jelly, waxes, oils, lipids, anhydrous absorption bases, oil-in-water or water-in-oil emulsions, emulsions carbowax (polyethylene glycols of a variety of molecular weights), semi-solid gels, and semi-solid mixtures containing carbowax. Topical application may be highly effective. For example, certain investigators have demonstrated that certain antisense oligomers are readily absorbed by the skin. In particular, these researcher used methylphosphonates. Uhlmann et al. *Chemical Reviews* 90:543–584 at p. 568 (1990). Because of the ease with which the derivatized oligoribonucleotides of the instant invention penetrate into cells, we expect that transdermal application of DNP-derivatized oligoribonucleotides will be practical.

Moreover, liposomes have shown great promise in assisting in the delivery of oligomers, in general, and antisense oligomers in particular. One highly advantageous example of a suitable liposomal delivery vehicle is prepared from cationic lipids, such as those available under the trademark LIPOFECTIN (Life Technologies, Inc., Bethesda, Md.). Other, neutral liposomes can also be useful for delivery of the oligoribonucleotides of this invention.

The concentration or dose of the antisense oligomers of the present invention should range from 0.1 $\mu$M through 20 $\mu$M, depending on the seriousness of the affliction, or alternatively from 0.5 $\mu$M to 5 $\mu$M. The dosage will also depend on the type of oligonucleotide and also upon its chemical modification, if any. As will be understood, the schedule of the administration will also depend on the type of oligomers used and their chemical modification, since different chemical modification effects the half-life of these compounds.

Incorporation by Reference

A variety of references are cited herein. Some of such references have been expressly incorporated by reference. To the extent that any reference cited herein is not expressly incorporated by reference above, the disclosures of each of such references are hereby incorporated by reference in their entirety.

Equivalents

While the present invention has been described in connection with specific embodiments thereof, it will be understood that it is capable of further modification, and this application is intended to cover any variations, uses, or adaptations of the invention following, in general, the principles of the invention and including such departures from the present disclosure as come within known or customary practice in the art to which the invention pertains and as may be applied to the essential features hereinbefore set forth, and as fall within the scope of the invention and any equivalents thereof.

What is claimed is:

1. An oligoribonucleotide complementary to a sequence of nucleotides found in a virus or a cell, said oligoribonucleotide comprising at least one 2'-O position conjugated with a compound of the following general structure:

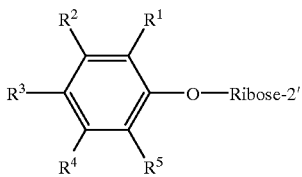

wherein $R^1$, $R^2$, $R^3$, $R^4$, and $R^5$ are independently, H, $NO_2$, halide, linear or branched alkyl, linear or branched acyl, linear or branched alkylene, linear or branched O-alkyl, linear or branched amido, linear or branched S-alkyl, mono or disubstituted amine, linear or branched thioamido, phosphothionate, or phosphothioate.

2. The oligoribonucleotide of claim 1, wherein $R^1$ and $R^3$ are $NO_2$ as follows:

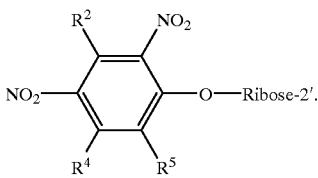

3. The oligoribonucleotide of claim 2, wherein $R^2$, $R^4$, and $R^5$ are H.

4. The oligoribonucleotide of claim 1, wherein the oligoribonucleotide has a length of between 10 and 50 nucleotides.

5. The oligoribonucleotide of claim 2, wherein the oligoribonucleotide has a length of between 10 and 50 nucleotides.

6. The oligoribonucleotide of claim 3, wherein the oligoribonucleotide has a length of between 10 and 50 nucleotides.

7. The oligoribonucleotide of claim 1, wherein at least one of the 5' and 3' ends of the oligoribonucleotide is conjugated with a compound of the following general structure:

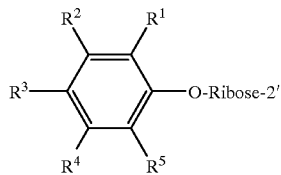

wherein $R^1$, $R^2$, $R^3$, $R^4$, and $R^5$ are independently H, $NO_2$, halide, linear or branched alkyl, linear or branched acyl, linear or branched alkylene, linear or branched O-alkyl, linear or branched amido, linear or branched S-alkyl, mono or disubstituted amine, linear or branched thioamido, phosphothionate, or phosphothioate.

8. The oligoribonucleotide of claim 7, wherein $R^1$ and $R^3$ are $NO_2$.

9. The oligoribonucleotide of claim 8, wherein $R^2$, $R^4$, and $R^5$ are H.

10. The oligoribonucleotide of claim 1, wherein said oligoribonucleotide is complementary to a gene from the human immunodeficiency virus (HIV).

11. The oligoribonucleotide of claim 1, wherein said oligoribonucleotide is complementary to a gene from the hepatitis B virus.

12. The oligoribonucleotide of claim 1, wherein said oligoribonucleotide is complementary to a gene found in a leukemia cell.

13. A multifunctional inhibitor made by a method to decrease the entropy associated with cellular uptake, said method comprising:

(1) selecting at least 2 oligoribonucleotide sequences which separately are at least partially effective at inhibiting gene expression:
(2) combining said sequences into a combined oligoribonucleotide of between 10 and 50 nucleotides in length; and
(3) derivatizing said combined oligoribonucleotide at at least one 2'-O position with a poly substituted phenyl compound according the compound in claim 1.

14. The multifunctional inhibitor of claim 13, wherein at least one gene is a gene of a cancer cell.

15. The multifunctional inhibitor of claim 14, wherein said cancer cell is selected from the group consisting of a leukemia cell and a breast cancer cell.

16. The multifunctional inhibitor of claim 15, wherein said gene is selected from the group consisting of bcr-abl, erb-B2 and RIα/PKA.

17. The multifunctional inhibitor of claim 13, wherein at least one gene is a viral gene.

18. The multifunctional inhibitor of claim 17, wherein said viral gene is selected from the group consisting of a hepatitis B virus gene and a human immunodeficiency virus gene.

19. The multifunctional inhibitor of claim 17, wherein said viral gene is a human immunodeficiency virus gene selected from the group consisting of tat and gag.

20. The multifunctional inhibitor of claim 13, wherein said different oligoribonucleotide sequences are selected from the same gene.

21. The multifunctional inhibitor of claim 13, wherein at least one of said oligoribonucleotide sequences is an antisense nucleotide sequence.

22. The oligoribonucleotide of claim 1 that is an antisense oligoribonucleotide.

23. A poly substituted phenyl derivatized oligoribonucleotide having a sequence selected from the group consisting of SEQ ID NO:3, SEQ ID NO:5, SEQ ID NO:8, SEQ ID NO:9, SEQ ID NO: 10, SEQ ID NO:13, SEQ ID NO:14, SEQ ID NO: 15, SEQ ID NO: 16, SEQ ID NO: 19, SEQ ID NO:20, SEQ ID NO:21, SEQ ID NO:23, SEQ ID NO:24, SEQ ID NO:25 and SEQ ID NO:26.

24. A poly substituted phenyl derivatized oligoribonucleotide which hybridizes with the complement of at least one sequence selected from the group consisting of SEQ ID NO:3, SEQ ID NO:5, SEQ ID NO:8, SEQ ID NO:9, SEQ ID NO: 10, SEQ ID NO:13, SEQ ID NO:14, SEQ ID NO: 15, SEQ ID NO:16, SEQ ID NO:19, SEQ ID NO:20, SEQ ID NO:21, SEQ ID NO:23, SEQ ID NO:24, SEQ ID NO:25 and SEQ ID NO:26 under stringent hybridization conditions.

25. A method of delivering an oligoribonucleotide to a cell, comprising the steps of:
selecting an oligoribonucleotide complementary to a nucleotide sequence found in a virus or a cell, said oligoribonucleotide being derivatized at a plurality of the 2'-O positions with a compound of the following structure:

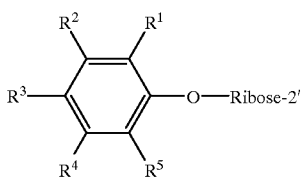

wherein $R^1$, $R^2$, $R^3$, $R^4$, and $R^5$ are independently H, $NO_2$, halide, linear or branched alkyl, linear or branched acyl, linear or branched alkylene, linear or branched O-alkyl, linear or branched amido, linear or branched S-alkyl, mono or disubstituted amine, linear or branched thioamido, phosphothionate, or phosphothioate; and
administering said derivatized oligoribonucleotide to at least one of said virus and said cell.

26. The method of claim 25, wherein $R^1$ and $R^3$ are $NO_2$ as follows:

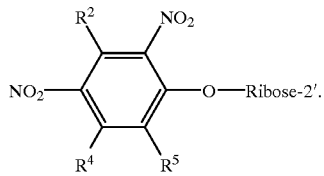

27. The method of claim 26, wherein $R^2$, $R^4$, and $R^5$ are H.

28. The method of claim 27, wherein the oligoribonucleotide has a length of between 10 and 50 nucleotides.

29. The method of claim 26, wherein the oligoribonucleotide has a length of between 10 and 50 nucleotides.

30. The method of claim 25, wherein the oligoribonucleotide has a length of between 10 and 50 nucleotides.

31. The method of claim 25, wherein the oligoribonucleotide sequence is an antisense oligoribonucleotide sequence.

32. A method for increasing the effectiveness of an oligoribonucleotide targeted to a gene associated with a disease or condition in an animal, comprising:
selecting a non-derivatized oligoribonucleotide comprising a plurality of 2'-O positions wherein said oligoribonucleotide is at least partially effective in reducing the symptoms of said disease;
derivatizing said oligoribonucleotide at said plurality of 2'-O positions with a substituted phenyl moiety therby making a derivatized oligoribonucleotide; and
administering said derivatized oligoribonucleotide to said animal, and wherein said derivatized oligoribonucleotide is more effective at decreasing symptoms of disease than is said non-derivatized oligoribonucleotide.

33. The method of claim 32, wherein the oligoribonucleotide has a length of between 10 and 50 nucleotides.

34. The method of claim 32, wherein said oligoribonucleotide comprises at least one sequence selected from the group consisting of SEQ ID NO:3, SEQ ID NO:5, SEQ ID NO:8, SEQ ID NO:9, SEQ ID NO:10, SEQ ID NO: 13, SEQ ID NO: 14, SEQ ID NO: 15, SEQ ID NO: 16, SEQ ID NO: 19, SEQ ID NO:20, SEQ ID NO:21, SEQ ID NO:23, SEQ ID NO:24, SEQ ID NO:25 and SEQ ID NO:26.

35. The method of claim 32, wherein said oligoribonucleotide hybridizes with the complement of at least one sequence selected from the group consisting of SEQ ID NO:3, SEQ ID NO:5, SEQ ID NO:8, SEQ ID NO:9, SEQ ID NO:10, SEQ ID NO: 13, SEQ ID NO: 14, SEQ ID NO:15, SEQ ID NO: 16, SEQ ID NO: 19, SEQ ID NO:20, SEQ ID NO:21, SEQ ID NO:23, SEQ ID NO:24, SEQ ID NO:25 and SEQ ID NO:26 under stringent hybridization conditions.

36. The method of claim 32, wherein said substituted phenyl moiety is a 2,4 dinitrophenyl moiety.

37. The method of claim 36, wherein said oligoribonucleotide comprises at least one sequence selected from the group consisting of SEQ ID NO:3, SEQ ID NO:5, SEQ ID NO:8, SEQ ID NO:9, SEQ ID NO:10, SEQ ID NO: 13, SEQ ID NO:14, SEQ ID NO: 15, SEQ ID NO: 16, SEQ ID NO:

19, SEQ ID NO:20, SEQ ID NO:21, SEQ ID NO:23, SEQ ID NO:24, SEQ ID NO:25 and SEQ ID NO:26.

38. The method of claim 32, wherein said oligoribonucleotide hybridizes with the complement of at least one sequence selected from the group consisting of SEQ ID NO:3, SEQ ID NO:5, SEQ ID NO:8, SEQ ID NO:9, SEQ ID NO:10, SEQ ID NO:13, SEQ ID NO:14, SEQ ID NO: 15, SEQ ID NO: 16, SEQ ID NO: 19, SEQ ID NO:20, SEQ ID NO:21, SEQ ID NO:23, SEQ ID NO:24, SEQ ID NO:25 and SEQ ID NO:26 under stringent hybridization conditions.

39. The method of claim 32, wherein the sequence of said oligoribonucleotide is selected to inhibit the expression of a gene found in a virus or a cell, wherein said sequence hybridizes with at least one of a regulatory domain of said gene and a gene transcript from said regulatory domain of said gene.

40. The method of claim 32, wherein said gene comprises a sequence selected from the group consisting of bcr-abl, erb-B2, RIα/PKA, tat and gag.

41. The method of claim 32, wherein said gene is a human immunodeficiency virus (HIV) gene, and said oligoribonucleotide is complementary to a sequence selected from the group consisting of tat and gag.

42. The method of claim 32, wherein said disease or condition is associated with HIV.

43. The method of claim 42, wherein said human immunodeficiency virus is caused by a multi-drug resistant strain of disease or condition.

44. The method of claim 32, wherein said disease or condition is associated with human breast cancer.

45. The method of claim 44, wherein said breast cancer is associated with the expression of a sequence selected from the group consisting of bcr-abl, erb-B2 and RIα/PKA.

46. The method of claim 32, wherein said disease or condition is associated with leukemia.

47. The method of claim 32, wherein said disease or condition is associated with hepatitis B.

48. The method of claim 32, wherein said oligoribonucleotide is an antisense oligonucleotide.

* * * * *

SEQUENCE LISTING

<160> NUMBER OF SEQ ID NOS: 26

<210> SEQ ID NO 1
<211> LENGTH: 15
<212> TYPE: RNA
<213> ORGANISM: Artificial Sequence
<220> FEATURE:
<223> OTHER INFORMATION: Retroviral reverse transcriptase inhibitor

<400> SEQUENCE: 1
aaaaaaaaaa aaaaa                                                        15

<210> SEQ ID NO 2
<211> LENGTH: 24
<212> TYPE: RNA
<213> ORGANISM: Murine Leukemia Virus
<220> FEATURE:
<221> NAME/KEY:
<222> LOCATION: env gene nucleotides 8107 - 8131
<223> OTHER INFORMATION: Target sequence for complementary
      oligoribonucleotide

<400> SEQUENCE: 2
ggacccugca uucuuauucg auua                                              24

<210> SEQ ID NO 3
<211> LENGTH: 15
<212> TYPE: RNA
<213> ORGANISM: Murine Leukemia Virus
<220> FEATURE:
<222> LOCATION: env gene, nucleotides 8107 - 8131
<223> OTHER INFORMATION: Complementary to portion of SEQ ID NO:2

<400> SEQUENCE: 3
aagaaugcag ggucc                                                        15

<210> SEQ ID NO 4
<211> LENGTH: 15
<212> TYPE: RNA
<213> ORGANISM: Artificial Sequence
<220> FEATURE:
<223> OTHER INFORMATION: Random Sequence for Murine Leukemia Virus env
      gene.

<400> SEQUENCE: 4
ugacccugca uucug                                                        15

<210> SEQ ID NO 5
<211> LENGTH: 32
<212> TYPE: RNA
<213> ORGANISM: Murine Leukemia Virus
<220> FEATURE:
<222> LOCATION: A portion of the env gene and a portion of the protease
      gene
<223> OTHER INFORMATION: Complementary to a portion of Murine Leukemia
      virus env gene and complementary to a portion of Murine Leukemia
      Virus protease.

<400> SEQUENCE: 5
gggacagucu gguacauaag aaugcagggu cc                                     32

<210> SEQ ID NO 6
<211> LENGTH: 32
<212> TYPE: RNA
<213> ORGANISM: Murine Leukemia Virus
<220> FEATURE:

```
<222> LOCATION: A portion of the env gene and a portion of the protease
      gene
<223> OTHER INFORMATION: Sense sequence complementary to SEQ ID NO:5

<400> SEQUENCE: 6
cccugucaga ccauguauuc uuacguccca gg                                    32

<210> SEQ ID NO 7
<211> LENGTH: 47
<212> TYPE: RNA
<213> ORGANISM: Artificial sequence
<220> FEATURE: synthetic RNA
<223> OTHER INFORMATION: Random sequence

<400> SEQUENCE: 7
ggguccagcu aaaugcaggc auaaauguga acgcgaacgg uaucagc                    47

<210> SEQ ID NO 8
<211> LENGTH: 17
<212> TYPE: RNA
<213> ORGANISM: Duck Hepatitis B Virus
<220> FEATURE:
<222> LOCATION: Viral polymerase gene, nucleotides 2428 - 2445
<223> OTHER INFORMATION: Target sequence for complementary
      oligoribonucleotide

<400> SEQUENCE: 8
aauccugcug acggccc                                                     17

<210> SEQ ID NO 9
<211> LENGTH: 17
<212> TYPE: RNA
<213> ORGANISM: Duck Hepatitis B Virus
<220> FEATURE:
<222> LOCATION: Viral polymerase RNA transcript, nucleotides 2428 - 2445
<223> OTHER INFORMATION: Complementary to SEQ ID NO.:8

<400> SEQUENCE: 9
gggccgucag caggauu                                                     17

<210> SEQ ID NO 10
<211> LENGTH: 20
<212> TYPE: RNA
<213> ORGANISM: Duck Hepatitis B Virus
<220> FEATURE:
<222> LOCATION: Viral polymerase RNA transcript, nucleotides 2468 - 2487
<223> OTHER INFORMATION: Complementary to a portion of Duck Hepatitis B
      Virus polymerase

<400> SEQUENCE: 10
ggguguaugg aaaagccguc                                                  20

<210> SEQ ID NO 11
<211> LENGTH: 19
<212> TYPE: RNA
<213> ORGANISM: Duck Hepatitis B Virus
<220> FEATURE:
<222> LOCATION: Nucleotide positions 2469 - 2488
<223> OTHER INFORMATION: Sense sequence for SEQ ID NO.:10

<400> SEQUENCE: 11
gacggcuuuu ccauacacc                                                   19

<210> SEQ ID NO 12
<211> LENGTH: 20
<212> TYPE: RNA
<213> ORGANISM: Artificial
```

```
<220> FEATURE:
<223> OTHER INFORMATION: Random sequence for Duck Hepatitis B Virus

<400> SEQUENCE: 12 gggauuc

```
<223> OTHER INFORMATION: Sense sequence

<400> SEQUENCE: 18
gggccaguga ggaggcacgc                                                    20

<210> SEQ ID NO 19
<211> LENGTH: 18
<212> TYPE: RNA
<213> ORGANISM: Homo sapiens
<220> FEATURE:
<223> OTHER INFORMATION: Complementary to a portion of the RI/PKA gene

<400> SEQUENCE: 19
gggucucuca ggucgagc                                                      18

<210> SEQ ID NO 20
<211> LENGTH: 18
<212> TYPE: RNA
<213> ORGANISM: Homo sapiens
<220> FEATURE:
<222> LOCATION: Portion of the bcr-abl gene
<223> OTHER INFORMATION: Complementary to a portion of the bcr-abl gene

<400> SEQUENCE: 20
gggcuucuuc cuuauuga                                                      18

<210> SEQ ID NO 21
<211> LENGTH: 37
<212> TYPE: RNA
<213> ORGANISM: Homo sapiens
<220> FEATURE:
<223> OTHER INFORMATION: One portion complementary to a portion of the RI/PKA gene, another portio
      complementary to a portion of the bcr-abl gene.

<400> SEQUENCE: 21
gggcuucuuc cuuauugaug ggucucucag gucgagc                                  37

<210> SEQ ID NO 22
<211> LENGTH: 18
<212> TYPE: RNA
<213> ORGANISM: Artificial Sequence
<220> FEATURE:
<223> OTHER INFORMATION: Random sequence for bcr-abl and RI/PKA genes

<400> SEQUENCE: 22
gggaucguuc agagucua                                                      18

<210> SEQ ID NO 23
<211> LENGTH: 27
<212> TYPE: RNA
<213> ORGANISM: Human Immunodeficiency Virus type 1
<220> FEATURE:
<222> LOCATION: A portion of the gag gene
<223> OTHER INFORMATION: Complementary to a portion of the gag gene

<400> SEQUENCE: 23
ggcucucgca cccaucucuc uccuucu                                            27

<210> SEQ ID NO 24
<211> LENGTH: 22
<212> TYPE: RNA
<213> ORGANISM: Human Immunodeficiency Virus type 1
<220> FEATURE:
<222> LOCATION: Portion of the gag gene
<223> OTHER INFORMATION: Complementary to a portion of the gag gene

<400> SEQUENCE: 24
```

```
ggcacccauc ucucuccuuc ua                                              22
```

<210> SEQ ID NO 25
<211> LENGTH: 23
<212> TYPE: RNA
<213> ORGANISM: Human Immunodeficiency Virus-1
<220> FEATURE:
<222> LOCATION: Portion of the tat gene
<223> OTHER INFORMATION: Complementary to a portion of the tat gene

<400> SEQUENCE: 25

```
gggaaacaaa cuuggcaaug aaa                                             23
```

<210> SEQ ID NO 26
<211> LENGTH: 48
<212> TYPE: RNA
<213> ORGANISM: Human Immunodeficiency Virus type 1
<220> FEATURE:
<222> LOCATION: A portion of the tat gene and a portion of the gag gene
<223> OTHER INFORMATION: A portion is complementary to a portion of the
      tat gene, another portion is complementary to a portion of the gag
      gene

<400> SEQUENCE: 26

```
gggaaacaaa cuuggcaaug aaacucucgc acccaucucu cuccuucu                  48
```